United States Patent
Chen et al.

(10) Patent No.: US 9,555,107 B2
(45) Date of Patent: Jan. 31, 2017

(54) COMPOSITIONS AND METHODS FOR THE TREATMENT OF DISEASES AND DISORDERS ASSOCIATED WITH CYTOKINE SIGNALING

(75) Inventors: Yvonne M. Chen, San Mateo, CA (US); Anan Chuntharapai, Colma, CA (US); Dimitry Danilenko, Millrae, CA (US); Wenjun Ouyang, Foster City, CA (US); Susan Sa, San Francisco, CA (US); Patricia Valdez, San Francisco, CA (US); Terence Wong, Alameda, CA (US); Jianfeng Wu, San Francisco, CA (US); Yan Zheng, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/404,241

(22) Filed: Feb. 24, 2012

(65) Prior Publication Data

US 2013/0224146 A1    Aug. 29, 2013

Related U.S. Application Data

(60) Continuation of application No. 12/759,496, filed on Apr. 13, 2010, now abandoned, which is a division of application No. 11/565,395, filed on Nov. 30, 2006, now Pat. No. 7,737,259.

(60) Provisional application No. 60/741,640, filed on Dec. 2, 2005, provisional application No. 60/822,597, filed on Aug. 16, 2006.

(51) Int. Cl.

| | |
|---|---|
| A61K 39/395 | (2006.01) |
| A61K 38/17 | (2006.01) |
| A61K 38/20 | (2006.01) |
| C07K 16/24 | (2006.01) |
| C07K 16/28 | (2006.01) |
| A61K 39/00 | (2006.01) |

(52) U.S. Cl.
CPC ............ *A61K 39/3955* (2013.01); *A61K 38/17* (2013.01); *A61K 38/1793* (2013.01); *A61K 38/20* (2013.01); *C07K 16/244* (2013.01); *C07K 16/2866* (2013.01); *A61K 2039/505* (2013.01); *A61K 2039/57* (2013.01); *C07K 2317/76* (2013.01); *C07K 2317/92* (2013.01)

(58) Field of Classification Search
CPC .................. A61K 38/20; A61K 2039/55527; C07K 14/54; C07K 14/7155; C07K 16/244; C07K 16/2866
See application file for complete search history.

(56) References Cited

U.S. PATENT DOCUMENTS

| | | | |
|---|---|---|---|
| 5,965,704 A | 10/1999 | Lok et al. | |
| 6,274,710 B1 | 8/2001 | Dumoutier et al. | |
| 6,331,613 B1 | 12/2001 | Dumoutier et al. | |
| 6,359,117 B1 | 3/2002 | Dumoutier et al. | |
| 6,551,799 B2 | 4/2003 | Gurney et al. | |
| 6,740,520 B2 | 5/2004 | Goddard et al. | |
| 6,875,845 B2 | 4/2005 | Presnell et al. | |
| 6,897,292 B2 | 5/2005 | Presnell et al. | |
| 6,939,545 B2 | 9/2005 | Jacobs et al. | |
| 7,279,559 B2 | 10/2007 | Jacobs et al. | |
| 7,307,161 B1 | 12/2007 | Jacobs et al. | |
| 7,951,372 B1 | 5/2011 | Jacobs et al. | |
| 8,124,088 B2 * | 2/2012 | Xu et al. | 424/143.1 |
| 8,163,286 B2 * | 4/2012 | Xu et al. | 424/141.1 |
| 2001/0024652 A1 | 9/2001 | Dumoutier et al. | |
| 2001/0027099 A1 | 10/2001 | Zondag et al. | |
| 2003/0012788 A1 | 1/2003 | Renauld et al. | |
| 2003/0022827 A1 | 1/2003 | Weiss et al. | |
| 2003/0023033 A1 | 1/2003 | Dumoutier et al. | |
| 2003/0157106 A1 | 8/2003 | Jacobs et al. | |
| 2003/0170823 A1 | 9/2003 | Presnell et al. | |
| 2003/0170839 A1 | 9/2003 | Fouser et al. | |
| 2003/0219862 A1 | 11/2003 | Agarwal et al. | |
| 2004/0023341 A1 | 2/2004 | Xu et al. | |
| 2004/0071699 A1 | 4/2004 | Renauld et al. | |
| 2004/0110189 A1 | 6/2004 | Dumoutier et al. | |
| 2004/0136954 A1 | 7/2004 | Grusby et al. | |
| 2004/0152125 A1 | 8/2004 | Presnell et al. | |
| 2004/0156849 A1 | 8/2004 | Gurney | |
| 2004/0180399 A1 | 9/2004 | Renauld et al. | |
| 2004/0209330 A1 | 10/2004 | Xu et al. | |
| 2004/0236075 A1 | 11/2004 | Dumoutier et al. | |
| 2005/0042220 A1 | 2/2005 | Li et al. | |
| 2005/0065321 A1 | 3/2005 | Presnell et al. | |
| 2005/0137129 A1 | 6/2005 | Agarwal et al. | |
| 2005/0153400 A1 | 7/2005 | Jacobs et al. | |

(Continued)

FOREIGN PATENT DOCUMENTS

| | | |
|---|---|---|
| CN | 1184633 | 6/1998 |
| EP | 1191035 A2 | 3/2002 |

(Continued)

OTHER PUBLICATIONS

Boehncke et al., Clinics in Dermatology, 25(6):596-605, Nov.-Dec. 2007.*
Liang, et al. "Interleukin (IL)-22 and IL-17 are coexpressed by TH17 cells and cooperatively enhance expression of antimicrobial peptides", J. Exp. Med. 203(10):2271-2279, 2006.
Aggarwal, et al., "Interleukin-23 promotes a distinct CD4 T cell activation state characterized by the production of interleukin-17", Journal of Biological Chemistry, 278: 1910-1914, (2003).
Blumberg, et al., "Interleukin 20: Discovery, receptor identification and role in epidermal function", Cell, 104: 9-19, (2001).

(Continued)

*Primary Examiner* — Marianne P Allen
(74) *Attorney, Agent, or Firm* — Anna Tan; Christopher DeVry; Arnold & Porter LLP

(57) ABSTRACT

Compositions and methods are provided for the diagnosis and treatment of inflammation and autoimmune disorders, such as psoriasis. Compositions and methods for modulating IL-23 or IL-22 signaling are provided.

2 Claims, 53 Drawing Sheets

(56) References Cited

U.S. PATENT DOCUMENTS

| | | |
|---|---|---|
| 2005/0158760 A1 | 7/2005 | Jacobs et al. |
| 2005/0214314 A1 | 9/2005 | Presnell et al. |
| 2005/0238648 A1 | 10/2005 | Jacobs et al. |
| 2005/0271619 A1 | 12/2005 | Dumoutier et al. |

FOREIGN PATENT DOCUMENTS

| | | | |
|---|---|---|---|
| WO | WO 00/24758 | 5/2000 | |
| WO | WO 01/16318 A2 | 3/2001 | |
| WO | WO 01/36467 | 5/2001 | |
| WO | WO 01/98342 A1 | 12/2001 | |
| WO | WO 02/10393 A2 | 2/2002 | |
| WO | WO 02/068476 A2 | 9/2002 | ............ C07K 16/24 |
| WO | WO 03/010290 A2 | 2/2003 | |
| WO | WO 03/029262 A2 | 4/2003 | |
| WO | WO 2004/085475 | 10/2004 | |
| WO | WO 2004/085476 A2 | 10/2004 | ............ C07K 16/00 |
| WO | WO 2005/000897 A2 | 1/2005 | ............ C07K 16/00 |
| WO | WO 2007/027714 A2 | 3/2007 | |
| WO | WO 2007/027761 A2 | 3/2007 | |
| WO | WO 2007/098170 A1 | 8/2007 | ............ C07K 16/24 |
| WO | WO 2007/100643 A2 | 9/2007 | |
| WO | WO 2007/149814 A1 | 12/2007 | |

OTHER PUBLICATIONS

Boniface, et al., "IL-22 inhibits epidermal differentiation and induces proinflammatory gene expression and migration of human keratinocytes", The Journal of Immunology, 174: 3695-3702, (2005).

Cargill, et al., "A large-scale genetic association study confirms IL1 2B and leads to the identification of IL23R as psoriasis-risk genes", The American Journal of human genetics, 80: 273-290, (2007).

Coussens, et al., "Inflammation and cancer", Nature, 420: 860-867, (2002).

Donnelly, et al., "The expanded family of class II cytokines that share the IL-10 receptor-2 (IL-10R2) chain", Journal of Leukocyte Biology, vol. 76, pp. 314-321, (2004).

Dumoutier, et al., "Cloning and Characterization of Il-22 binding protein, a natural antagonist of IL-10-related T cell-derived inducible factor /IL-22", Journal of Immunology, vol. 166, No. 12, pp. 7090-7095, (2001).

Dumoutier, et al., "IL-TIF/IL-22: Genomic Organization and Mapping of the Human and Mouse Genes", Genes and Immunity, vol. 1, pp. 488-494, (2000).

Eckert, et al., "S100 proteins in the epidermis", The Journal of Investigative Dermatology, 123: 23-33, (2004).

Fickenscher, et al., "The interleukin-10 family of cytokines", Trends in Immunology, 23(2): 89-96, (2002).

Happel, et al., "Cutting edge: roles of Toll-like receptor 4 and IL-23 in IL-17 expression in response to Klebsiella pneumoniae infection", Journal of Immunology, vol. 170, No. 9, pp. 4432-4436, (2003).

Harrington, et al., "Interleukin 17-producing CD4+ effector T cells develop via a lineage distinct from the T helper type 1 and 2 lineages", Nature Immunology, vol. 6, No. 11, pp. 1123-1132, (2005).

Holscher, et al., "Targeting IL-23 in autoimmunity", Current Opinion in Investigational Drugs, vol. 6, No. 5, pp. 489-495, (2005).

Hunter, et al., "New IL-12-Family members: IL-23 and IL-27, cytokines with divergent functions", Nature Reviews,: Immunology, 5: 521-531, (2005).

Infante-Duarte, "Microbial lipopeptides induce the production of IL-17 in Th cells", The Journal of Immunology, 165: 6107-6115, (2000).

Kotenko, et al., "Identification, cloning and characterization of a novel soluble receptor that binds IL-22 and neutralizes its activity", Journal of Immunology, vol. 166, No. 12, pp. 7096-7103, (2001).

Langowski, et al., "IL-23 promotes tumor incidence and growth", Nature, 442: 461-465, (2006).

Langrish, et al., "IL-23 Drives a pathogenic T cell population that induces autoimmune Inflammation", Journal of Experimental Medicine, vol. 201, No. 2, pp. 233-240, (2005).

Lankford, et al., "A unique role for IL-23 in promoting cellular immunity", Journal of Leukocyte Biology, vol. 73, No. 1, pp. 49-56, (2003).

Lejeune, et al., "Interleukin-22 (IL-22) activates the JAK/STAT, ERK, JNK and p38 MAP kinase pathways in a rat hepatoma cell line. Pathways that are shared with and distinct from IL-10", The Journal of Biological Chemistry, vol. 277, No. 37, pp. 33676-33682, (2002).

Li, et al., "Temporal associations between interleukin 22 and the extracellular domains of IL-22R and IL-10R2", International Immunopharmacology, vol. 4, No. 5, pp. 693-708, (2004).

Liang, et al., "Interleukin (IL)-22 and IL-17 are co expressed by Th17 cells and cooperatively enhance expression of antimicrobial peptides", vol. 203, No. 10, pp. 2271-2279, (2006).

Liu, et al., "Signaling through the murine T cell receptor induces IL-17 production in the absence of co stimulation, IL-23 or dendritic cells", Molecules and Cells, vol. 20, No. 3, pp. 339-347, (2005).

Mangan, et al., "Transforming growth factor-beta induces development of the T(H)17 lineage", Nature, vol. 441, No. 7090, pp. 231-234, (2006).

Nagakawa, et al., "Expression of interleukin-22 in murine carcinoma cells did not influence tumor growth in vivo but did improve survival of the inoculated hosts", Scandinavian Journal of Immunology, vol. 60, No. 5, pp. 449-454, (2004).

Pan, et al., "Hydrodynamic gene delivery of interleukin-22 protects the mouse liver from concanavalin A-, carbon tetrachloride-, and Fas ligand-induced injury via activation of STAT3", Cellular & Molecular Immunology, vol. 1, No. 1, pp. 43-49, (2004).

Park, et al., A distinct lineage of CD4 T cells regulates tissue inflammation by producing interleukin 17, Nature Immunology, vol. 6, No. 11, pp. 1133-1141, (2005).

Piskin, et al., "In vitro and in situ expression of IL-23 by Keratinocytes in healthy skin and psoriasis lesions: Enhanced expression in psoriatic skin", The Journal of Immunology, 176: 1908-1915, (2006).

Radaeva, et al., "Interleukin 22 (IL-22) plays a protective role in T cell-mediated murine hepatitis: IL-22 is a survival factor for hepatocytes via stat3 activation", Hepatology, vol. 39, No. 5, pp. 1332-1342, (2004).

Renauld, et al., "Class II cytokine receptors and their ligands: key antiviral and inflammatory modulators", Nature Reviews/Immunology, 3: 667-676, (2003).

Rollins, et al., "Inflammatory chemokines in cancer growth and progression", European Journal of Cancer, 42: 760-767, (2006).

Rutitzky, et al., "CD4 T cells producing pro-inflammatory interleukin-17 mediate high pathology in schistosomiasis", Mem'orias do instituto oswaldo cruz, vol. 101, Suppl. 1, pp. 327-330, (2006).

La Sala, et al., "G(i)-protein-dependent inhibition of IL-12 production is mediated by activation of the phosphatidylinositol 3-kinase-protein 3 kinase B/Akt pathway and JNK", Journal of Immunology, vol. 175, No. 5, pp. 2994-2999, (2005).

Sutton, et al., "A crucial role for leukin (IL)-1 in the induction of IL-17-producing T cells that mediate autoimmune encephalomyelitis", The Journal of Experimental Medicine, vol. 203, No. 7, pp. 1685-1691, (2006).

Trinchieri, et al., "The IL-12 family of heterodimeric cytokines: new players in the regulation of T cell responses", Immunity, vol. 19, No. 5, pp. 641-644, (2003).

Vandenbroeck, et al., "Inhibiting Cytokines of the Interleukin-12 Family: Recent Advances and Novel Challenges", Journal of Pharmacy and Pharmacology, vol. 56, pp. 145-160, (2004).

Veldhoen, et al., "TGF in the context of an inflammatory cytokine milieu supports de novo differentiation of IL-17 producing T cells", Immunity, 24: 179-189, (2006).

Weber, et al., "IL-22-mediated tumor growth reduction correlates with inhibition of ERK1/2 and AKT phosphorylation and induction

(56) References Cited

OTHER PUBLICATIONS of cell cycle arrest in the G2-M phase", Journal of Immunology, vol. 177, No. 11, pp. 8266-8272, (2006).

Weighardt, et al., Identification of a TLR4- and TRIF-dependent activation program of dendritic cells, European Journal of Immunology, vol. 34, No. 2, pp. 558-564, (2004).

Weiss, et al., "Cloning and murine IL-22 receptor alpha 2 and comparison with its human counterpart", Genes and Immunity, vol. 5, No. 5, pp. 330-336, (2004).

Whittington, et al., "Interleukin-22: a potential immunomodulatory molecule in the lung", American Journal of Respiratory Cell and Molecular Biology, vol. 31, No. 2, pp. 220-226, (2004).

Wilson, et al., "Development, cytokine profile and function of human interleukin 17-producing helper T cells", Nature Immunology, vol. 8, No. 9, pp. 950-957, (2007).

Xia, et al., "Transgenic delivery of VEGF to mouse skin leads to an inflammatory condition resembling human psoriasis", Blood, 102(1): 161-168, (2003).

Xie, et al., "Interleukin (IL)-22, a novel human cytokine that signals through the interferon receptor-related proteins CRF2-4 and IL-22R", Journal of Biological Chemistry, vol. 275, No. 40, pp. 31335-31339, (2000).

Xu, et al., "A soluble class II cytokine receptor, IL-22RA2, is a naturally occurring IL-22 antagonist", Proceedings of the National Academy of Sciences, vol. 98, No. 17, pp. 9511-9516, (2001).

Zheng, et al., "Interleukin-22, a TH17 cytokine mediates Il-23 induced dermal inflammatory and Acanthosis", Nature, 445(7128): 648-651, (2007).

Kreymborg, et al., "IL-22 is expressed by Th17 cells in an IL-23-dependent fashion, but not required for the development of auto-immune encephalomyelitis", The Journal of Immunology, 179: 8098-8104, (2007).

Sonnenberg, et al., "Functional biology of the IL-22-IL-22R pathway in regulating immunity and inflammation at barrier surfaces", Advances in Immunology, vol. 107, Chapter 1, pp. 1-29, (2010).

Sugimoto, et al., "IL-22 ameliorates intestinal inflammation in a mouse model of ulcerative colitis", The Journal of Clinical Investigation, vol. 118, No. 2, pp. 534-544, (2008).

Zenewicz, et al., "IL-22 but not IL-17 provides protection to hepatocytes during acute liver inflammation", Immunity, 27(4): 647-659, (2007).

\* cited by examiner

CTTCAGAACAGGTTCTCCTTCCCCAGTCACCAGTTGCTCGAGTTAGAATTGTCTGCAATG
GCCGCCCTGCAGAAATCTGTGAGCTCTTTCCTTATGGGACCCTGGCCACCAGCTGCCTC
CTTCTCTTGGCCCTCTTGGTACAGGGAGGAGCAGCTGCGCCCATCAGCTCCCACTGCAGG
CTTGACAAGTCCAACTTCCAGCAGCCCTATATCACCAACCGCACCTTCATGCTGGCTAAG
GAGGCTAGCTTGGCTGATAACAACACAGACGTTCGTCTCATTGGGGAGAAACTGTTCCAC
GGAGTCAGTATGAGTGAGCGCTGCTATCTGATGAAGCAGGTGCTGAACTTCACCCTTGAA
GAAGTGCTGTTCCCTCAATCTGATAGGTTCCAGCCTTATATGCAGGAGGTGGTGCCCTTC
CTGGCCAGGCTCAGCAACAGGCTAAGCACATGTCATATTGAAGGTGATGACCTGCATATC
CAGAGGAATGTGCAAAAGCTGAAGGACACAGTGAAAAAGCTTGGAGAGAGTGGAGAGATC
AAAGCAATTGGAGAACTGGATTTGCTGTTTATGTCTCTGAGAAATGCCTGCATTTGACCA
GAGCAAAGCTGAAAAATGAATAACTAACCCCCTTTCCCTGCTAGAAATAACAATTAGATG
CCCCAAAGCGATTTTTTTTAACCAAAAGGAAGATGGGAAGCCAAACTCCATCATGATGGG
TGGATTCCAAATGAACCCCTGCGTTAGTTACAAAGGAAACCAATGCCACTTTTGTTTATA
AGACCAGAAGGTAGACTTTCTAAGCATAGATATTTATTGATAACATTTCATTGTAACTGG
TGTTCTATACACAGAAACAATTTATTTTTTAAATAATTGTCTTTTTCCATAAAAAAGAT
TACTTTCCATTCCTTTAGGGGAAAAAACCCCTAAATAGCTTCATGTTTCCATAATCAGTA
CTTTATATTTATAAATGTATTTATTATTATTATAAGACTGCATTTTATTTATATCATTTT
ATTAATATGGATTTATTTATAGAAACATCATTCGATATTGCTACTTGAGTGTAAGGCTAA
TATTGATATTTATGACAATAATTATAGAGCTATAACATGTTTATTTGACCTCAATAAACA
CTTGGATATCCC

FIG. 1

MAALQKSVSSFLMGTLATSCLLLLALLVQGGAAAPISSHCRLDKSNFQQPYITNRTFMLAKEASLADNNTDV
RLIGEKLFHGVSMSERCYLMKQVLNFTLEEVLFPQSDRFQPYMQEVVPFLARLSNRLSTCHIEGDDLHIQRN
VQKLKDTVKKLGESGEIKAIGELDLLFMSLRNACI

Signal peptide: amino acids 1-33

FIG. 2

```
MRTLLTILTVGSLAAHAPEDPSDLLQHVKFQSSNFENILTWDSGPEGTPDTVYSIEYKTY
GERDWVAKKGCQRITRKSCNLTVETGNLTELYYARVTAVSAGGRSATKMTDRFSSLQHTT
LKPPDVTCISKVRSIQMIVHPTPTPIRAGDGHRLTLEDIFHDLFYHLELQVNRTYQMHLG
GKQREYEFFGLTPDTEFLGTIMICVPTWAKESAPYMCRVKTLPDRTWTYSFSGAFLFSMG
FLVAVLCYLSYRYVTKPPAPPNSLNVQRVLTFQPLRFIQEHVLIPVFDLSGPSSLAQPVQ
YSQIRVSGPREPAGAPQRHSLSEITYLGQPDISILQPSNVPPPQILSPLSYAPNAAPEVG
PPSYAPQVTPEAQFPFYAPQAISKVQPSSYAPQATPDSWPPSYGVCMEGSGKDSPTGTLS
SPKHLRPKGQLQKEPPAGSCMLGGLSLQEVTSLAMEESQEAKSLHQPLGICTDRTSDPNV
LHSGEEGTPQYLKGQLPLLSSVQIEGHPMSLPLQPPSGPCSPSDQGPSPWGLLESLVCPK
DEAKSPAPETSDLEQPTELDSLFRGLALTVQWES
```

Fibronectin Type III Domain: amino acids 18-155

FIG. 3

MMPKHCFLGFLISFFLTGVAGTQSTHESLKPQRVQFQSRNFHNILQWQPGRALTGNSSVYFVQYKIMFSCSM
KSSHQKPSGCWQHISCNFPGCRTLAKYGQRQWKNKEDCWGTQELSCDLTSETSDIQEPYYGRVRAASAGSYS
EWSMTPRFTPWWETKIDPPVMNITQVNGSLLVILHAPNLPYRYQKEKNVSIEDYYELLYRVFIINNSLEKEQ
KVYEGAHRAVEIEALTPHSSYCVVAEIYQPMLDRRSQRSEERCVEIP

Fibronectin Type III Domains: amino acids 26-68, 100-161, and 162-263

FIG. 4

Generation of anti-IL-22 antibodies

| Clone | IC for hIL-22 | IC for mIL-22 | Block hIL-22 | Block mIL-22 | Isotype |
|---|---|---|---|---|---|
| 1A7 | | | ** | | |
| 1F6 | | | ** | | |
| 3F11 | **** | **** | ***** | ***** | IgG2a |
| 6F11 | | | ** | ** | |
| 6G7 | | | **** | ** | |
| 7E2 | | | *** | *** | |
| 8E11 | **** | **** | ***** | ***** | IgG1 |
| 10E4 | | | ** | | |
| 11H4 | | | ***** | ***** | IgG1 |
| 14B7 | | **** | * | * | IgG2a |
| 14B9 | *** | **** | | | IgG2a |
| 15A4 | **** | **** | ** | | IgG2b |
| 15E4 | **** | **** | *** | * | IgG2b |
| 19G5 | | | | *** | |
| 20E5 | *** | *** | | | IgG2b |

IC: intracellular cytokine staining

FIG. 5

Affinity of anti-IL-22 antibodies to hIL-22

| | ka (1/Ms) | kd (1/s) | KD (nM) |
|---|---|---|---|
| 11H4 | 1.21E+06 | 2.56E-04 | 0.21 |
| 8E11 | 4.98E+05 | 3.58E-04 | 0.72 |
| 3F11 | ND | ND | ND |

FIG. 9

*Detecting IL-22 production by intracellular cytokine staining*
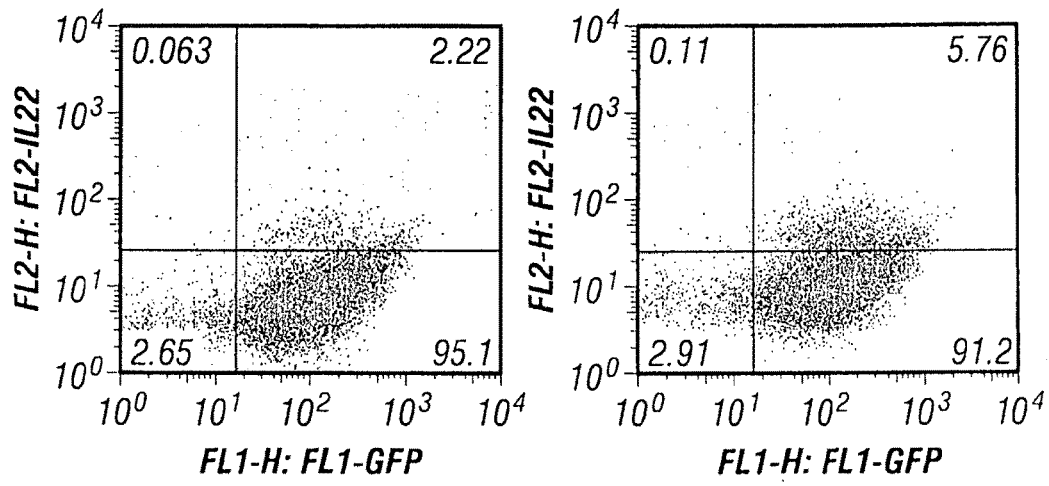
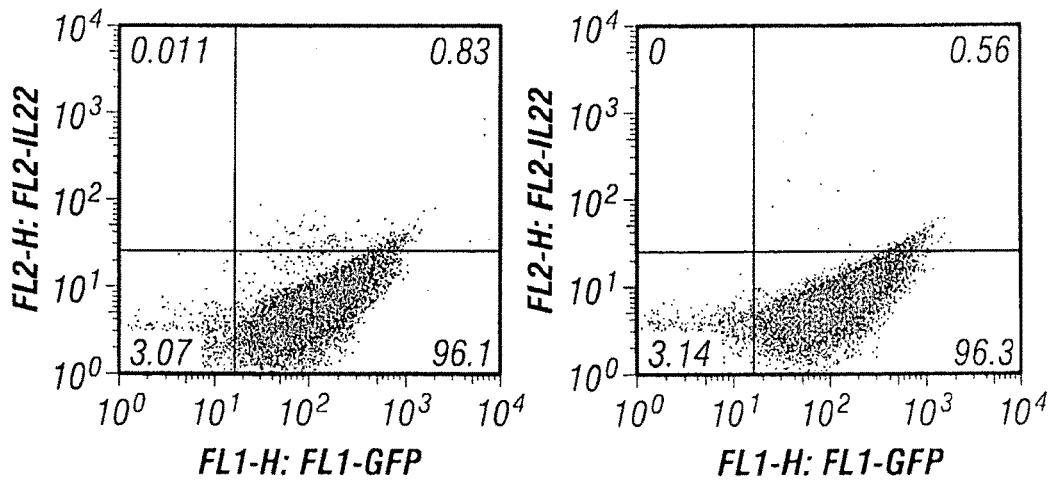
FIG. 10A Detecting IL-22 production by intracellular cytokine staining
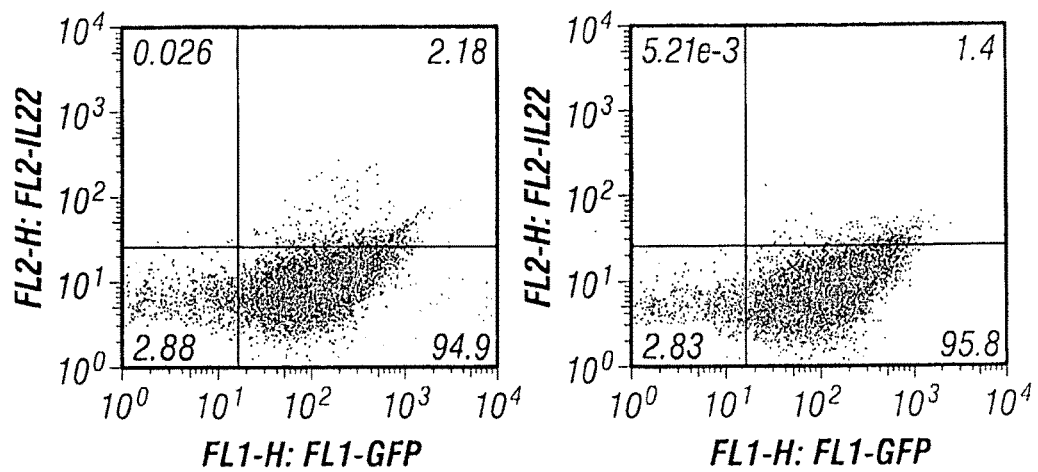
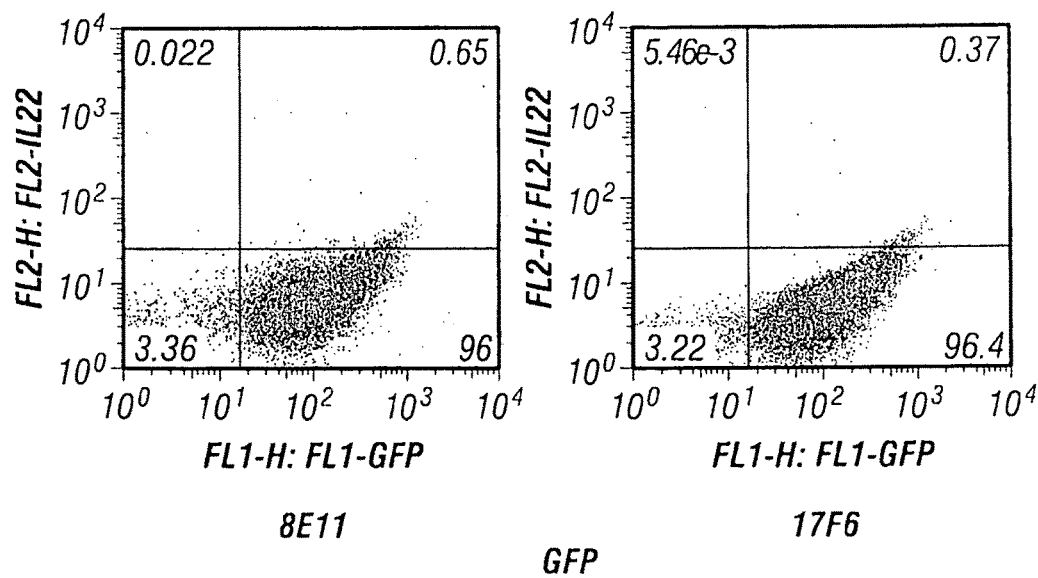
FIG. 10B

*Detecting IL-22 production by intracellular cytokine staining*
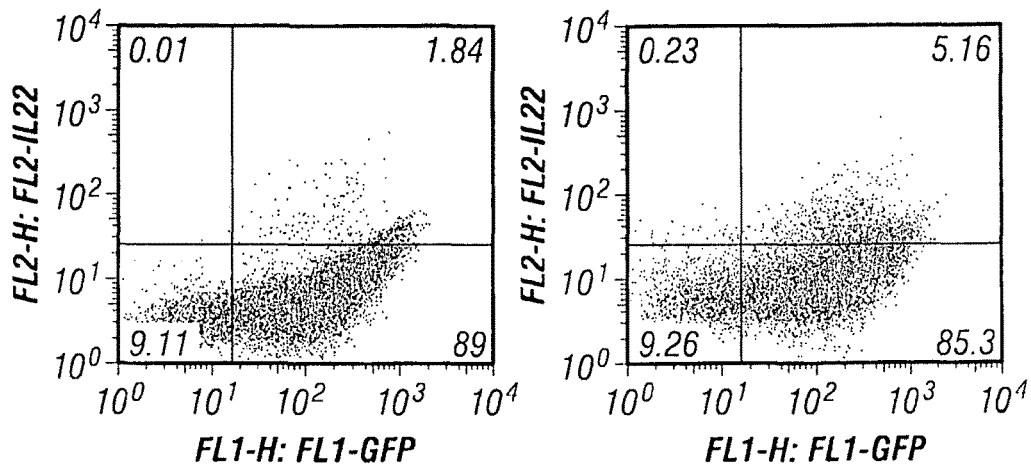
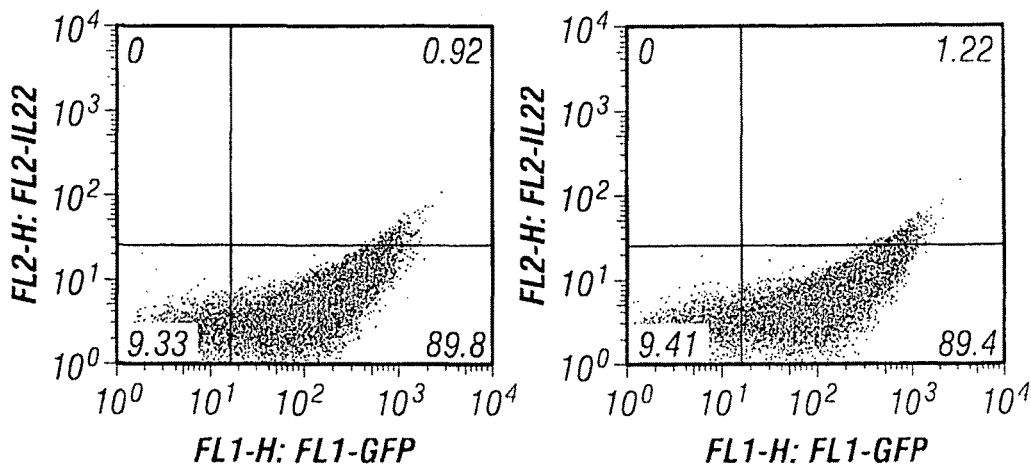
FIG. 10C

*Detecting IL-22 production by intracellular cytokine staining*
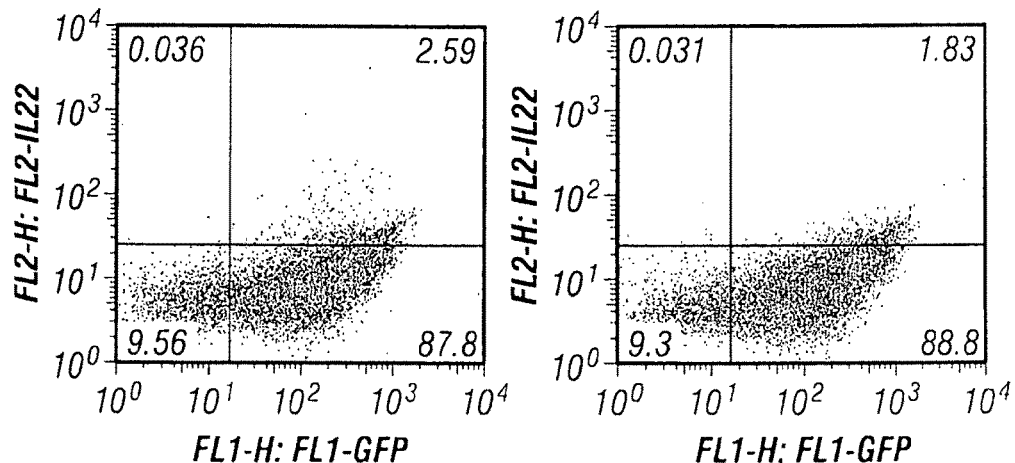
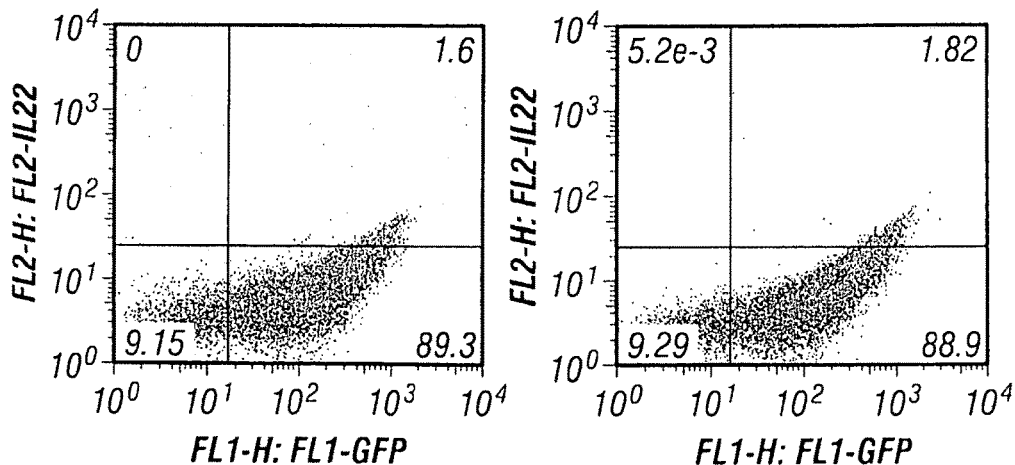
8E11  17F6
mIL-20-GFP
FIG. 10D

*Detecting IL-22 production by intracellular cytokine staining*
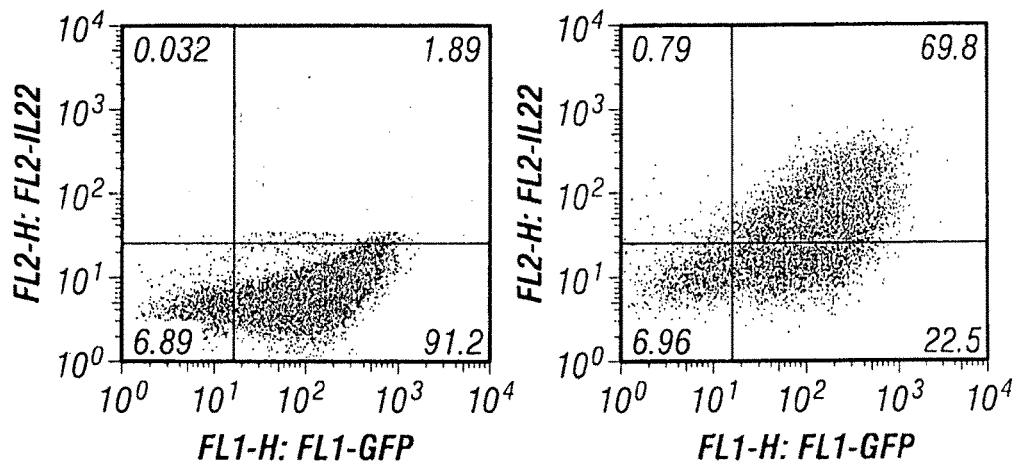
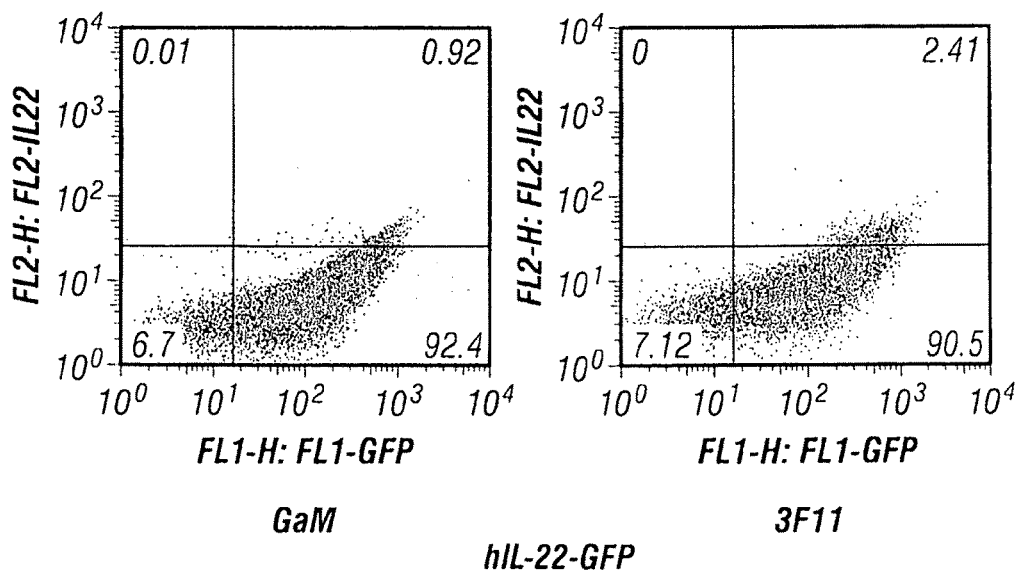
FIG. 10E

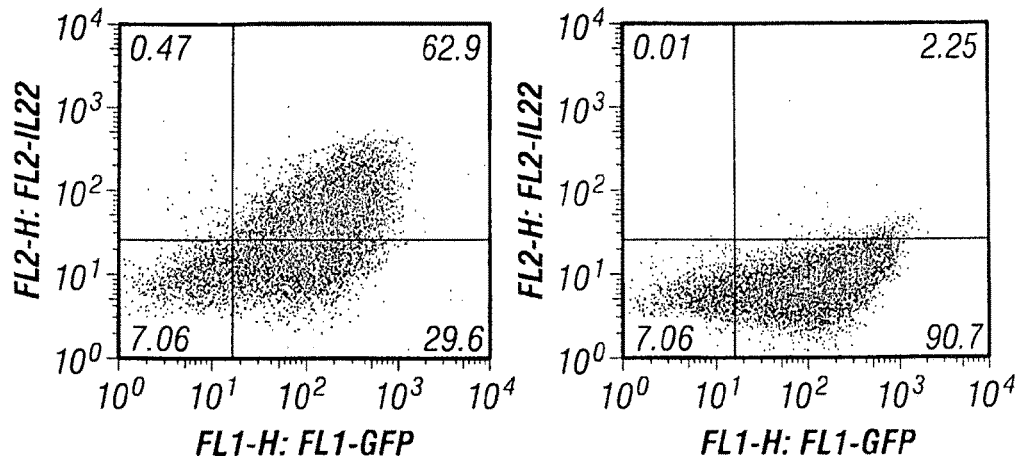
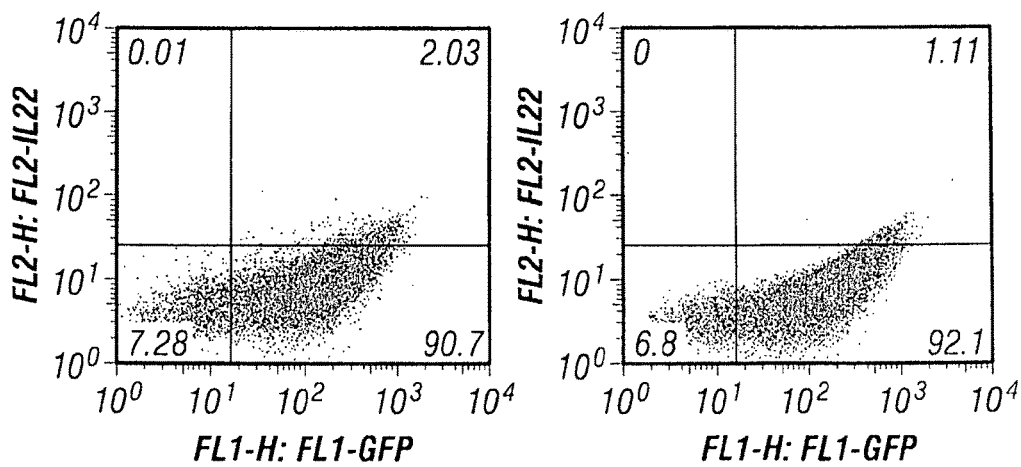
FIG. 10F

*Detecting IL-22 production by intracellular cytokine staining*
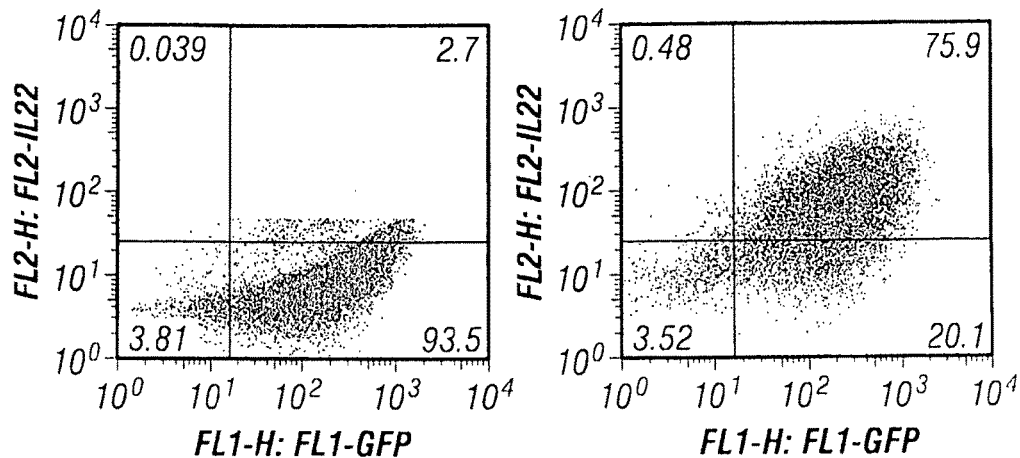
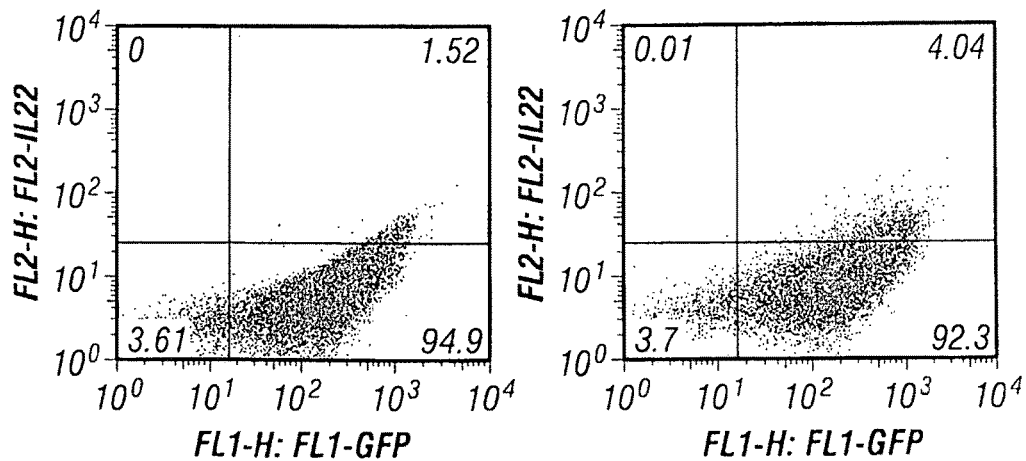
FIG. 10G

*Detecting IL-22 production by intracellular cytokine staining*
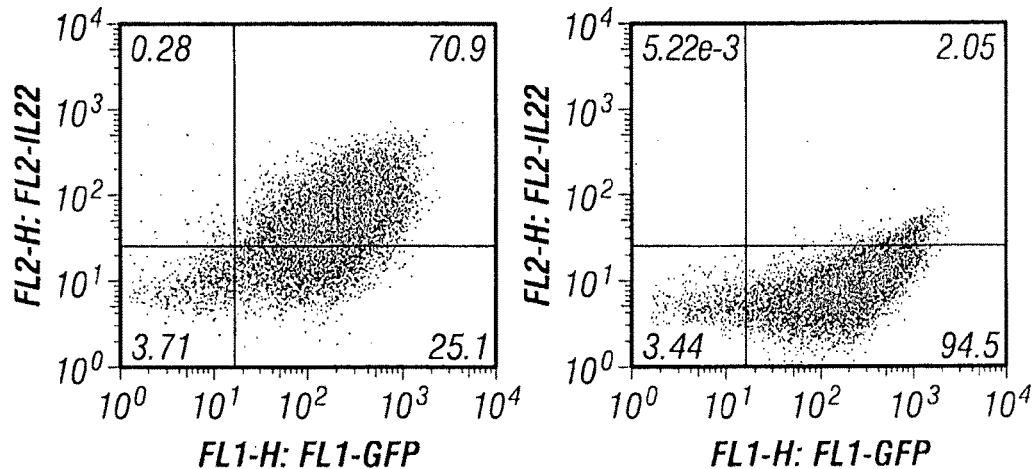
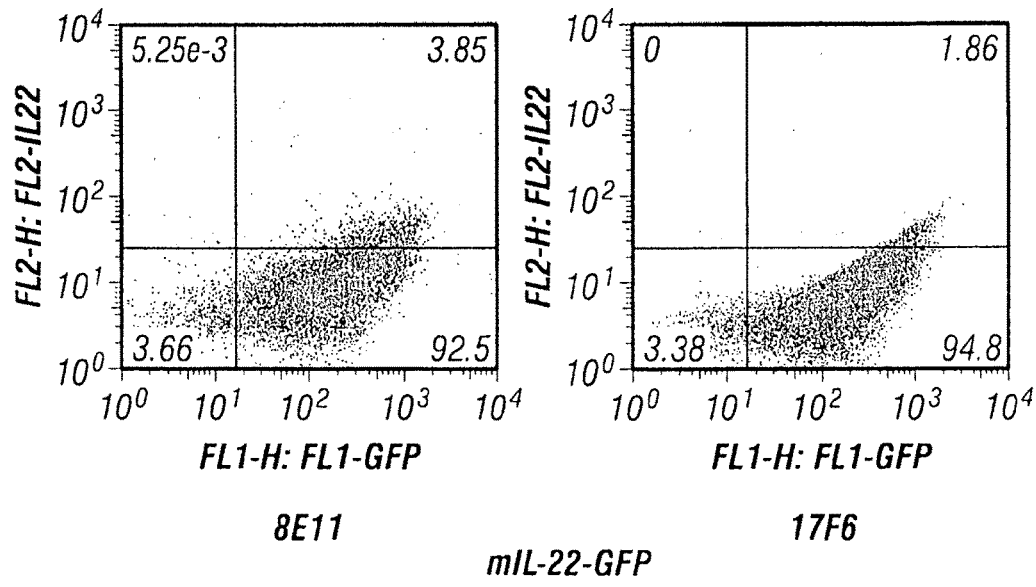
FIG. 10H Generation of anti-IL-22R antibodies
293 cells expressing hIL-22R          293 cells
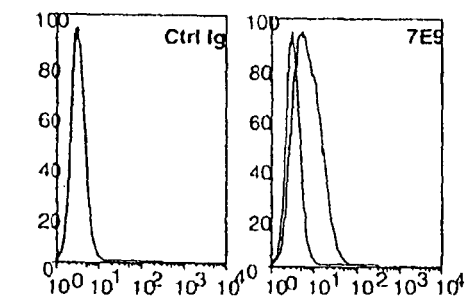
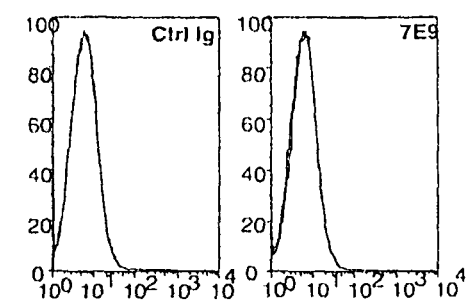
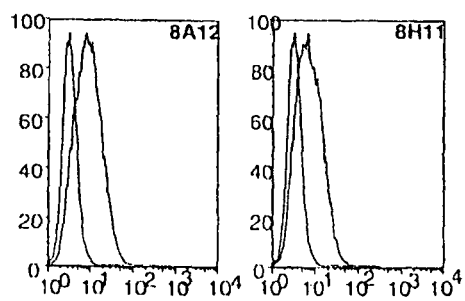
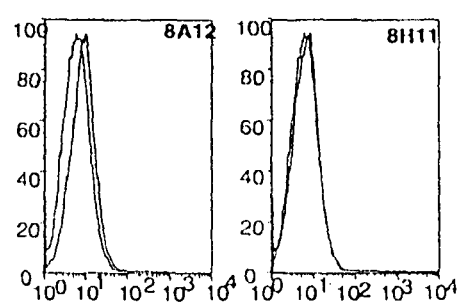
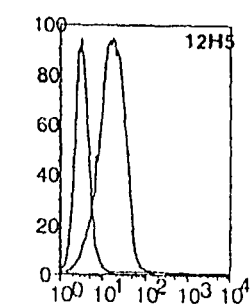
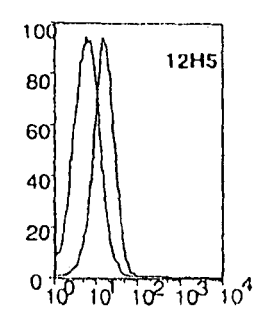
IL-22R
FIG. 16

Expression of IL-22R on primary keratinocytes

Effect of IL-10 family cytokines on 4 day cultured human epidermis

Effect of IL-10 family cytokines on Cytokeratin16 IHC

Effect of IL-10 family cytokines on Psoriasin (S100A7) IHC

Genes induced by IL-22 from keratinocytes are also elevated in psoriatic skins Selection criteria: >= 2 folds induction by IL-22L on keratinocytes, minimal expression level > 500 on both chips.
There are total 47 probes showed >2 fold induction by IL-22 from keratinocytes

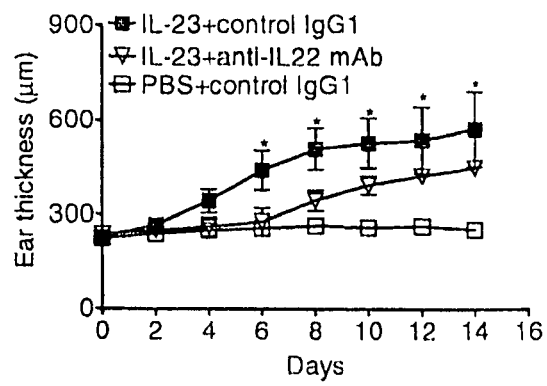
B  IL-23+ control IgG1    C  IL-23+ control IgG1
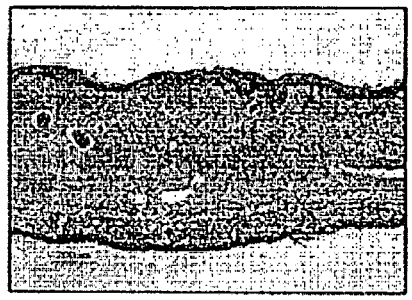   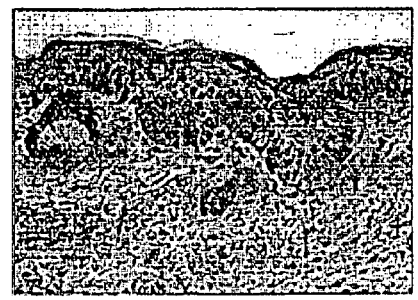
D  IL-23+anti-IL22 mAb   E  IL-23+anti-IL22 mAb
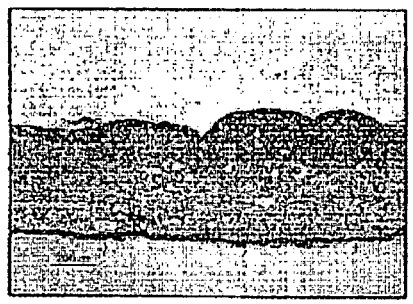   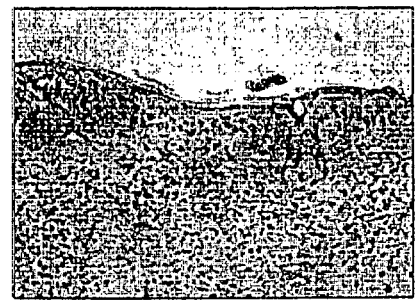
F  PBS+control IgG1    G  PBS+control IgG1
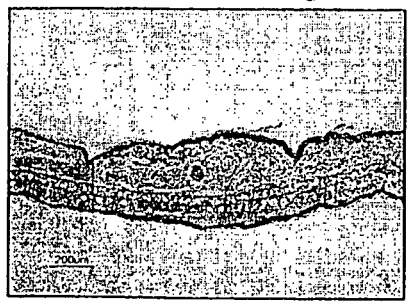   
FIG. 29

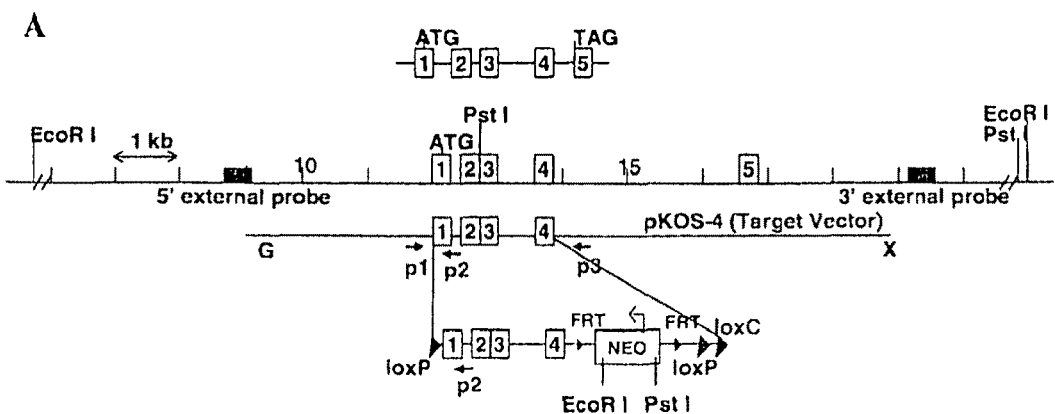
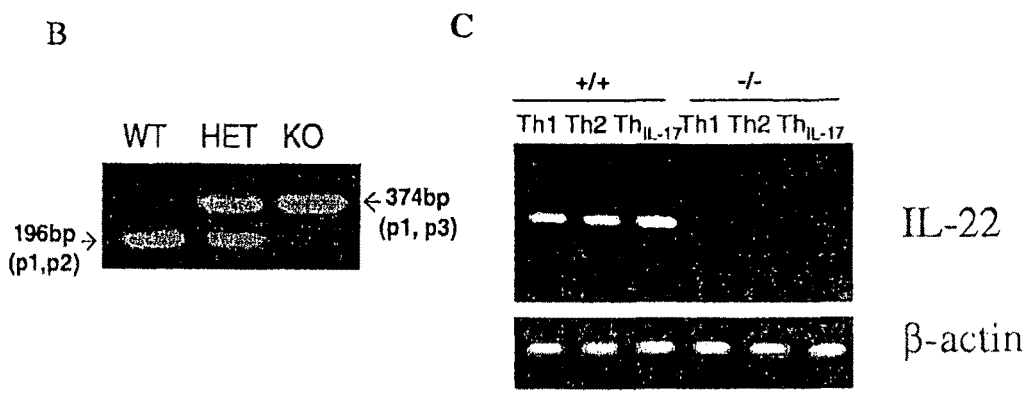
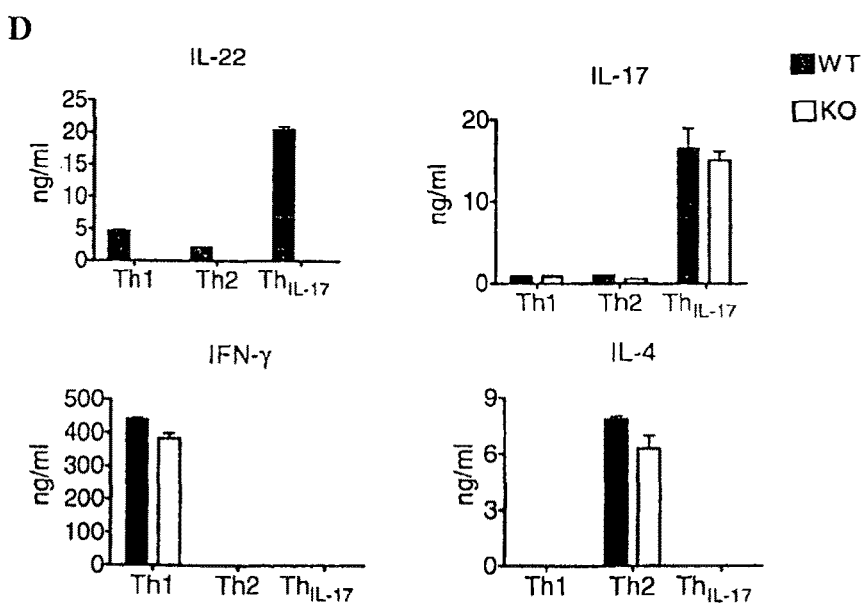
FIG. 30

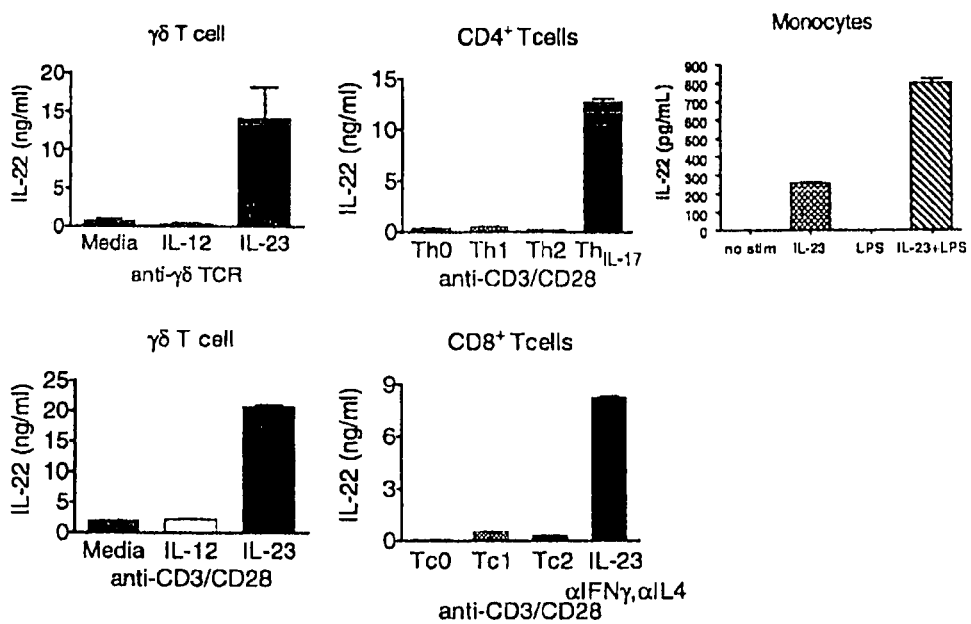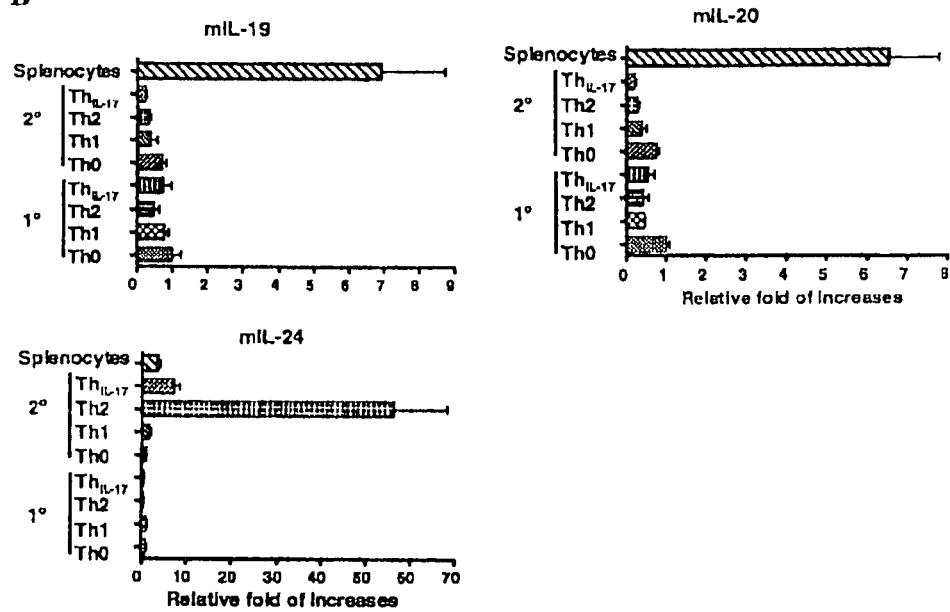
FIG. 33

A DO11.10 TCR transgenic T cell differentiation, primary 48h
Real-time RT-PCR:
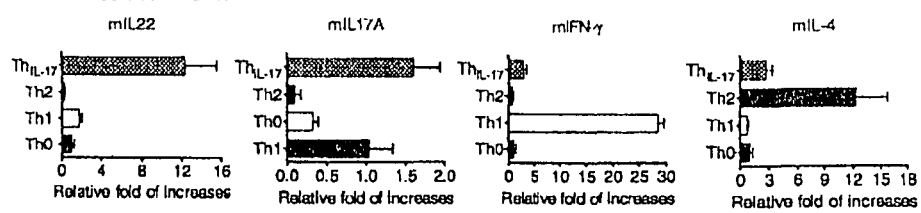
ELISA:
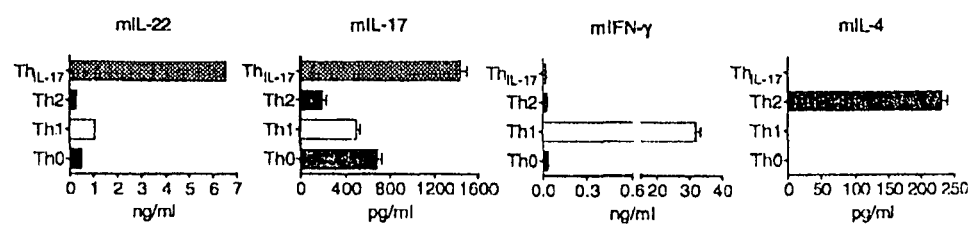
B DO11.10 TCR transgenic T cell differentiation, anti-CD3/28 restimulation 48h
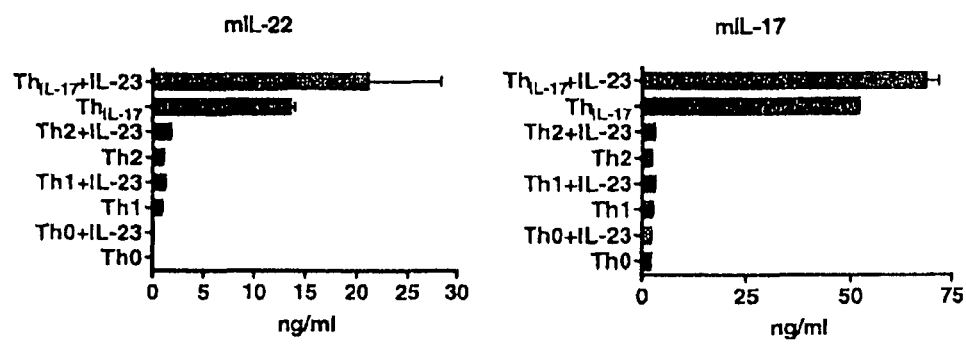
FIG. 34

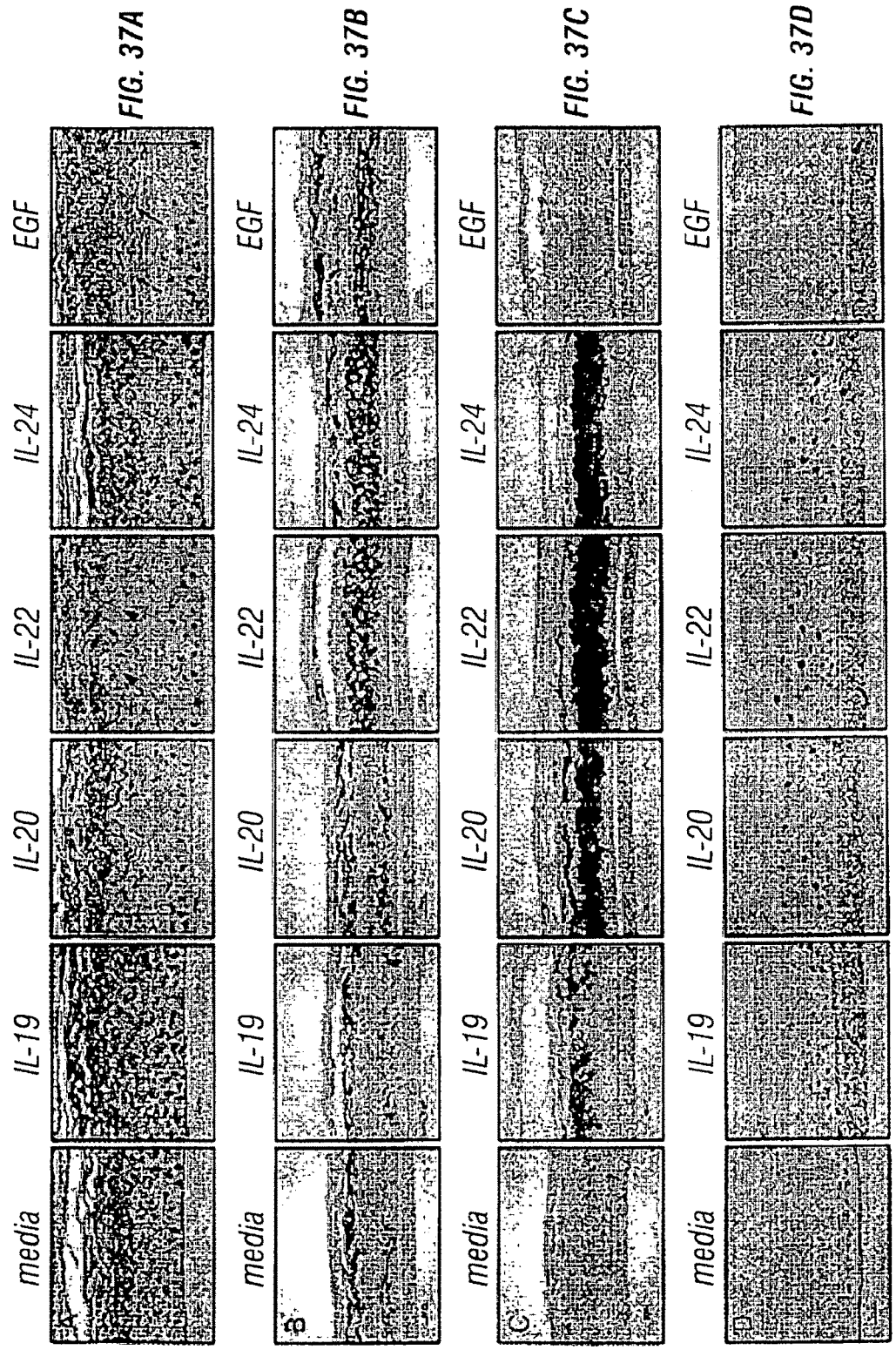

COMPOSITIONS AND METHODS FOR THE TREATMENT OF DISEASES AND DISORDERS ASSOCIATED WITH CYTOKINE SIGNALING

This application is a continuation of U.S. patent application Ser. No. 12/759,496, filed Apr. 13, 2010, now abandoned, which is a divisional of U.S. patent application Ser. No. 11/565,395, filed on Nov. 30, 2006 (now U.S. Pat. No. 7,737,259), which claims the benefit of U.S. Provisional Application No. 60/741,640, filed Dec. 2, 2005, and U.S. Provisional Application No. 60/822,597, filed Aug. 16, 2006, the disclosures of which are incorporated herein by reference in their entirety.

FIELD OF THE INVENTION

The present invention relates to compositions and methods useful for the diagnosis and treatment of diseases and disorders associated with cytokine signaling.

BACKGROUND OF THE INVENTION

Various diseases and disorders are associated with inflammation. Inflammation is a process associated with recruitment of inflammatory cells (e.g., leukocytes) to a site of injury or infection. Inflammation generally protects the body from infection and injury. However, excessive or inappropriate inflammation can have deleterious effects. Autoimmune disorders, for example, often trigger inflammation resulting in the destruction of normal body tissues. Inflammation is also linked to cancer. See, e.g., Coussens et al. (2002) Nature 420:860-867. For example, chronic inflammation associated with inflammatory bowel disease (IBD) is strongly correlated with colon carcinogenesis. During the inflammatory response, certain inflammatory cells produce agents that promote angiogenesis, reduce the anti-tumor activity of cytotoxic T-cells, and induce mutations in DNA, thus creating an environment the promotes tumor progression. Id.

IL-23 is a heterodimeric cytokine that plays a dominant role in autoimmune/inflammatory disorders, and in particular, chronic inflammation. For example, studies in mice have revealed that IL-23 is essential for development of experimental allergic encephalomyelitis (autoimmune inflammation of the brain), which is a model for multiple sclerosis; collagen-induced arthritis, which is a model for rheumatoid arthritis; and delayed-type hypersensitivity. IL-23 also functions to maintain established colitis (a form of IBD). Transgenic expression of IL-23 leads to systemic inflammatory response, and dysregulation of IL-23 leads to eczematous skin disease (an inflammatory skin condition). IL-23 stimulates a unique population of T cells ($Th_{IL-17}$ cells), which in turn induce the production of IL-17 and proinflammatory cytokines. For review of the roles of IL-23 in inflammation and autoimmunity, see, e.g., Hunter (2005) Nat. Rev. Immunol. 5:521-531; and Holscher (2005) Curr. Opin. Invest. Drugs 6:489-495. IL-23 has also been shown to promote tumor growth by increasing angiogenesis and decreasing tumor infiltration by cytotoxic T cells. Langowski et al. (2006) Nature 442:461-465.

SUMMARY OF THE INVENTION

Compositions and methods useful for the diagnosis and treatment of inflammatory disorders and autoimmune disorders (e.g., psoriasis) are provided. Compositions and methods useful for the modulating IL-23 or IL-22 signaling are further provided. These and other embodiments of the invention are provided herein. The present invention is based, in part, on the elucidation of a signaling pathway in which IL-23 acts through IL-22 by inducing IL-22 expression from a recently discovered subset of helper T cells (Th cells), i.e., the $Th_{IL-17}$ lineage.

In one aspect, an antibody that specifically binds to IL-22 is provided, wherein the antibody is (a) an antibody produced by a hybridoma selected from 3F11.3 (ATCC Accession No. PTA-7312), hybridoma 11H4.4 (ATCC Accession No. PTA-7315), and hybridoma 8E11.9 (ATCC Accession No. PTA-7319); (b) an affinity matured form of the antibody of (a); (c) an antigen-binding fragment of the antibody of (a) or (b); or (d) a humanized form of the antibody of (a), (b), or (c).

In another aspect, an antibody that specifically binds to IL-22R is provided, wherein the antibody is (a) an antibody produced by a hybridoma selected from 7E9 (ATCC Accession No. PTA-7313), hybridoma 8A12 (ATCC Accession No. PTA-7318), and hybridoma 8H11 (ATCC Accession No. PTA-7317); (b) an affinity matured form of the antibody of (a); (c) an antigen-binding fragment of the antibody of (a) or (b); or (d) a humanized form of the antibody of (a), (b), or (c).

In another aspect, a method of treating an autoimmune disorder is provided, wherein the autoimmune disorder is not arthritis, the method comprising administering to a mammal an effective amount of a pharmaceutical formulation comprising an antagonist of IL-22. In one such embodiment, the IL-22 antagonist is an antibody that specifically binds IL-22. In one embodiment, the antibody that specifically binds IL-22 is (a) an antibody produced by a hybridoma selected from 3F11.3 (ATCC Accession No. PTA-7312), hybridoma 11H4.4 (ATCC Accession No. PTA-7315), and hybridoma 8E11.9 (ATCC Accession No. PTA-7319); (b) an affinity matured form of the antibody of (a); (c) an antigen-binding fragment of the antibody of (a) or (b); or (d) a humanized form of the antibody of (a), (b), or (c). In one embodiment, the IL-22 antagonist is an antibody that specifically binds IL-22R. In one such embodiment, the antibody that specifically binds IL-22R is (a) an antibody produced by a hybridoma selected from 7E9 (ATCC Accession No. PTA-7313), hybridoma 8A12 (ATCC Accession No. PTA-7318), and hybridoma 8H11 (ATCC Accession No. PTA-7317); (b) an affinity matured form of the antibody of (a); (c) an antigen-binding fragment of the antibody of (a) or (b); or (d) a humanized form of the antibody of (a), (b), or (c). In one embodiment, the IL-22 antagonist is IL-22BP. In one embodiment, the autoimmune disorder is inflammatory bowel disease. In one embodiment, the autoimmune disorder is psoriasis. In one embodiment, the method further comprises administering at least one antibody selected from an antibody that specifically binds IL20Ra, an antibody that specifically binds IL20Rb, and an antibody that specifically binds IL-22R. In one embodiment, the method further comprises administering at least one antibody selected from an antibody that specifically binds IL-22, an antibody that specifically binds IL20Ra, and an antibody that specifically binds IL20Rb.

In another aspect, a method of treating inflammation is provided, wherein the inflammation is not arthritic inflammation, the method comprising administering to a mammal an effective amount of a pharmaceutical formulation comprising an antagonist of IL-22. In one embodiment, the IL-22 antagonist is an antibody that specifically binds IL-22. In one such embodiment, the antibody that specifically binds IL-22 is (a) an antibody produced by a hybridoma selected from 3F11.3 (ATCC Accession No. PTA-7312), hybridoma 11H4.4 (ATCC Accession No. PTA-7315), and hybridoma 8E11.9 (ATCC Accession No. PTA-7319); (b) an affinity matured form of the antibody of (a); (c) an antigen-binding fragment of the antibody of (a) or (b); or (d) a humanized form of the antibody of (a), (b), or (c). In one embodiment, the IL-22 antagonist is an antibody that specifically binds IL-22R. In one such embodiment, the antibody that specifically binds IL-22R is (a) an antibody produced by a hybridoma selected from 7E9 (ATCC Accession No. PTA-7313), hybridoma 8A12 (ATCC Accession No. PTA-7318), and hybridoma 8H11 (ATCC Accession No. PTA-7317); (b) an affinity matured form of the antibody of (a); (c) an antigen-binding fragment of the antibody of (a) or (b); or (d) a humanized form of the antibody of (a), (b), or (c). In one embodiment, the IL-22 antagonist is IL-22BP. In one embodiment, the inflammation is autoimmune inflammation. In one embodiment, the inflammation is skin inflammation. In one embodiment, the inflammation is chronic inflammation.

In another aspect, a method of inhibiting tumor progression is provided, the method comprising administering to a mammal an effective amount of a pharmaceutical formulation comprising an antagonist of IL-22. In one embodiment, the IL-22 antagonist is an antibody that specifically binds IL-22. In one such embodiment, the antibody that specifically binds IL-22 is (a) an antibody produced by a hybridoma selected from 3F11.3 (ATCC Accession No. PTA-7312), hybridoma 11H4.4 (ATCC Accession No. PTA-7315), and hybridoma 8E11.9 (ATCC Accession No. PTA-7319); (b) an affinity matured form of the antibody of (a); (c) an antigen-binding fragment of the antibody of (a) or (b); or (d) a humanized form of the antibody of (a), (b), or (c). In one embodiment, the IL-22 antagonist is an antibody that specifically binds IL-22R. In one such embodiment, the antibody that specifically binds IL-22R is (a) an antibody produced by a hybridoma selected from 7E9 (ATCC Accession No. PTA-7313), hybridoma 8A12 (ATCC Accession No. PTA-7318), and hybridoma 8H11 (ATCC Accession No. PTA-7317); (b) an affinity matured form of the antibody of (a); (c) an antigen-binding fragment of the antibody of (a) or (b); or (d) a humanized form of the antibody of (a), (b), or (c). In one embodiment, the IL-22 antagonist is IL-22BP.

In another aspect, a method of stimulating an IL-23-mediated signaling pathway in a biological system is provided, the method comprising providing an IL-22 agonist to the biological system. In one embodiment, the IL-22 agonist is IL-22. In another aspect, a method of inhibiting an IL-23-mediated signaling pathway in a biological system is provided, the method comprising providing an IL-22 antagonist to the biological system. In one embodiment, the IL-22 antagonist is an antibody that specifically binds IL-22. In one embodiment, the IL-22 antagonist is an antibody that specifically binds IL-22R.

In another aspect, a method of stimulating a $Th_{IL-17}$ cell function is provided, the method comprising exposing a $Th_{IL-17}$ cell to an IL-22 agonist. In one embodiment, the IL-22 agonist is IL-22. In another aspect, a method of inhibiting a $Th_{IL-17}$ cell function is provided, the method comprising exposing a $Th_{IL-17}$ cell to an IL-22 antagonist. In one embodiment, the IL-22 antagonist is an antibody that specifically binds IL-22. In one embodiment, the IL-22 antagonist is an antibody that specifically binds IL-22R.

BRIEF DESCRIPTION OF THE DRAWINGS

FIG. 1 shows a nucleotide sequence (SEQ ID NO:1) of a cDNA encoding a native human IL-22.

FIG. 2 shows the amino acid sequence (SEQ ID NO:2) derived from the coding sequence of SEQ ID NO:1 shown in FIG. 1.

FIG. 3 shows an amino acid sequence (SEQ ID NO:3) of a native human IL-22R.

FIG. 4 shows an amino acid sequence (SEQ ID NO:4) of a native human IL-22BP.

FIG. 5 is a list of all IL-22 antibodies generated and their respective properties, as described in Example 1. Intracellular staining is abbreviated as IC.

FIG. 9 is a calculation of the affinity of anti-IL-22 antibodies for human IL-22, as described in Example 5.

FIG. 10A-H show that anti-IL-22 antibodies detect intracellular expression of IL-22, as described in Example 6 (detecting IL-22 production by intracellular cytokine staining). Top row: permeabilization; bottom row: non-permeabilization.

FIG. 16 shows the testing of anti-IL-22R antibodies on 293 cells expressing IL-22R, as described in Example 11.

FIG. 29A-G shows that treatment with an anti-IL-22 monoclonal antibody significantly reduces IL-23-induced epidermal acanthosis in vivo, as described in Example 20.

FIG. 30A-D shows the strategy used to disrupt the IL-22 gene in mice and evidence confirming that IL-22 expression is absent in IL-22$^{-/-}$ mice, as described in Example 20.

FIG. 33A-B shows that IL-23 induces IL-22 production from various IL-23-activated lymphocytes, as described in Example 21.

FIG. 34A-B shows that IL-22 is a new effector cytokine from the Th$_{IL-17}$ lineage, as described in Example 22.

FIG. 37A-F shows that IL-19, IL-20, IL-22, and IL24 induce epidermal thickening, as described in Example 23.

DETAILED DESCRIPTION OF EMBODIMENTS

I. Definitions

Figure 6:
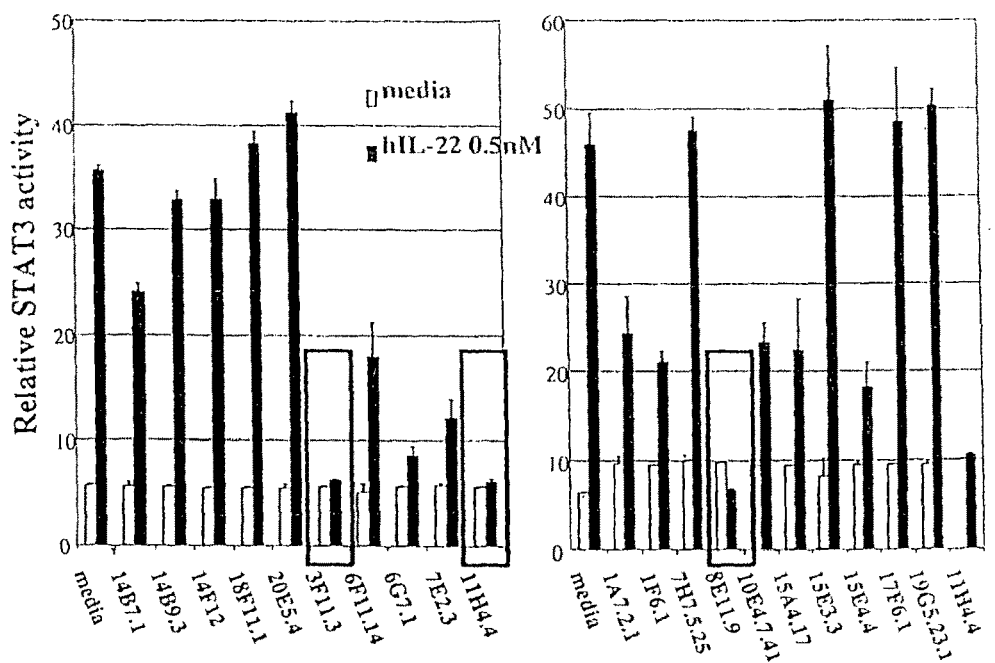
FIG. 6 shows that anti-IL-22 antibodies are able to block STAT3 activation, as described in Example 2.

The term "IL-22 polypeptide" or "IL-22" refers to various interleukin-22 polypeptides (also referred to as "interleukin-22 ligand" or "IL-22L" in the art). The term encompasses native sequence IL-22 polypeptides and variants thereof (which are further defined herein). The IL-22 polypeptides described herein may be isolated from a variety of sources, such as from human tissue or from another source, or prepared by recombinant or synthetic methods. A native IL-22 may be from any species, e.g., murine ("mIL-22") or human ("hIL-22").

The term "IL-22R polypeptide" or "IL-22R" refers to a polypeptide component of an interleukin-22 receptor heterodimer or an interleukin-20 receptor heterodimer. The term encompasses native sequence IL-22R polypeptides and variants thereof (which are further defined herein). The IL-22R polypeptides described herein may be isolated from a variety of sources, such as from human tissue or from another source, or prepared by recombinant or synthetic methods. A native IL-22R may be from any species, e.g., murine ("mIL-22R") or human ("hIL-22R"). Native sequence IL-22R polypeptides are also referred to in the art as "IL-22R1" and "IL22RA."

A "native sequence IL-22 polypeptide" or a "native sequence IL-22R polypeptide" refers to a polypeptide comprising the same amino acid sequence as a corresponding IL-22 or IL-22R polypeptide derived from nature. Such native sequence IL-22 or IL-22R polypeptides can be isolated from nature or can be produced by recombinant or synthetic means. The terms specifically encompass naturally-occurring truncated or secreted forms of the specific IL-22 or IL-22R polypeptide (e.g., an IL-22 lacking its associated signal peptide), naturally-occurring variant forms (e.g., alternatively spliced forms), and naturally-occurring allelic variants of the polypeptide. In various embodiments of the invention, the native sequence IL-22 or IL-22R polypeptides disclosed herein are mature or full-length native sequence polypeptides. FIGS. 2 and 3 show exemplary full length human IL-22 and IL-22R, respectively. A nucleic acid encoding the polypeptide shown in FIG. 2 is shown in FIG. 1. Start and stop codons are shown in bold font and underlined in that figure. While the IL-22 and IL-22R polypeptide sequences disclosed in the accompanying figures are shown to begin with methionine residues designated herein as amino acid position 1, it is conceivable and possible that other methionine residues located either upstream or downstream from the amino acid position 1 in the figures may be employed as the starting amino acid residue for the IL-22 or IL-22R polypeptides.

An "IL-22 variant," an "IL-22R variant," an "IL-22 variant polypeptide," or an "IL-22R variant polypeptide" means an active IL-22 or IL-22R polypeptide as defined above having at least about 80% amino acid sequence identity with a full-length native sequence IL-22 or IL-22R polypeptide sequence. Ordinarily, an IL-22 or IL-22R polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity, and alternatively at least about 99% amino acid sequence identity to a full-length or mature native sequence IL-22 or IL-22R polypeptide sequence.

"Percent (%) amino acid sequence identity," with respect to the IL-22 or IL-22R polypeptide sequences identified herein, is defined as the percentage of amino acid residues in a candidate sequence that are identical with the amino acid residues in a specific IL-22 or IL-22R polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "IL-22 or IL-22R", wherein "IL-22 or IL-22R" represents the amino acid sequence of an IL-22 or IL-22R polypeptide of interest, "Comparison Protein" represents the amino acid sequence of a polypeptide against which the "IL-22 or IL-22R" polypeptide of interest is being compared, and "X", "Y" and "Z" each represent different amino acid residues.

humans and monkeys) and rodents (e.g., mice and rats), unless otherwise indicated. The term encompasses "full-length," unprocessed IL-20 as well as any form of IL-20 that results from processing in the cell. The term also encompasses naturally occurring variants of IL-20, e.g., splice variants, allelic variants, and other isoforms. The term also encompasses fragments or variants of a native IL-20 that maintain at least one biological activity of IL-20.

The term "IL-24" refers to any native IL-24 from any vertebrate source, including mammals such as primates (e.g. humans and monkeys) and rodents (e.g., mice and rats), unless otherwise indicated. The term encompasses "full-length," unprocessed IL-24 as well as any form of IL-24 that results from processing in the cell. The term also encompasses naturally occurring variants of IL-24, e.g., splice variants, allelic variants, and other isoforms. The term also encompasses fragments or variants of a native IL-24 that maintain at least one biological activity of IL-24.

The term "IL-22BP" or "IL-22 binding protein" as used herein refers to any native IL-22BP from any vertebrate source, including mammals such as primates (e.g. humans and monkeys) and rodents (e.g., mice and rats), unless otherwise indicated. The term encompasses "full-length," unprocessed IL-22BP as well as any form of IL-22BP that results from processing in the cell. The term also encompasses naturally occurring variants of IL-22BP, e.g., splice variants, allelic variants, and other isoforms. The term also encompasses fragments or variants of a native IL-22BP that maintain at least one biological activity of IL-22BP. Native IL-22BP is also referred to as "IL-22RA2" in the art.

The term IL-20Ra refers to a polypeptide component of an IL-19 receptor heterodimer or an IL-20 receptor heterodimer. The term encompasses any native IL-20Ra from any vertebrate source, including mammals such as primates (e.g. humans and monkeys) and rodents (e.g., mice and rats), unless otherwise indicated. The term encompasses "full-length," unprocessed IL-20Ra as well as any form of IL-20Ra that results from processing in the cell. The term also encompasses naturally occurring variants of IL-20Ra,

TABLE 2

| IL-22 or IL-22R | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences) divided by (the total number of amino acid residues of the IL-22 or IL-22R polypeptide) = 5 divided by 15 = 33.3%

TABLE 3

| IL-22 or IL-22R | XXXXXXXXXX | (Length =10 amino acids) |
|---|---|---|
| Comparison Protein | XXXXXYYYYYZZYZ | (Length =15 amino acids) |

% amino acid sequence identity = (the number of identically matching amino acid residues between the two polypeptide sequences) divided by (the total number of amino acid residues of the IL-22 or IL-22R polypeptide) = 5 divided by 10 = 50%

The term "IL-19" refers to any native IL-19 from any vertebrate source, including mammals such as primates (e.g. humans and monkeys) and rodents (e.g., mice and rats), unless otherwise indicated. The term encompasses "full-length," unprocessed IL-19 as well as any form of IL-19 that results from processing in the cell. The term also encompasses naturally occurring variants of IL-19, e.g., splice variants, allelic variants, and other isoforms. The term also encompasses fragments or variants of a native IL-19 that maintain at least one biological activity of IL-19.

The term "IL-20" refers to any native IL-20 from any vertebrate source, including mammals such as primates (e.g.

e.g., splice variants, allelic variants, and other isoforms. The term also encompasses fragments or variants of a native IL-20Ra that maintain at least one biological activity of IL-20Ra. Native IL-20Ra is also referred to as "IL-20R1" in the art.

The term IL-20Rb refers to a polypeptide component of an IL-19 receptor heterodimer or an IL-20 receptor heterodimer. The term encompasses any native IL-20Rb from any vertebrate source, including mammals such as primates (e.g. humans and monkeys) and rodents (e.g., mice and rats), unless otherwise indicated. The term encompasses "full-length," unprocessed IL-20Rb as well as any form of IL-20Rb that results from processing in the cell. The term also encompasses naturally occurring variants of IL-20Rb, e.g., splice variants, allelic variants, and other isoforms. The term also encompasses fragments or variants of a native IL-20Rb that maintain at least one biological activity of IL-20Rb. Native IL-20Rb is also referred to as "IL-20R2" in the art.

The term "IL-10R2" refers to a polypeptide component of an IL-22 receptor heterodimer or an IL-20 receptor heterodimer. The term encompasses any native IL-10R2 from any vertebrate source, including mammals such as primates (e.g. humans and monkeys) and rodents (e.g., mice and rats), unless otherwise indicated. The term encompasses "full-length," unprocessed IL-10R2 as well as any form of IL-10R2 that results from processing in the cell. The term also encompasses naturally occurring variants of IL-10R2, e.g., splice variants, allelic variants, and other isoforms. The term also encompasses fragments or variants of a native IL-10R2 that maintain at least one biological activity of IL-10R2. Native IL-10R2 is also referred to as "IL-10Rb" in the art.

An "isolated" biological molecule, such as the various polypeptides, polynucleotides, and antibodies disclosed herein, refers to a biological molecule that has been identified and separated and/or recovered from at least one component of its natural environment.

"Active" or "activity," with reference to IL-22 or IL-22R, refers to a biological and/or an immunological activity of a native IL-22 or IL-22R, wherein "biological" activity refers to a biological function of a native IL-22 or IL-22R other than the ability to induce the production of an antibody against an antigenic epitope possessed by the native IL-22 or IL-22R. An "immunological" activity refers to the ability to induce the production of an antibody against an antigenic epitope possessed by a native IL-22 or IL-22R.

The term "antagonist" is used in the broadest sense, and includes any molecule that partially or fully blocks, inhibits, or neutralizes a biological activity of a polypeptide, such as a native IL-22 or IL-22R polypeptide. Also encompassed by "antagonist" are molecules that fully or partially inhibit the transcription or translation of mRNA encoding the polypeptide. Suitable antagonist molecules include, e.g., antagonist antibodies or antibody fragments; fragments or amino acid sequence variants of a native polypeptide; peptides; antisense oligonucleotides; small organic molecules; and nucleic acids that encode polypeptide antagonists or antagonist antibodies. Reference to "an" antagonist encompasses a single antagonist or a combination of two or more different antagonists.

The term "agonist" is used in the broadest sense and includes any molecule that partially or fully mimics a biological activity of a polypeptide, such as a native IL-22 or IL-22R polypeptide. Also encompassed by "agonist" are molecules that stimulate the transcription or translation of mRNA encoding the polypeptide. Suitable agonist molecules include, e.g., agonist antibodies or antibody fragments; a native polypeptide; fragments or amino acid sequence variants of a native polypeptide; peptides; antisense oligonucleotides; small organic molecules; and nucleic acids that encode polypeptides agonists or antibodies. Reference to "an" agonist encompasses a single agonist or a combination of two or more different agonists.

"Alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of an agent(s) in a continuous mode as opposed to an acute mode, so as to maintain the initial therapeutic effect for an extended period of time. "Intermittent" administration is treatment that is not consecutively done without interruption, but rather is cyclic in nature.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibodies" (Abs) and "immunoglobulins" (Igs) are glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

An antibody that specifically binds to a particular antigen refers to an antibody that is capable of binding the antigen with sufficient affinity such that the antibody is useful as a diagnostic and/or therapeutic agent in targeting the antigen. Preferably, the extent of binding of such an antibody to a non-target polypeptide is less than about 10% of the binding of the antibody to the target antigen as measured, e.g., by a radioimmunoassay (RIA). In certain embodiments, an antibody that binds to a target antigen has a dissociation constant (Kd) of $\leq 1$ µM, $\leq 100$ nM, $\leq 10$ nM, $\leq 1$ nM, or $\leq 0.1$ nM.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO93/1161; Hudson et al. (2003) *Nat. Med.* 9:129-134; and Hollinger et al., Proc. Natl. Acad. Sci. USA 90: 6444-6448 (1993). Triabodies and tetrabodies are also described in Hudson et al. (2003) *Nat. Med.* 9:129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2$^{nd}$ ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced by procedures known in the art. Marks et al. Bio/Technology 10:779-783 (1992) describes affinity maturation by VH and VL domain shuffling. Random mutagenesis of HVR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody, "neutralizing" antibody, or "antagonist" antibody is one which inhibits or reduces a biological activity of the antigen it binds. Such antibodies may substantially or completely inhibit the biological activity of the antigen.

An "agonist antibody," as used herein, is an antibody which partially or fully mimics a biological activity of a polypeptide of interest.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol. Biol.* 293:865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., (1997) *Cancer Res.* 57:4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the Kd or Kd value is measured by surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., (1999) *J. Mol. Biol.* 293:865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

An "on-rate," "rate of association," "association rate," or "$k_{on}$" according to this invention can also be determined as described above using a BIAcore™-2000 or a BIAcore™-3000 system (BIAcore, Inc., Piscataway, N.J.).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to a molecule (such as a nucleic acid, polypeptide, or antibody) so as to generate a "labeled" molecule. The label may be detectable by itself (e.g. radioisotope labels or fluorescent labels) or, in the case of an enzymatic label, may catalyze chemical alteration of a substrate compound or composition, resulting in a detectable product.

By "solid phase" is meant a non-aqueous matrix to which a molecule (such as a nucleic acid, polypeptide, or antibody) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a nucleic acid, polypeptide, antibody, agonist or antagonist) to a mammal. The components of the liposome are commonly arranged in a bilayer formation, similar to the lipid arrangement of biological membranes.

A "small molecule" or "small organic molecule" is defined herein as an organic molecule having a molecular weight below about 500 Daltons.

An "oligopeptide" that binds to a target polypeptide is an oligopeptide that is capable of binding the target polypeptide with sufficient affinity such that the oligopeptide is useful as a diagnostic and/or therapeutic agent in targeting the polypeptide. In certain embodiments, the extent of binding of an oligopeptide to an unrelated, non-target polypeptide is less than about 10% of the binding of the oligopeptide to the target polypeptide as measured, e.g., by a surface plasmon resonance assay. In certain embodiments, an oligopeptide binds to a target polypeptide with a dissociation constant (Kd) of ≤1 µM, ≤100 nM, ≤10 nM, ≤1 nM, or ≤0.1 nM.

An "organic molecule" that binds to a target polypeptide is an organic molecule other than an oligopeptide or antibody as defined herein that is capable of binding a target polypeptide with sufficient affinity such that the organic molecule is useful as a diagnostic and/or therapeutic agent in targeting the polypeptide. In certain embodiments, the extent of binding of an organic molecule to an unrelated, non-target polypeptide is less than about 10% of the binding of the organic molecule to the target polypeptide as measured, e.g., by a surface plasmon resonance assay. In certain embodiments, an organic molecule binds to a target polypeptide with a dissociation constant (Kd) of ≤1 µM, ≤100 nM, ≤10 nM, ≤1 nM, or ≤0.1 nM.

A "biological system" is an in vitro, ex vivo, or in vivo system comprising mammalian cells that share a common signaling pathway.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, and neoplasia.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

As used herein the term "psoriasis" is defined as a condition characterized by the eruption of circumscribed, discreet and confluent, reddish, silvery-scaled macropapules preeminently on the elbows, knees, scalp or trunk.

The term "tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "tumor progression" refers to the growth and/or proliferation of a tumor.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, rectal cancer, gastric cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

An "autoimmune disorder" or "autoimmunity" refers to any condition in which a humoral or cell-mediated immune response is mounted against a body's own tissue. An "IL-23 mediated autoimmune disorder" is any autoimmune disorder that is caused by, maintained, or exacerbated by IL-23 activity.

"Inflammation" refers to the accumulation of leukocytes and the dilation of blood vessels at a site of injury or infection, typically causing pain, swelling, and redness, "Chronic inflammation" refers to inflammation in which the cause of the inflammation persists and is difficult or impossible to remove.

"Autoimmune inflammation" refers to inflammation associated with an autoimmune disorder.

"Arthritic inflammation" refers to inflammation associated with arthritis.

"Inflammatory bowel disease" or "IBD" refers to a chronic disorder characterized by inflammation of the gastrointestinal tract. IBD encompasses ulcerative colitis, which affects the large intestine and/or rectum, and Crohn's disease, which may affect the entire gastrointestinal system but more commonly affects the small intestine (ileum) and possibly the large intestine.

"Arthritis" refers to inflammation of the joints and includes, but is not limited to, osteoarthritis, gout, infection-associated arthritis, Reiter's syndrome arthritis, and arthritis associated with autoimmune disorders, such as rheumatoid arthritis, psoriatic arthritis, lupus-associated arthritis, spondyloarthritis, and scleroderma-associated arthritis.

The term "effective amount" is a concentration or amount of a molecule (e.g., a nucleic acid, polypeptide, agonist, or antagonist) that results in achieving a particular stated purpose. An "effective amount" may be determined empirically. A "therapeutically effective amount" is a concentration or amount of a molecule which is effective for achieving a stated therapeutic effect. This amount may also be determined empirically.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhône-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially a cancer cell overexpressing any of the genes identified herein, either in vitro or in vivo. Thus, a growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995), especially p. 13.

The term "cytokine" is a generic term for proteins released by one cell population which act on another cell population as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "inflammatory cells" designates cells that enhance the inflammatory response such as mononuclear cells, eosinophils, macrophages, and polymorphonuclear neutrophils (PMN).

II. Compositions and Methods of the Invention

A. IL-22 or IL-22R Polynucleotides and Polypeptides

The present invention provides isolated IL-22 or IL-22R polypeptides and isolated nucleotide sequences encoding those polypeptides. IL-22 or IL-22R polypeptides encompass native full-length or mature IL-22 or IL-22R polypeptides as well as IL-22 or IL-22R variants. IL-22 or IL-22R variants can be prepared by introducing appropriate nucleotide changes into the IL-22 or IL-22R DNA, and/or by synthesis of the desired IL-22 or IL-22R polypeptide. Those skilled in the art will appreciate that amino acid changes may alter post-translational processing of the IL-22 or IL-22R, such as changing the number or position of glycosylation sites or altering the membrane anchoring characteristics.

Variations in native IL-22 or IL-22R or in various domains of IL-22 or IL-22R, as described herein, can be made, for example, using any of the techniques and guidelines for conservative and non-conservative mutations set forth, for instance, in U.S. Pat. No. 5,364,934. Variations may be a substitution, deletion or insertion of one or more codons encoding the IL-22 or IL-22R that results in a change in the amino acid sequence of the IL-22 or IL-22R as compared with a native sequence IL-22 or IL-22R. Optionally, the variation is by substitution of at least one amino acid with any other amino acid in one or more domains of the IL-22 or IL-22R. Guidance in determining which amino acid residue may be inserted, substituted or deleted without adversely affecting the desired activity may be found by comparing the sequence of the IL-22 or IL-22R with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |

TABLE 6-continued

| Original Residue | Exemplary Substitutions | Preferred Substitutions |
|---|---|---|
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the IL-22 or IL-22R polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on cloned DNA to produce an IL-22 or IL-22R variant DNA.

IL-22 or IL-22R polypeptide fragments are also provided herein. Such fragments may be truncated at the N-terminus or C-terminus, or may lack internal residues, for example, when compared with a full length native protein. Certain fragments lack amino acid residues that are not essential for a desired biological activity of the IL-22 or IL-22R polypeptide. Accordingly, in certain embodiments, a fragment of IL-22 or IL-22R is biologically active. In certain embodiments, a fragment of full length IL-22 lacks the N-terminal signal peptide sequence. In certain embodiments, a fragment of full-length IL-22R is a soluble form of IL-22R that is not membrane bound, e.g., a form of IL-22R that lacks a transmembrane domain. For example, a soluble form of human IL-22R may lack all or a substantial portion of the transmembrane domain from about amino acids 229-251 of SEQ ID NO:3.

Covalent modifications of IL-22 or IL-22R are included within the scope of this invention. One type of covalent modification includes reacting targeted amino acid residues of an IL-22 or IL-22R polypeptide with an organic derivatizing agent that is capable of reacting with selected side chains or the N- or C-terminal residues of the IL-22 or IL-22R. Derivatization with bifunctional agents is useful, for instance, for crosslinking IL-22 or IL-22R to a water-insoluble support matrix or surface for use in the method for purifying anti-IL-22 or IL-22R antibodies, and vice-versa. Commonly used crosslinking agents include, e.g., 1,1-bis (diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of an IL-22 or IL-22R polypeptide included within the scope of this invention comprises altering the native glycosylation pattern of the polypeptide. "Altering the native glycosylation pattern" is intended for purposes herein to mean deleting one or more carbohydrate moieties found in native sequence IL-22 or IL-22R (either by removing the underlying glycosylation site or by deleting the glycosylation by chemical and/or enzymatic means), and/or adding one or more glycosylation sites that are not present in the native sequence IL-22 or IL-22R. In addition, the phrase includes qualitative changes in the glycosylation of the native proteins, involving a change in the nature and proportions of the various carbohydrate moieties present.

An IL-22 or IL-22R polypeptide of the present invention may also be modified in a way to form a chimeric molecule comprising IL-22 or IL-22R fused to another, heterologous polypeptide or amino acid sequence. In one embodiment, a chimeric molecule comprises a fusion of the IL-22 or IL-22R with a tag polypeptide which provides an epitope to which an anti-tag antibody can selectively bind. The epitope tag is generally placed at the amino- or carboxyl-terminus of the IL-22 or IL-22R. The presence of such epitope-tagged forms of the IL-22 or IL-22R can be detected using an antibody against the tag polypeptide. Also, provision of the epitope tag enables the IL-22 or IL-22R to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an alpha-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In another embodiment, a chimeric molecule may comprise a fusion of an IL-22 or IL-22R polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble form of an IL-22 or IL-22R polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

1. Preparation of IL-22 or IL-22R

IL-22 or IL-22R may be prepared by routine recombinant methods, e.g., culturing cells transformed or transfected with a vector containing a nucleic acid encoding an IL-22 or IL-22R, as exemplified by the nucleic acid shown in FIG. 1, which encodes an IL-22. Host cells comprising any such vector are also provided. By way of example, host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or an Fc region of an immunoglobulin.

It is, of course, contemplated that alternative methods, which are well known in the art, may be employed to prepare IL-22 or IL-22R. For instance, the IL-22 or IL-22R sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the IL-22 or IL-22R may be chemically synthesized separately and combined using chemical or enzymatic methods to produce the full-length IL-22 or IL-22R.

Recombinantly expressed IL-22 or IL-22R may be recovered from culture medium or from host cell lysates. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the IL-22 or IL-22R. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular IL-22 or IL-22R produced.

2. Detection of Gene Expression

Expression of a gene encoding IL-22 or IL-22R can be detected by various methods in the art, e.g., by detecting expression of mRNA encoding IL-22 or IL-22R. As used herein, the term "detecting" encompasses quantitative or qualitative detection. By detecting IL-22 or IL-22R gene expression, one can identify, e.g., those tissues that express an IL-22 or IL-22R gene. Gene expression may be measured using certain methods known to those skilled in the art, e.g., Northern blotting, (Thomas, *Proc. Natl. Acad. Sci. USA*, 77:5201-5205 [1980]); quantitative PCR; or in situ hybridization, using an appropriately labeled probe, based on the sequences provided herein. Alternatively, gene expression may be measured by immunological methods, such as immunohistochemical staining of tissue sections and assay of cell culture or body fluids, to quantitate directly the expression of gene product. Antibodies useful for immunohistochemical staining and/or assay of sample fluids encompass any of the antibodies provided herein. Conveniently, the antibodies may be prepared against a native sequence of an IL-22 or IL-22R polypeptide; against a synthetic peptide comprising a fragment of an IL-22 or IL-22R polypeptide sequence; or against an exogenous sequence fused to an IL-22 or IL-22R polypeptide or fragment thereof (including a synthetic peptide).

B. Antibodies

Antibodies that bind to any of the above- or below-described polypeptides are provided. In one embodiment, an isolated antibody that binds to an IL-19, IL-20, IL-22, IL-24, IL-20Ra, IL-20Rb, IL-10R2, or IL-22R polypeptide. Exemplary antibodies include polyclonal, monoclonal, humanized, human, bispecific, and heteroconjugate antibodies. An antibody may be an antibody fragment, e.g., a Fab, Fab'-SH, Fv, scFv, or (Fab')2 fragment. In one embodiment, an isolated antibody that binds to an IL-22 or IL-22R is provided. In one such embodiment, an antibody partially or completely blocks the activity of an IL-22 or IL-22R polypeptide (i.e., a "blocking" antibody).

Exemplary monoclonal antibodies that bind IL-22 and IL-22R are provided herein and are further described in the Examples. Those antibodies include the anti-IL-22 antibodies designated 3F11.3 ("3F11"), 11H4.4 ("11H4"), and 8E11.9 ("8E11"), and the anti-IL-22R antibodies designated 7E9.10.8 ("7E9"), 8A12.32 ("8A12"), 8H11.32.28 ("8H11"), and 12H5. In one embodiment, a hybridoma that produces any of those antibodies is provided. In one embodiment, monoclonal antibodies that compete with 3F11.3, 11H4.4, or 8E11.9 for binding to IL-22 are provided. In another embodiment, monoclonal antibodies that bind to the same epitope as 3F11.3, 11H4.4, or 8E11.9 are provided. In another embodiment, monoclonal antibodies that compete with 7E9, 8A12, 8H11, or 12H5 for binding to IL-22R are provided. In one embodiment, monoclonal antibodies that bind to the same epitope as 7E9, 8A12, 8H11, or 12H5 are provided. Various embodiments of antibodies are provided below:

1. Polyclonal Antibodies

Antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the polypeptide of interest or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL- TDM adjuvant (monophosphoryl Lipid A, synthetic trehalose dicorynomycolate). The immunization protocol may be selected by one skilled in the art without undue experimentation.

2. Monoclonal Antibodies

Antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the polypeptide of interest or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies that bind to the polypeptide of interest. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. (2001) in *Methods in Molecular Biology* 178:1-37 (O'Brien et al., ed., Human Press, Totowa, N.J.), and in certain embodiments, in Lee et al. (2004) *J. Mol. Biol.* 340:1073-1093.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

3. Monovalent Antibodies

Monovalent antibodies are also provided. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

4. Antibody Fragments

Antibody fragments are also provided. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

5. Humanized Antibodies

Humanized antibodies are also provided. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

6. Human Antibodies

Human antibodies are also provided. Human antibodies can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl.*

*Acad. Sci. USA,* 90: 2551 (1993); Jakobovits et al., *Nature,* 362: 255 (1993); Bruggermann et al., *Year in Immunol.,* 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

7. Bispecific Antibodies

Bispecific antibodies are also provided. Bispecific antibodies are monoclonal antibodies that have binding specificities for at least two different antigens. In certain embodiments, bispecific antibodies are human or humanized antibodies. In certain embodiments, one of the binding specificities is for a polypeptide of interest and the other is for any other antigen. In certain embodiments, bispecific antibodies may bind to two different epitopes of a polypeptide of interest. Bispecific antibodies may also be used to localize cytotoxic agents to cells which express a polypeptide of interest, such a cell surface polypeptide. These antibodies possess a TAT226-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments (e.g. $F(ab')_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature,* 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

8. Multivalent Antibodies

Multivalent antibodies are also provided. A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

9. Single-Domain Antibodies

Single-domain antibodies are also provided. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

10. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science,* 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 6 above under the heading of "preferred substitutions." If such substitutions result in a desirable change in biological activity, then more substantial changes, denominated "exemplary substitutions" in Table 6, or as further described above in reference to amino acid classes, may be introduced and the resulting antibodies screened for the desired binding properties.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312

(Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

In one aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

11. Antibody Derivatives

Antibodies can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In certain embodiments, an antibody may be labeled and/or may be immobilized on a solid support. In a further aspect, an antibody is an anti-idiotypic antibody.

12. Heteroconjugate Antibodies

Heteroconjugate antibodies are also provided. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

13. Cytotoxic Antibodies

Cytotoxic antibodies are also provided. In certain embodiments, a cytotoxic antibody is an anti-IL22 antibody, such as those provided below, which effects an effector function and/or induces cell death. In certain embodiments, a cytotoxic anti-IL-22R antibody binds to the extracellular domain of an IL-22R.

14. Effector Function Engineering

It may be desirable to modify an antibody with respect to effector function, so as to enhance, e.g., the effectiveness of the antibody in treating a disease such as cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

15. Vectors, Host Cells, and Recombinant Methods

For recombinant production of an antibody, in one embodiment, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a) Generating Antibodies Using Prokaryotic Host Cells:

(1) Vector Construction

Polynucleotide sequences encoding polypeptide components of an antibody can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell may be used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

An expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ, 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

(2) Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for *E. coli* growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for *E. coli,* the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J. Biol. Chem.* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance,* 2:63-72 (1996).

In one embodiment, *E. coli* strains deficient for proteolytic enzymes and transformed with plasmids overexpressing one or more chaperone proteins are used as host cells in the expression system of the invention.

(3) Antibody Purification

In one embodiment, an antibody produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) *J. Immunol. Meth.* 62:1-13. The solid phase to which Protein A is immobilized can be a column comprising a glass or silica surface, or a controlled pore glass column or a silicic acid column. In some applications, the column is coated with a reagent, such as glycerol, to possibly prevent nonspecific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

b) Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

(1) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

(2) Origin of Replication

Generally, an origin of replication component is not needed for mammalian expression vectors. For example, the SV40 origin may typically be used only because it contains the early promoter.

(3) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(4) Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

(5) Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

(6) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(7) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(8) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Methods* 62:1-13 (1983)). Protein G is recommended for all mouse isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

C. Immunoconjugates

Immunoconjugates, or "antibody-drug conjugates," are useful for the local delivery of cytotoxic agents in the treatment of cancer. See, e.g., Syrigos et al. (1999) *Anticancer Research* 19:605-614; Niculescu-Duvaz et al. (1997) *Adv. Drug Deliv. Rev.* 26:151-172; U.S. Pat. No. 4,975,278. Immunoconjugates allow for the targeted delivery of a drug moiety to a tumor, whereas systemic administration of unconjugated cytotoxic agents may result in unacceptable levels of toxicity to normal cells as well as the tumor cells sought to be eliminated. See Baldwin et al. (Mar. 15, 1986) *Lancet* pp. 603-05; Thorpe (1985) "Antibody Carriers Of Cytotoxic Agents In Cancer Therapy: A Review," in *Monoclonal Antibodies '84: Biological and Clinical Applications* (A. Pinchera et al., eds.) pp. 475-506.

In one aspect, an immunoconjugate comprises an antibody that binds IL-19, IL-20, IL-22, IL-24, IL22R, IL-20Ra, IL-20Rb, or IL-10R2, such as those provided herein, and a cytotoxic agent, such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent may be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

1. Maytansine and Maytansinoids

In one embodiment, an immunoconjugate comprises an antibody conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

In an attempt to improve their therapeutic index, maytansine and maytansinoids have been conjugated to antibodies that bind to antigens on the surface of tumor cells. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) described immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses 3×10$^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin per antibody would be expected to enhance cytotoxicity over the use of naked antibody. Maytansinoids are well known in the art and can be synthesized using known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Certain coupling agents, including N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP), provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

2. Auristatins and Dolastatins

In some embodiments, an immunoconjugate comprises an antibody conjugated to a dolastatin or dolostatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," US Patent Application Publication No. US 2005-0238649 A1, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lake, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; and Pettit et al (1996) *J. Chem. Soc. Perkin Trans.* 1 5:859-863. See also Doronina (2003) *Nat. Biotechnol.* 21(7):778-784; US Patent Application Publication No. 2005-0238649 A1, hereby incorporated by reference in its entirety (disclosing, e.g., linkers and methods of preparing monomethylvaline compounds such as MMAE and MMAF conjugated to linkers).

3. Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug to which the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

4. Other Cytotoxic Agents

Other antitumor agents that can be conjugated to an antibody include BCNU, streptozoicin, vincristine and 5-fluorouracil, the family of agents known collectively as LL-E33288 complex described in U.S. Pat. Nos. 5,053,394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

In another aspect, an immunoconjugate may comprise an antibody and a compound with nucleolytic activity (e.g., a ribonuclease or a DNA endonuclease such as a deoxyribonuclease; DNase).

For selective destruction of a tumor, an immunoconjugate may comprise an anti-FGFR2 antibody and a highly radioactive atom. A variety of radioactive isotopes are available for the production of radioconjugated anti-FGFR2 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the immunoconjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes other methods in detail.

D. Antagonists and Agonists

Antagonists of IL-22 are provided. Such antagonists encompass those that directly act on IL-22 (e.g., an anti-IL-22 antibody) and those that indirectly affect IL-22 activity (e.g., an anti-IL-22R antibody). Such antagonists are useful, for example, for 1) treating inflammatory disorders and autoimmune disorders, and 2) modulating IL-23 or IL-22 signaling. In one particular embodiment, a composition comprising an antagonist of IL-22 or IL-22R is useful for reducing the amount of psoriatic tissue in a mammal. In another particular embodiment, a composition comprising an antagonist of IL-22 or IL-22R is useful for partially or fully inhibiting tumor cell proliferation.

In one aspect, an antagonist of IL-22 is an anti-IL-22 antibody or an anti-IL-22R antibody. In certain embodiments, an anti-IL-22 antibody is a blocking antibody that fully or partially blocks the interaction of IL-22 with its receptor. In certain embodiments, an anti-IL-22R antibody is a blocking antibody that fully or partially blocks the interaction of IL-22R with IL-22. In certain embodiments, an anti-IL-22R antibody binds to the extracellular ligand binding domain of an IL-22R. For example, an anti-IL-22R antibody may bind to the extracellular ligand binding domain of human IL-22R, which is found in SEQ ID NO:3 from about amino acids 18-228.

In another aspect, an antagonist of IL-22 is an oligopeptide that binds to IL-22 or IL-22R. In one embodiment, an oligopeptide binds to the extracellular ligand binding domain of IL-22R. Oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length. Such oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.,* 81:3998-4002 (1984); Geysen et al., *Proc. Natl. Acad. Sci. USA,* 82:178-182 (1985); Geysen et al., in *Synthetic Peptides as Antigens,* 130-149 (1986); Geysen et al., *J. Immunol. Meth.,* 102:259-274 (1987); Schoofs et al., *J. Immunol.,* 140:611-616 (1988), Cwirla, S. E. et al. (1990) *Proc. Natl. Acad. Sci. USA,* 87:6378; Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc. Natl. Acad. Sci. USA,* 88:8363, and Smith, G. P. (1991) *Current Opin. Biotechnol.,* 2:668). In certain embodiments, an oligopeptide may be conjugated to a cytotoxic agent.

In yet another aspect, an antagonist of IL-22 is an organic molecule that binds to IL-22 or IL-22R, other than an oligopeptide or antibody as described herein. An organic molecule may be, for example, a small molecule. In one embodiment, an organic molecule binds to the extracellular domain of an IL-22R. An organic molecule that binds to IL-22 or IL-22R may be identified and chemically synthesized using known methodology (see, e.g., PCT Publication Nos. WO00/00823 and WO00/39585). Such organic molecules are usually less than about 2000 daltons in size, alternatively less than about 1500, 750, 500, 250 or 200 daltons in size, wherein such organic molecules that are capable of binding to IL-22 or IL-22R may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). In certain embodiments, an organic molecule may be conjugated to a cytotoxic agent.

In yet another aspect, an IL-22 antagonist is a soluble IL-22 receptor, e.g., a form of IL-22R that is not membrane bound. Such soluble forms of IL-22R may compete with membrane-bound IL-22R for binding to IL-22. In certain embodiments, a soluble form of IL-22R may comprise all or a ligand-binding portion of an extracellular domain of IL-22R, e.g., all or a ligand-binding portion of a polypeptide comprising amino acids 18-228 of SEQ ID NO:3. In certain embodiments, a soluble form of IL-22R lacks a transmembrane domain. For example, a soluble form of human IL-22R may lack all or a substantial portion of the transmembrane domain from about amino acids 229-251 of SEQ ID NO:3.

A naturally occurring, soluble receptor for IL-22 has been reported. See Dumoutier L. et al., "Cloning and characterization of IL-22 binding protein, a natural antagonist of IL-10-related T cell-derived inducible factor/IL-22," *J. Immunol.* 166:7090-7095 (2001); and Xu W. et al., "A soluble class II cytokine receptor, IL-22RA2, is a naturally occurring IL-22 antagonist," Proc. Natl. Acad. Sci. U.S.A. 98:9511-9516 (2001). That receptor is variously designated "IL-22BP" or "IL-22RA2" in the art. The sequence of a human IL-22BP is shown in FIG. 4. The term "IL-22BP" or "IL-22 binding protein" as used herein refers to any native IL-22BP from any vertebrate source, including mammals such as primates (e.g. humans and monkeys) and rodents (e.g., mice and rats), unless otherwise indicated.

In yet another aspect, an antagonist of IL-22 is an antisense nucleic acid that decreases expression of the IL-22 or IL-22R gene (i.e., that decreases transcription of the IL-22 or IL-22R gene and/or translation of IL-22 or IL-22R mRNA). In certain embodiments, an antisense nucleic acid binds to a nucleic acid (DNA or RNA) encoding IL-22 or IL-22R. In certain embodiments, an antisense nucleic acid is an oligonucleotide of about 10-30 nucleotides in length (including all points between those endpoints). In certain embodiments, an antisense oligonucleotide comprises a modified sugar-phosphodiester backbones (or other sugar linkages, including phosphorothioate linkages and linkages as described in WO 91/06629), wherein such modified sugar-phosphodiester backbones are resistant to endogenous nucleases. In one embodiment, an antisense nucleic acid is an oligodeoxyribonucleotide, which results in the degradation and/or reduced transcription or translation of mRNA encoding IL-22 or IL-22R. In certain embodiments, an antisense nucleic acid is an RNA that reduces expression of a target nucleic acid by "RNA interference" ("RNAi"). For review of RNAi, see, e.g., Novina et al. (2004) *Nature* 430:161-164. Such RNAs are derived from, for example, short interfering RNAs (siRNAs) and microRNAs. siRNAs, e.g., may be synthesized as double stranded oligoribonucleotides of about 18-26 nucleotides in length. Id.

In yet another aspect, agonists of IL-22 are provided. Exemplary agonists include, but are not limited to, native IL-22 or IL-22R; fragments, variants, or modified forms of IL-22 or IL-22R that retain at least one activity of the native polypeptide; agents that are able to bind to and activate IL-22R; and agents that induce overexpression of IL-22 or IL-22R or nucleic acids encoding IL-22 or IL-22R.

E. Pharmaceutical Formulations

The invention provides pharmaceutical formulations. In one embodiment, a pharmaceutical formulation comprises 1) an active agent, e.g., any of the above-described polypeptides, antibodies, agonists, or antagonists; and 2) a pharmaceutically acceptable carrier. In a further embodiment, a pharmaceutical formulation further comprises at least one additional therapeutic agent.

Pharmaceutical formulations are prepared for storage by mixing an agent having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol (PEG).

Lipofections or liposomes can also be used to deliver an agent into a cell. Where the agent is an antibody fragment, the smallest inhibitory fragment which specifically binds to the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90, 7889-7893 [1993]). Antibodies disclosed herein may also be formulated as immunoliposomes. Liposomes containing an antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of an antibody of the present invention can be conjugated to liposomes as described in Martin et al., *J. Biol. Chem.*, 257: 286-288 (1982) via a disulfide-interchange reaction. A chemotherapeutic agent (such as doxorubicin) is optionally contained within the liposome. See Gabizon et al., *J. National Cancer Inst.*, 81(19): 1484 (1989).

An agent may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations of an agent may be prepared. Suitable examples of sustained-release preparations include semipermeable matrices of solid hydrophobic polymers containing the agent, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

A pharmaceutical formulation herein may also contain more than one active compound as necessary for the particular indication being treated. For example, in one aspect, a pharmaceutical formulation containing more than one active compound comprises 1) at least one antagonist of IL-22, e.g., an antibody that binds to IL-22 and/or an antibody that binds to IL-22R; and 2) at least one antibody that binds to IL-19, IL-20, IL-24, IL20Ra, IL-20Rb, or IL-10R2 (wherein any number of the antibodies listed in 2) may be selected in any combination). In another aspect, a pharmaceutical formulation contains two or more active compounds having complementary activities. For example, in one embodiment, a pharmaceutical formulation may comprise 1) at least one antagonist of IL-22, e.g., an antibody that binds to IL-22 and/or an antibody that binds to IL-22R; and 2) an antagonist of TNF-α or IL-12. In yet another aspect, a pharmaceutical formulation containing more than one active compound may comprise a cytotoxic agent or growth inhibitory agent.

F. Methods of Treatment

Therapeutic methods using any of the above compositions or pharmaceutical formulations are provided. Such methods include in vitro, ex vivo, and in vivo therapeutic methods, unless otherwise indicated. In various aspects, methods of stimulating or inhibiting an IL-23-mediated signaling pathway are provided. Methods of stimulating or inhibiting a $Th_{IL-17}$ cell function are provided. Methods of treating inflammatory and/or autoimmune disorders are also provided. Methods of treating disorders associated with IL-23 or IL-22 signaling are further provided. Methods of treating $Th_{IL-17}$-mediated disorders are also provided. These and other aspects of the invention are provided below.

In one aspect, a method of stimulating an IL-23 mediated signaling pathway in a biological system is provided, the method comprising providing an IL-22 agonist to the biological system. Biological systems include, e.g., mammalian cells in an in vitro cell culture system or in an organism in vivo. Exemplary biological systems that model psoriasis are provided in the Examples and include reconstituted human epidermis (RHE) (Example 14) or animal models (Example 16). In one embodiment, an IL-22 agonist is IL-22. In another aspect, a method of inhibiting an IL-23-mediated signaling pathway in a biological system is provided, the method comprising providing an IL-22 antagonist to the biological system. In one embodiment, the antagonist of IL-22 is an antibody, e.g., a neutralizing anti-IL-22 antibody and/or a neutralizing anti-IL-22R antibody.

In another aspect, a method of stimulating a $Th_{IL-17}$ cell function is provided, the method comprising exposing a $Th_{IL-17}$ cell to an IL-22 agonist. In one embodiment, an IL-22 agonist is IL-22. In another aspect, a method of inhibiting a $Th_{IL-17}$ cell function is provided, the method comprising exposing a $Th_{IL-17}$ cell to an IL-22 antagonist. In one embodiment, the IL-22 antagonist is an antibody, e.g., a neutralizing anti-IL-22 antibody and/or a neutralizing anti-IL-22R antibody. Exemplary $Th_{IL-17}$ cell functions include, but are not limited to, stimulation of cell-mediated immunity (delayed-type hypersensitivity); recruitment of innate immune cells, such as myeloid cells (e.g., monocytes and neutrophils) to sites of inflammation; and stimulation of inflammatory cell infiltration into tissues. In one embodiment, a $Th_{IL-17}$ cell function is mediated by IL-23.

In yet another aspect, a method of treating inflammation is provided, the method comprising administering to a mammal in need of such treatment an effective amount of a pharmaceutical formulation comprising an antagonist of IL-22. In one embodiment, the antagonist of IL-22 is an antibody, e.g., a neutralizing anti-IL-22 antibody and/or a neutralizing anti-IL-22R antibody. Inflammation includes, but is not limited to, autoimmune inflammation (inflammation associated with an autoimmune disorder), chronic inflammation, skin inflammation, arthritic inflammation (including inflammation associated with rheumatoid arthritis), and systemic inflammatory response. In one embodiment, the inflammation is mediated by IL-23.

In yet another aspect, a method of treating an autoimmune disorder is provided, the method comprising administering to a mammal in need of such treatment an effective amount of a pharmaceutical formulation comprising an antagonist of IL-22. In one embodiment, the antagonist of IL-22 is an antibody, e.g., a neutralizing anti-IL-22 antibody and/or a neutralizing anti-IL-22R antibody. Autoimmune disorders include, but are not limited to, connective tissue disease, multiple sclerosis, systemic lupus erythematosus, inflammatory arthritis (e.g., rheumatoid arthritis), autoimmune pulmonary inflammation, Guillain-Barre syndrome, autoimmune thyroiditis, insulin-dependent diabetes mellitus, uveitis, myasthenia gravis, graft-versus-host disease, autoimmune inflammatory eye disease, psoriasis, arthritis associated with autoimmunity (e.g., rheumatoid arthritis), autoimmune inflammation of the brain, and inflammatory bowel disease. In one embodiment, the autoimmune disorder is an IL-23-mediated autoimmune disorder.

In a particular aspect, methods for the treatment of psoriasis and/or disorders characterized by psoriatic symptoms are provided. Psoriasis is considered an autoimmune disease in which T-cells of the immune system recognize a protein in the skin and attack the area where that protein is found, causing the too-rapid growth of new skin cells and painful, elevated, scaly lesions. These lesions are characterized by hyperproliferation of keratinocytes and the accumulation of activated T-cells in the epidermis of the psoriatic lesions. Although the initial molecular cause of disease is unknown, genetic linkages have been mapped to at least 7 psoriasis susceptibility loci (Psor1 on 6p21.3, Psor2 on 17q, Psor3 on 4q, Psor4 on 1 cent-q21, Psor5 on 3q21, Psor6 on 19p13, and Psor7 on 1p). Some of these loci are associated with other autoimmune/inflammatory diseases, including rheumatoid arthritis, atopic dermatitis, and inflammatory bowel disease (IBD). Current approaches to the treatment of psoriasis include the administration of IL-12 or TNF-α antagonists. See, e.g., Nickoloff et al. (2004) *J. Clin. Invest.* 113:1664-1675; Bowcock et al. (2005) *Nat. Rev. Immunol.* 5:699-711; Kauffman et al. (2004) *J. Invest. Dermatol.* 123:1037-1044. The data provided herein, however, implicate a distinct IL-23/IL-22 signaling pathway in the pathogenesis of psoriasis. Accordingly, therapeutics that modulate this signaling pathway may provide an alternative to or may complement other approaches to psoriasis treatment.

In one embodiment, a method of treating psoriasis comprises administering to a patient an effective amount of a pharmaceutical formulation comprising an IL-22 antagonist. In one embodiment, the antagonist of IL-22 is an antibody, e.g., a neutralizing anti-IL-22 antibody and/or a neutralizing anti-IL-22R antibody. In various embodiments, the method further comprises administering (either in the same pharmaceutical formulation or a separate pharmaceutical formulation) at least one additional therapeutic agent. In one such embodiment, the additional therapeutic agent is at least one antagonist of a cytokine selected from IL-19, IL-20, and IL-24. Such antagonists include, but are not limited to, an antibody that binds IL-19, IL-20, IL-24, IL-20Ra, IL-20Rb, or IL-10R2. Any number of such antibodies may be selected in any combination. In another embodiment, the additional therapeutic agent is an agent known to be effective in the treatment of psoriasis. Certain of such therapeutic agents are described, e.g., in Nickoloff et al. (2004) *J. Clin. Invest.* 113:1664-1675; Bowcock et al. (2005) *Nat. Rev. Immunol.* 5:699-711; and Kauffman et al. (2004) *J. Invest. Dermatol.* 123:1037-1044. Such agents include, but are not limited to, a therapeutic agent that targets T cells, e.g., efalizumab and/or alefacept; an antagonist of IL-12, e.g., a blocking antibody that binds IL-12 or its receptor; and an antagonist of TNF-α, e.g., a blocking antibody that binds TNF-α or its receptor.

In yet another aspect, a method of inhibiting tumor progression is provided, the method comprising administering to a mammal an effective amount of a pharmaceutical formulation comprising an antagonist of IL-22. In one embodiment, the antagonist of IL-22 is an antibody, e.g., a neutralizing anti-IL-22 antibody and/or a neutralizing anti-IL-22R antibody. In one embodiment, the tumor progression is IL-23 mediated.

Compositions of the present invention (e.g., polypeptides, antibodies, antagonists, agonists and pharmaceutical formulations comprising any of the foregoing), are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation (intranasal, intrapulmonary) routes. Intravenous or inhaled administration of polypeptides and antibodies is preferred.

In certain embodiments, administration of an anti-cancer agent may be combined with the administration of a composition of the instant invention. For example, a patient to be treated with a composition of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede or follow administration of the composition or may be given simultaneously therewith. Additionally, an anti-estrogen compound such as tamoxifen or an anti-progesterone such as onapristone (see, EP 616812) may be given in dosages known for such molecules.

It may be desirable to also administer antibodies against other immune disease associated- or tumor associated-antigens, such as antibodies that bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. In certain embodiments, it may be beneficial to also administer one or more cytokines to a patient. In certain embodiments, a composition of the invention is coadministered with a growth inhibitory agent. For example, the growth inhibitory agent may be administered before, after, or contemporaneously with administration of the composition. Suitable dosages for the growth inhibitory agent are those presently used and may be lowered due to the combined action (synergy) of the growth inhibitory agent and the composition.

For the treatment or reduction in the severity of an immune disease, the appropriate dosage of a composition of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

For example, depending on the type and severity of a disease, about 1 μg/kg to 15 mg/kg (e.g., 0.1-20 mg/kg) of a polypeptide or antibody is an initial candidate dosage for administration to a patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

G. Diagnostic Methods and Methods of Detection

In one aspect, a method of diagnosing psoriasis in a mammal is provided, the method comprising detecting the level of expression of a gene encoding an IL-22 or IL-22R polypeptide in a test sample of tissue cells obtained from the mammal, wherein a higher expression level in the test sample as compared to a control sample (e.g., a sample of known normal tissue cells of the same cell type) indicates the presence of psoriasis in the mammal from which the test sample was obtained. The detection may be qualitative or quantitative. In one embodiment, the test sample comprises blood or serum. In one embodiment, detecting the level of expression of a gene encoding an IL-22 or IL-22R polypeptide comprises (a) contacting an anti-IL-22 or anti-IL-22R antibody with a test sample obtained from the mammal, and (b) detecting the formation of a complex between the antibody and an IL-22 or IL-22R polypeptide in the test sample. The antibody may be linked to a detectable label. Complex formation can be monitored, for example, by light microscopy, flow cytometry, fluorimetry, or other techniques known in the art. The test sample may be obtained from an individual suspected of having psoriasis.

In one embodiment, detecting the level of expression of a gene encoding an IL-22 or IL-22R polypeptide comprises detecting the level of mRNA transcription from the gene. Levels of mRNA transcription may be detected, either quantitatively or qualitatively, by various methods known to those skilled in the art. Levels of mRNA transcription may also be detected directly or indirectly by detecting levels of cDNA generated from the mRNA. Exemplary methods for detecting levels of mRNA transcription include, but are not limited to, real-time quantitative RT-PCR and hybridization-based assays, including microarray-based assays and filter-based assays such as Northern blots.

In another embodiment, the present invention concerns a diagnostic kit containing an anti-IL-22 or anti-IL-22R antibody in suitable packaging. The kit preferably contains instructions for using the antibody to detect an IL-22 or IL-22R polypeptide. In one aspect, the diagnostic kit is a diagnostic kit for psoriasis.

H. Assays

1. Cell-Based Assays and Animal Models

Cell-based assays and animal models for immune diseases are useful in practicing certain embodiments of the invention. Certain cell-based assays provided in the Examples below are useful, e.g., for testing the efficacy of IL-22 antagonists or agonists.

In vivo animal models are also useful in practicing certain embodiments of the invention. Exemplary animal models are also described in the Examples below. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g., subcutaneous injection, tail vein injection, spleen implantation, intraperitoneal implantation, implantation under the renal capsule, etc.

Graft-versus-host disease models provide a means of assessing T cell reactivity against MHC antigens and minor transplant antigens. Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. A suitable procedure for assessing graft-versus-host disease is described in detail in Current Protocols in Immunology, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 1989, 889-992. A suitable procedure is described in detail in *Current Protocols in Immunology*, above, unit 4.4. Other transplant rejection models which can be used to test the compounds of the invention are the allogeneic heart transplant models described by Tanabe, M. et al, *Transplantation* (1994) 58:23 and Tinubu, S. A. et al, *J. Immunol*. (1994) 4330-4338.

Contact hypersensitivity is a simple in vivo assay for cell mediated immune function (delayed type hypersensitivity). In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S, and Schwarz, T, *Immun. Today* 19 (1): 37-44 (1998).

Additionally, the compositions of the invention can be tested on animal models for psoriasis-like diseases. For example, compositions of the invention can be tested in the scid/scid mouse model described by Schon, M. P. et al, *Nat. Med*. (1997) 3:183, in which the mice demonstrate histopathologic skin lesions resembling psoriasis. Another suitable model is the human skin/scid mouse chimera prepared as described by Nickoloff, B. J. et al, *Am. J. Path*. (1995) 146:580. Another suitable model is described in Boyman et al., *J Exp Med*. (2004) 199(5):731-6, in which human prepsoriatic skin is grafted onto AGR129 mice, leading to the development of psoriatic skin lesions.

Knock out animals can be constructed which have a defective or altered gene encoding a polypeptide identified herein, as a result of homologous recombination between the endogenous gene encoding the polypeptide and a DNA molecule in which that gene has been altered. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

2. Screening Assays for Drug Candidates

Screening assays for drug candidates are designed to identify compounds that bind to or complex with a polypeptide identified herein or a biologically active fragment thereof, or otherwise interfere with the interaction of a polypeptide with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art. All assays are common in that they call for contacting a test compound with a polypeptide identified herein under conditions and for a time sufficient to allow the polypeptide to interact with the test compound.

In binding assays, the interaction is binding and the complex formed can be isolated or detected in the reaction mixture. In a particular embodiment, a polypeptide or the test compound is immobilized on a solid phase, e.g., on a microtiter plate, by covalent or non-covalent attachments. Non-covalent attachment generally is accomplished by coating the solid surface with a solution of the polypeptide or test compound and drying. Alternatively, an immobilized antibody, e.g., a monoclonal antibody specific for a polypeptide to be immobilized, can be used to anchor the polypeptide to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labelled antibody specifically binding the immobilized complex.

If the test compound interacts with but does not bind to a particular polypeptide identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, Nature (London) 340, 245-246 (1989); Chien et al., Proc. Natl. Acad. Sci. USA 88, 9578-9582 (1991)] as disclosed by Chevray and Nathans, Proc. Natl. Acad. Sci. USA 89, 5789-5793 (1991). Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

To identify compounds that interfere with the interaction of a polypeptide identified herein and other intra- or extracellular component(s), a reaction mixture may be prepared containing the polypeptide and the component under conditions allowing for the interaction of the polypeptide with the component. To test the ability of a test compound to inhibit the interaction, the reaction mixture is prepared in the absence and in the presence of the test compound. If there is a decrease in the interaction of the polypeptide with the component in the presence of the test compound, then the test compound is said to inhibit the interaction of the polypeptide with the component.

In certain embodiments, methods for identifying agonists or antagonists of an IL-22 or IL-22R polypeptide comprise contacting an IL-22 or IL-22R polypeptide with a candidate agonist or antagonist molecule and measuring a detectable change in one or more biological activities normally associated with the IL-22 or IL-22R polypeptide. Such activities include, but are not limited to, those described in the Examples below.

3. Antibody Binding Assays

Antibody binding studies may be carried out in any known assay method, such as competitive binding assays, direct and indirect sandwich assays, and immunoprecipitation assays. Zola, Monoclonal Antibodies: A Manual of Techniques, pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Immunohistochemistry may also be used to determine the cellular location of an antigen to which an antibody binds. For immunohistochemistry, the tissue sample may be fresh or frozen or may be embedded in paraffin and fixed with a preservative such as formalin, for example.

Articles of Manufacture

In another aspect, an article of manufacture comprising compositions useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide, an antibody, an agonist, or an antagonist of the invention. An instruction or label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

In one embodiment, the invention provides an article of manufacture, comprising:

(a) a composition of matter comprising an agonist or antagonist of IL-22 or IL-22R;

(b) a container containing said composition; and (c) a label affixed to said container, or a package insert included in said container, referring to the use of said antagonist in the treatment of an immune-related disease or cancer. The composition may comprise an effective amount of the antagonist.

The following examples are offered for illustrative purposes only, and are not intended to limit the scope of the present invention in any way.

All patent and literature references cited in the present specification are hereby incorporated by reference in their entirety.

III. Examples

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Generation of Anti-IL-22 and Anti-IL-22R Antibodies

This example illustrates preparation of monoclonal antibodies that specifically bind IL-22 or IL-22R. Techniques employed for producing the monoclonal antibodies were based on those known in the art and are described, for instance, in Goding, supra. Immunogens employed were full length purified human IL-22 (hIL-22) or full length purified human IL-22R (hIL-22R). Briefly, mice were immunized with about 1-100 micrograms of the hIL-22 or hIL-22R immunogen emulsified in adjuvant. The immunized mice were then boosted 10 to 12 days later with additional immunogen emulsified in adjuvant. Serum samples were periodically obtained from the mice for testing in ELISA assays to detect anti-IL-22 or IL-22R antibodies.

After a suitable antibody titer was detected, the animals "positive" for antibodies were sacrificed and the spleen cells harvested. The spleen cells were then fused (using 35% polyethylene glycol) to a murine myeloma cell line. The fusions generated hybridoma cells which were cloned and cultured in medium containing HAT (hypoxanthine, aminopterin, and thymidine). The hybridoma cells were screened in an ELISA for reactivity against IL-22 or IL-22R. (See FIG. 5.) A listing of the antibodies produced by those hybridomas and their respective properties is found in FIG. 5.

Example 2

IL-22 Signaling is Blocked by Anti-IL-22 Antibodies

STAT3 activation is a hallmark of IL-22 receptor activation and intracellular signaling. Antibodies generated against human IL-22 were tested for the ability to block IL-22-induced STAT3 activation. 293 T cells expressing the human IL-22 receptor heterodimer (hIL-22R/hIL-10R2) were plated at 0.2×10^6/well in a 24 well plate. Cells were transfected with a STAT3 Luciferase reporter (TK-SIE-SRE-S) using Lipofectamine 2000™ (Invitrogen). Therefore, when STAT3 is activated, the cells will produce luciferase, an enzymatic activity that can be detected by the addition of luciferin. A reduction of luciferase activity means that STAT3 is blocked. The next day 0.5 nM of hIL-22 (R&D Systems) was added to each well along with 20 µg/ml of antibody. Sixteen hours later the cells were lysed and samples read on a luminometer. Data shown in FIG. 6 is luciferase activity relative to *Renilla* internal control, which is a measure of relative STAT3 activation. As shown in FIG. 6, the antibodies 3F11.3, 11H4.4, and 8E11.9 had significant blocking ability.

Example 3

Dose Versus Response of Anti-IL-22 Antibodies

Figure 7:
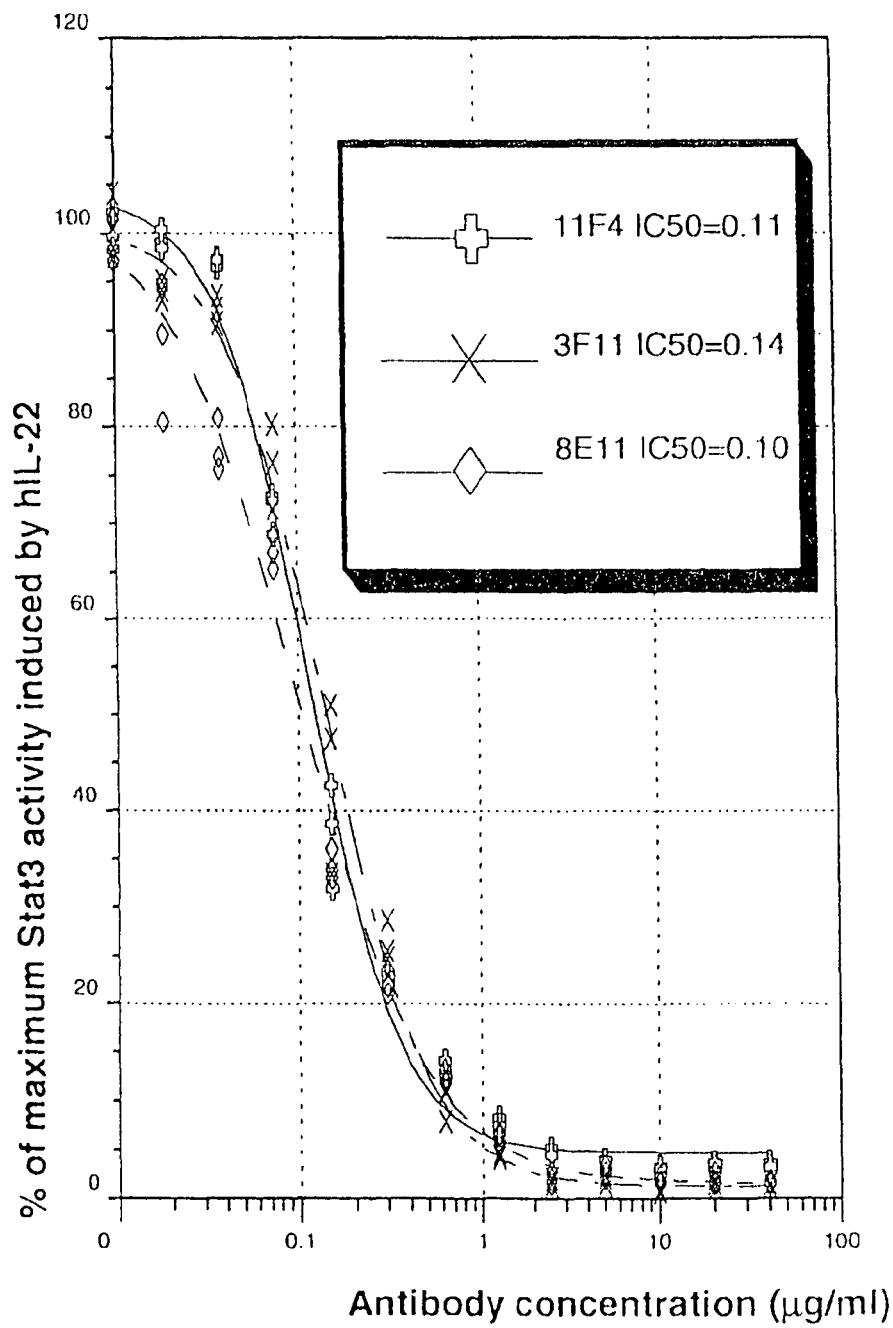
FIG. 7 shows that three specific anti-IL-22 antibodies block human IL-22 in a dose dependent manner, as described in Example 3.

A dose range of antibodies generated against human IL-22 were tested for the ability to block human IL-22 in a STAT3 activation assay. 293 cells expressing hIL-22R/hIL-10R2 were plated at 0.2×10^6/well in a 24 well plate. Cells were transfected with a STAT3 Luciferase reporter (TK-SIE-SRE-S) using Lipofectamine 2000™ (Invitrogen). The next day 0.5 nM of hIL-22 (R&D Systems) was added to each well along with varying concentrations of the anti-IL-22 antibodies 3F11, 8E11 or 11H4. The concentration range for the antibody began at 40 µg/ml with 2-fold dilutions to a final concentration of 0.012 µg/ml. Sixteen hours later the cells were lysed and samples read on a luminometer. The three antibodies show a similar dose/response curve for blocking STAT3 activation, as shown in FIG. 7.

Example 4

Dose Versus Response of Anti-IL-22 Antibodies

Figure 8:
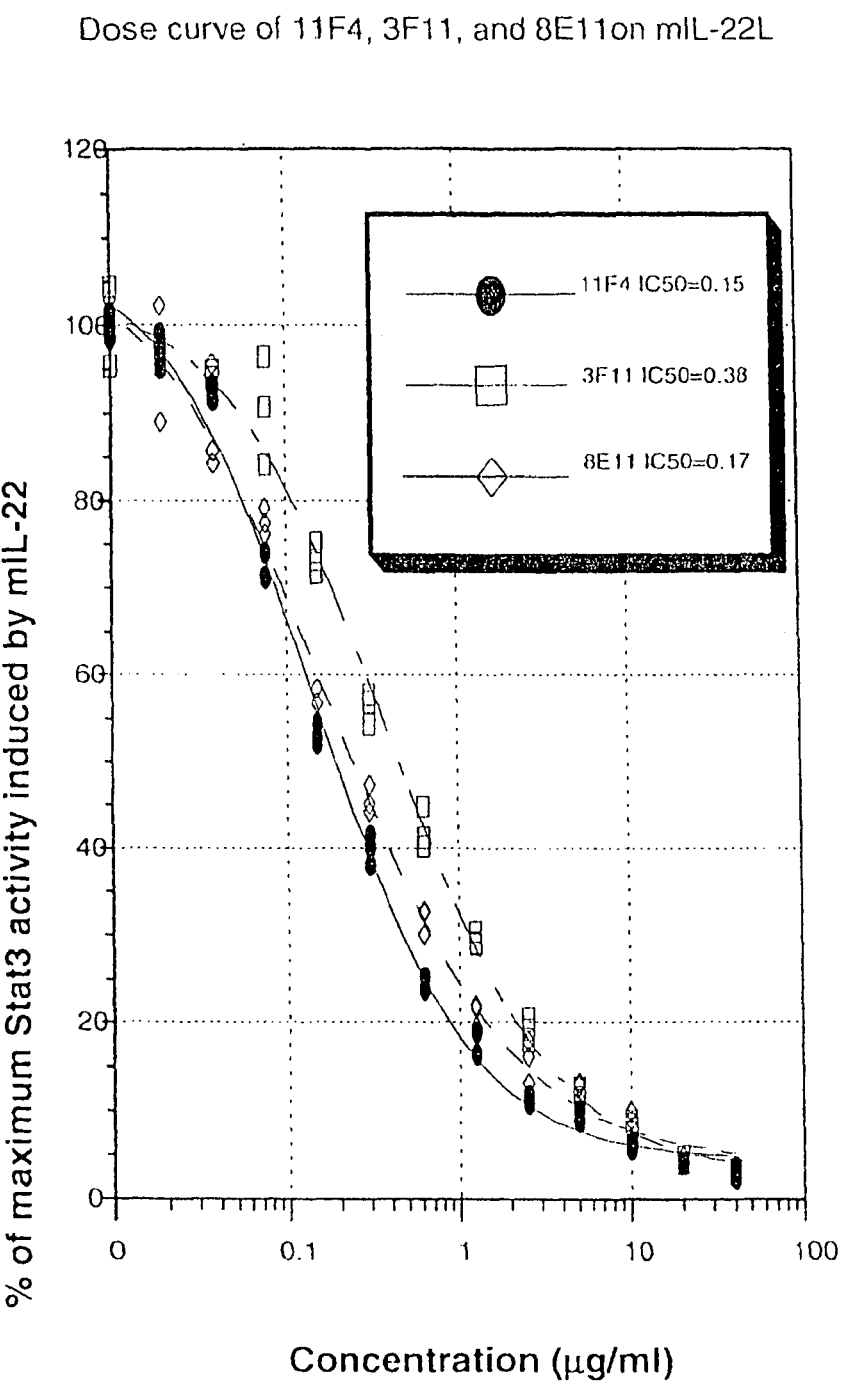
FIG. 8 shows that three specific anti-IL-22 antibodies are able to block murine IL-22 in a dose dependent manner, as described in Example 4.

A dose range of antibodies generated against human IL-22 were tested for the ability to block murine IL-22 (mIL-22) in a STAT3 activation assay. 293 cells expressing mIL-22R/mL-10Rb were plated at 0.2×10^6/well in a 24 well plate. Cells were transfected with a STAT3 Luciferase reporter (TK-SIE-SRE-S) using Lipofectamine 2000™ (Invitrogen). The next day 0.5 nM of mIL-22 (polyhistidine tagged) was added to each well along with varying concentrations of 3F11, 8E11 or 11H4 antibody. The concentration range for the antibody started at 40 µg/ml with 2-fold dilutions to 0.012 µg/ml. Sixteen hours later the cells were lysed and samples read on a luminometer. FIG. 8 shows that the anti-IL-22 antibodies cross-reacted with murine IL-22 and showed a similar, but not as robust, dose/response curve. This shows that the anti-IL-22 antibodies can be used in murine experiments.

Example 5

Affinity of Anti-IL-22 for Human IL-22

FIG. 9 shows the affinity of anti-IL-22 for human IL-22. The affinity was measured by BIACore analysis. Various amounts of anti-IL-22 IgGs were immobilized on a CM 5 chip (845 RU (reference units) for 11H4 IgG, 1933 RU for 8E11 IgG, & 7914 RU for 3F11 IgG) via N-ethyl-N'-(3-dimethylaminopropyl)-carbodiimide hydrochloride (EDC) and N-hydroxysuccinimide (NHS) coupling chemistry. Two-fold serial dilutions of IL-22 were prepared covering the range of 0.5-250 nM. The antigen samples were injected over the IgG-immobilized surface at a flow rate of 20 µl/min for 6 minutes, and the bound complexes were allowed to dissociate for 10 minutes. The IgG surfaces were regenerated with 10 mM Gly, pH 1.5 after each round of antigen injection. As a negative control flow cell, an irrelevant IgG (3A5 RF graft) was immobilized for background response subtraction. The running buffer, PBS containing 0.05%

Tween 20 with 0.01% NaN3 was used for all sample dilutions and the binding experiment was done at 25° C. The data was analyzed by global fitting with a 1:1 binding model. These results show that the anti-IL-22 antibodies have very good affinity for human IL-22.

Example 6

Anti-IL-22 Antibodies Detect IL-22 in the Cell

Antibodies against IL-22 were tested for the ability to detect intracellular IL-22.

For intracellular FACS staining of IL-22, the following 293 cell lines were used: Cells expressing hIL-22-GFP, mIL-22-GFP, mIL20-GFP, and GFP only. The antibodies tested were anti-human IL-22 antibodies 3F11, 8E11, and 17F6. Mouse anti-gp120 was used as an isotype control. The secondary antibody used was anti-mouse IgG-PE from Jackson labs. Cells were incubated with Brefeldin A for 2 hours, washed in PBS, and then fixed with 2% paraformaldehyde overnight at 4° C. Cells were then washed in PBS, and incubated in 5 ml 0.2% Tween-20 for 30 minutes at 37° C. Antibody staining was carried out for 30 minutes at 4° C., then washed with Tween-20 solution. Cells were resuspended in FACS buffer and analyzed on a FACScan. FIG. 10A-10H shows the FACS results. The FACS results show that antibodies 3F11 and 8E11 cause a shift in the cell staining pattern, indicating that these antibodies bind both murine and human intracellular IL-22.

Figure 11:
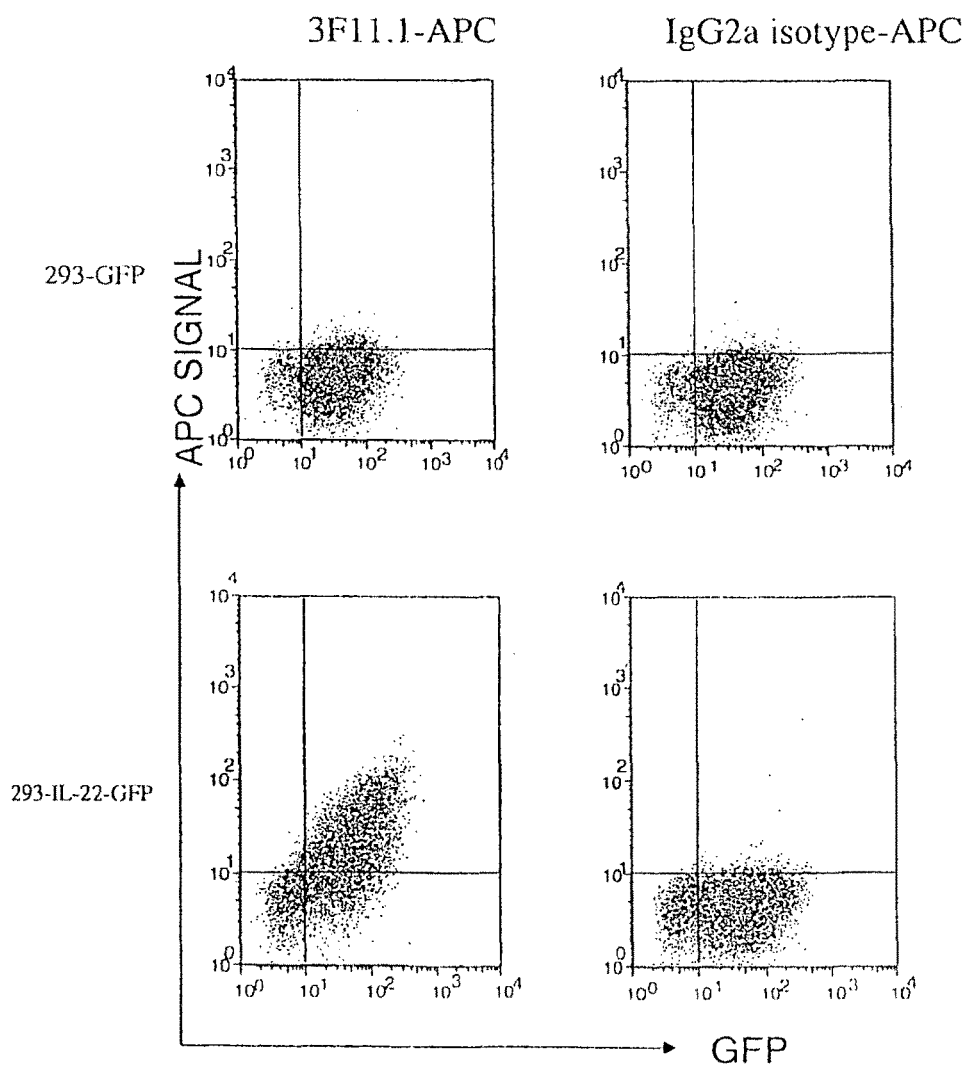
FIG. 11 shows intracellular FACS staining for IL-22 using labeled anti-IL-22 antibodies, as described in Example 6.

The anti-IL-22 antibody 3F11 was used in additional cell staining experiments. The 3F11 antibody was conjugated with Alexa 647, a phycoerythrin fluorophore. Mouse IgG2a conjugated to Alexa 647 was used as an isotype control (Caltag). 293 cell lines expressing hIL-22-GFP and GFP only were assayed for 3F11 antibody binding. The 293 cells were fixed with 2% paraformaldehyde for 30 minutes, then washed twice with PBS/2% FCS. Cells were resuspended in 0.5% saponin for 15 minutes. Normal mouse serum was added for another 15 minutes, then antibodies were added at 0.5 µg/million cells for 30 minutes. Cells were washed and resuspended in FACS buffer and analyzed on a FACScan. FIG. 11 shows in the lower left panel a shift in cells into the upper right quadrant. This result indicates that the conjugated 3F11 antibody is binding to intracellular IL-22.

Example 7

Expression of IL-22 in Th1 Tcells

When CD4+ T cells mature from thymus and enter into the peripheral lymph system, they generally maintain their naïve phenotype before encountering antigens specific for their T cell receptor (TCR) [Sprent et al., *Annu Rev Immunol*. (2002); 20:551-79]. The binding of the TCR to specific antigens presented by antigen-presenting cells (APC), causes T cell activation. Depending on the environment and cytokine stimulation, CD4+ T cells can differentiate into a Th1 or Th2 phenotype and become effector or memory cells [Sprent et al., *Annu Rev Immunol*. (2002); 20:551-79 and Murphy et al., *Nat Rev Immunol*. (2002) December; 2(12): 933-44]. This process is known as primary activation. Having undergone primary activation, CD4+ T cells become effector or memory cells, and they maintain their phenotype as Th1 or Th2. Once these cells encounter antigen again, they undergo secondary activation, but this time the response to antigen will be quicker than the primary activation and results in the production of effector cytokines as determined by the primary activation [Sprent et al., *Annu Rev Immunol*. (2002); 20:551-79 and Murphy et al., *Annu Rev Immunol*. 2000; 18:451-94]. Studies have found during the primary and secondary activation of CD4+ T cells the expression of certain genes is variable [Rogge et al., *Nature Genetics*. 25, 96-101 (2000) and Ouyang et al., *Proc Natl Acad Sci USA*. (1999) March 30; 96(7):3888-93].

For primary activation conditions, naïve T cells may be activated by Ova and APC. RNA isolated from cells in this condition can provide information about what genes are differentially regulated during the primary activation, and what cytokines affect gene expression during Th1 and Th2 development. After primary activation, the CD4+ T cells may be maintained in culture. As the previous activation and cytokine treatment has been imprinted into these cells, they have become either effector or memory cells. During this period, because there are no APCs or antigens, the CD4+ T cells enter a resting stage. This resting stage provides information about the differences between naïve vs. memory cells, and resting memory Th1 vs. resting memory Th2 cells. The resting memory Th1 and Th2 cells then undergo secondary activation with anti-CD3/CD28 antibodies or stimulation with IL12/IL18 cytokines. These conditions provide information about the differences between activated naïve and activated memory T cells, and the differences between activated memory Th1 vs. activated memory Th2 cells.

Figure 12:
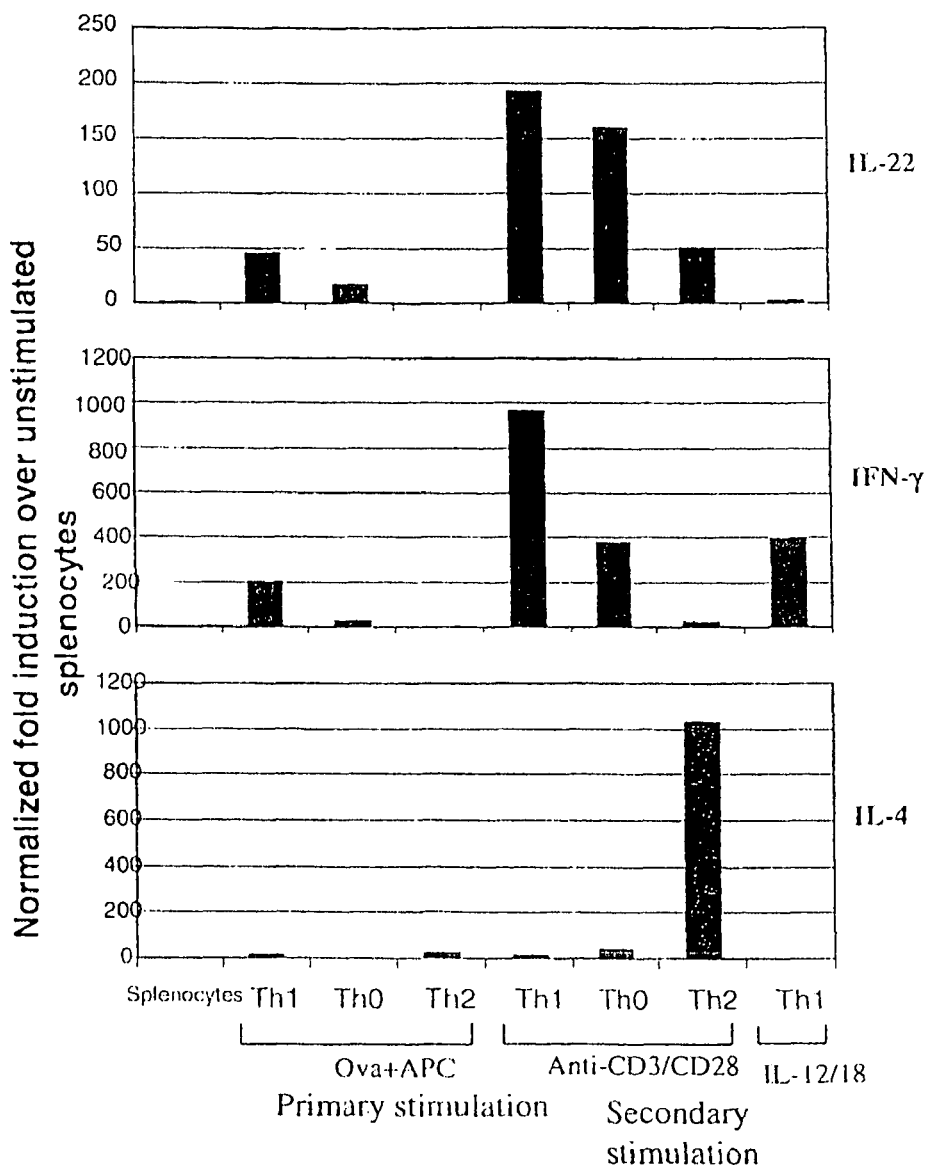
FIG. 12 shows expression of IL-22 in murine Th1 cells as determined by 5' nuclease analysis, as described in Example 7.

For the experiment shown in FIG. 12, splenocytes from DO11.10 mice were isolated and activated by OVA in either Th1 conditions: [IL-12 (1 ng/ml), IFN-γ, and IL-4 (1 µ/ml)]; Th0 conditions: [(anti-IL12, anti-IFN-γ, and anti-IL4)]; or Th2 conditions: [(anti-IL-12 (0.5 µg/ml), anti-IFN-γ, and IL-4 (5 ng/ml)]. RNA was harvested 48 hrs later (primary stimulation). The rest of the cells were maintained in the culture until day 7, and then re-stimulated (secondary stimulation) by OVA and irradiated Balb/c splenocytes. A subset of the cells from Th1 condition were also stimulated by IL-12 and IL-18 alone. 48 hrs later RNA was harvested. The expression of IL-22, IFN-γ, and IL-4 in these RNA samples were analyzed by 5' nuclease (TaqMan™) analysis. The expression was first normalized against house keeping gene HPRT probes, then graphed as fold increase compared with the expression level from splenocytes. The result in shown in FIG. 12, and the data shows that IL-22 is highly expressed in Th1 cells upon secondary stimulation. Therefore anti-IL-22 therapeutics would be useful in targeting these cells, either for treatment of Th1 mediated disorders when it would be desirable to clear Th1 cells from the blood or as a diagnostic for Th1 mediated disorders when IL-22 is suspected to play a role.

Example 8

IL-22 is Produced by γδ T Cells

Figure 13:
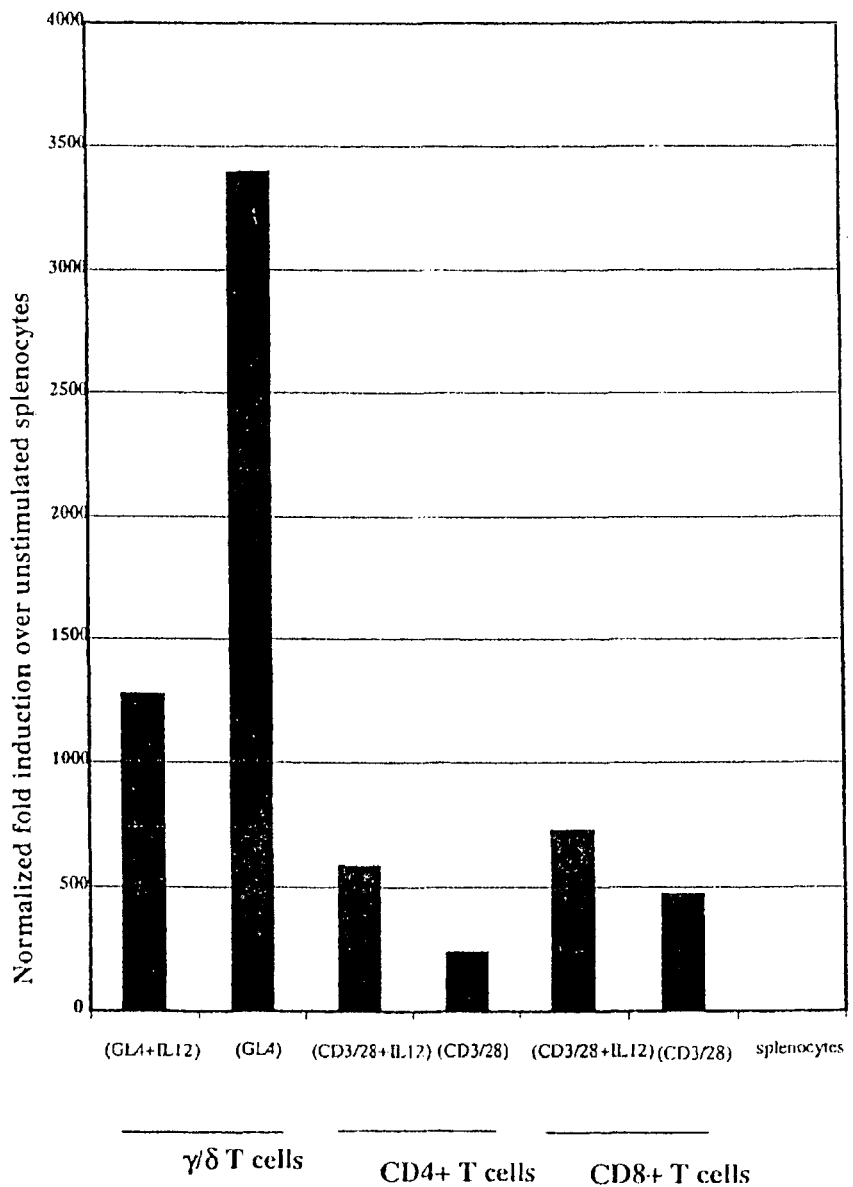
FIG. 13 shows expression of IL-22 in murine γδ T cells as determined by 5' nuclease analysis, as described in Example 8.

To analyze expression of IL-22 in γδ T cells, cells were isolated from mouse spleen and γδ T cells were separated by MACS sorting. GL4 is an anti-γδ TCR antibody which specifically activates γδ T cells (Becton-Dickenson) Qiagen MINI RNA isolation kit was used to isolate RNA from the cells for 5' nuclease (TaqMan™) analysis. Master Mix one-step RT-PCR Master Mix Reagent (Applied Biosystems; 4309169) was used and the housekeeping genes RPL10 and SPF31 were used for normalization. Whole splenocytes were used to determine the relative level of expression of IL-22. FIG. 13 shows that IL-22 is highly expressed in γδ T cells stimulated with GL4 antibody.

Example 9

IL-22 is Produced by Activated Human T Cells

Nucleic acid microarrays are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (in this instance, activated CD4+ T cells) sample is greater than hybridization signal of a probe from a control (in this instance, non-stimulated CD4+ T cells) sample, the gene or genes overexpressed in the test tissue are identified. The implication of this result is that an overexpressed protein in a test tissue is useful not only as a diagnostic marker for the presence of the disease condition, but also as a therapeutic target for treatment of the disease condition.

The methodology of hybridization of nucleic acids and microarray technology is well known in the art. For example, the specific preparation of nucleic acids for hybridization and probes, slides, and hybridization conditions are all detailed in PCT Patent Application Serial No. PCT/US01/10482, filed on Mar. 30, 2001, and which is herein incorporated by reference.

In this experiment, CD4+ T cells were purified from a single donor using the RossetteSep™ protocol from Stem Cell Technologies (Vancouver BC) which uses anti-CD8, anti-CD16, anti-CD19, anti-CD36 and anti-CD56 antibodies used to isolate CD4+ T cells. Isolated CD4+ T cells were activated with an anti-CD3 antibody (used at a concentration that does not stimulate proliferation) together with either ICAM-1 or anti-CD28 antibody. At 24 or 72 hours cells were harvested, RNA extracted and analysis run on Affimax (Affymetrix Inc., Santa Clara, Calif.) microarray chips. Non-stimulated (resting) cells were harvested immediately after purification, and subjected to the same analysis. Genes were compared whose expression was upregulated at either of the two timepoints in activated vs. resting cells.

Figure 14A:
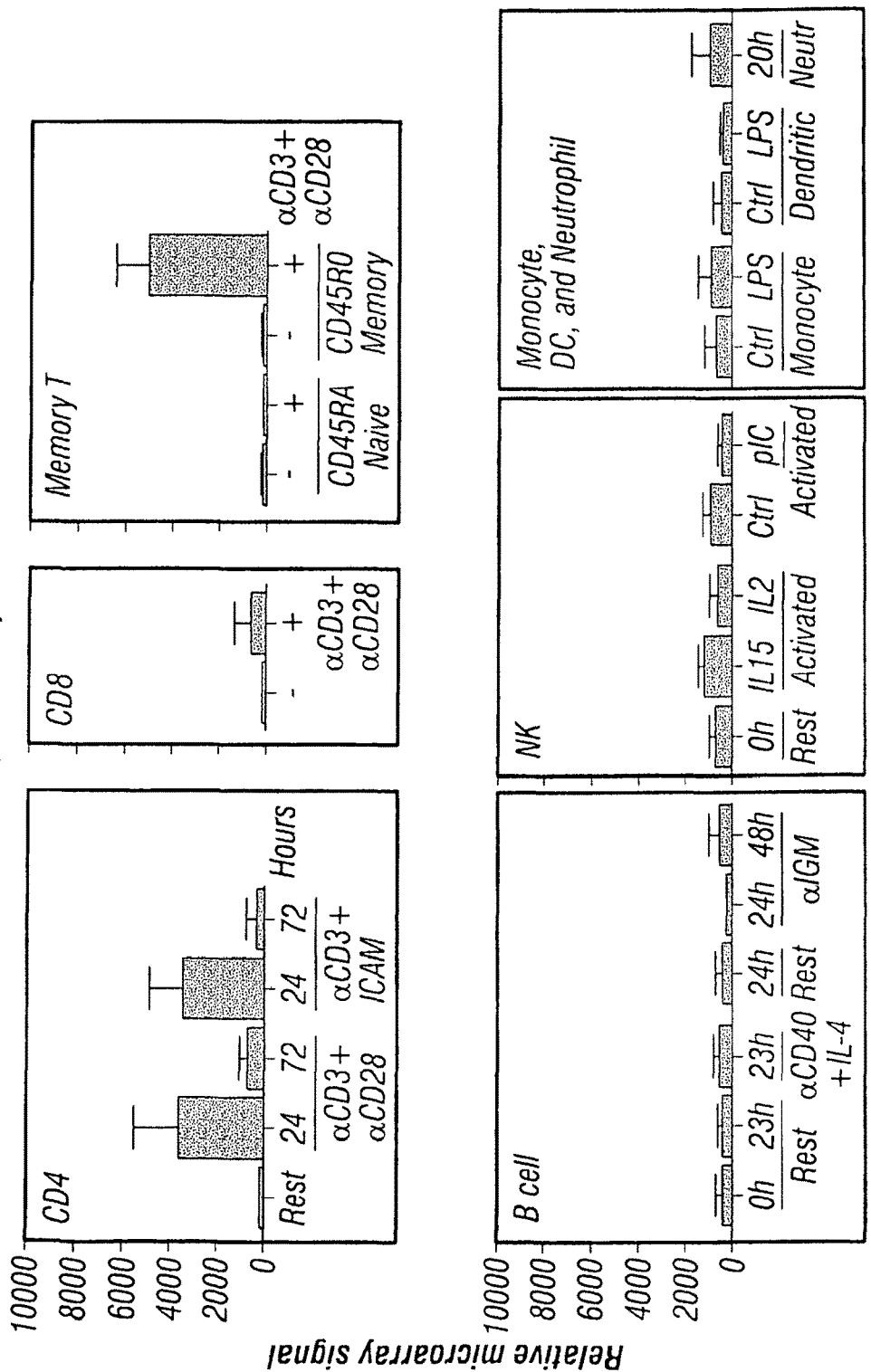
FIG. 14A-C show expression of IL-22 in activated human T cells as determined by microarray analysis, as described in Example 9 (IL-22 is produced by activated human T cells). A-C: left axis corresponds to Relative microarray signal.
Figure 14B:
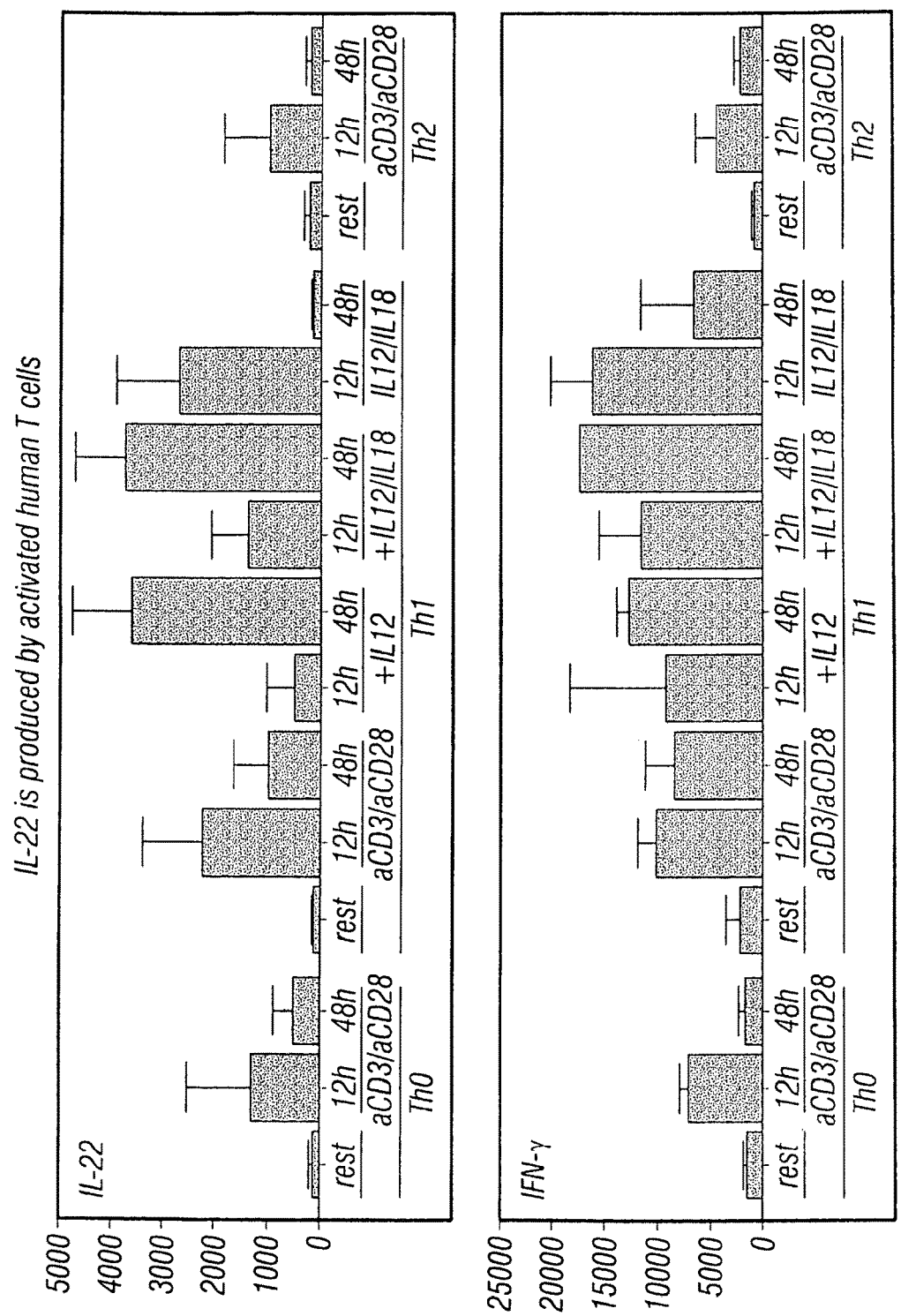
Figure 14C:
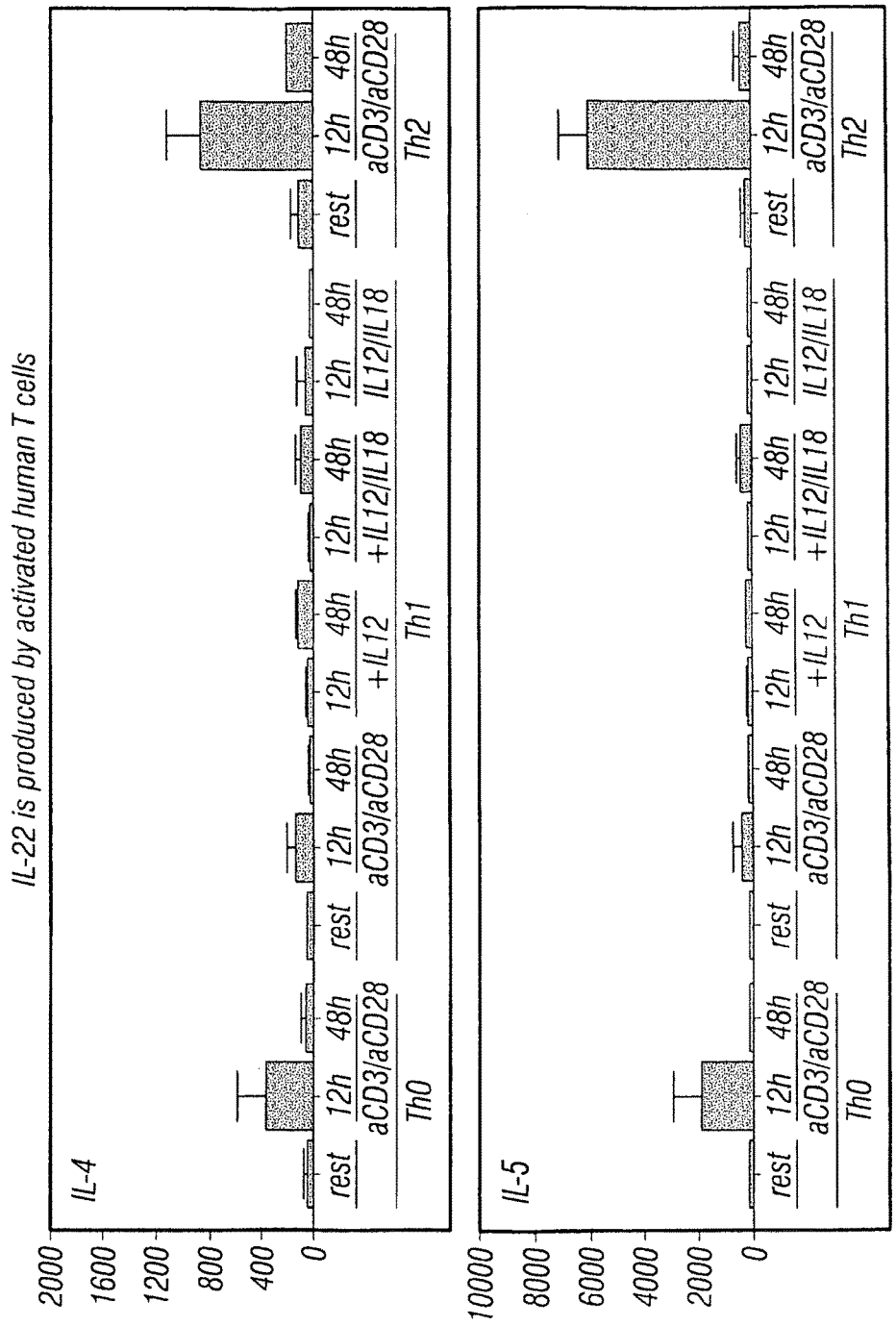

The results of this experiment are shown in FIG. 14A-C. The microarray results support and compliment the data in Example 7. The Th1 T cells produce a large amount of IL-22 when stimulated, as opposed to the Th2 cells which produce IL-4 or IL-5. This result would allow separation of Th1 and Th2 related immune disorders based on the cytokine profile. Th1 cells expressing IL-22 and IFN-γ could be treated by therapeutics directed to these cytokines, without affecting the Th2 cell population.

Example 10

Th1 Cells Express Intracellular IL-22

Figure 15A:
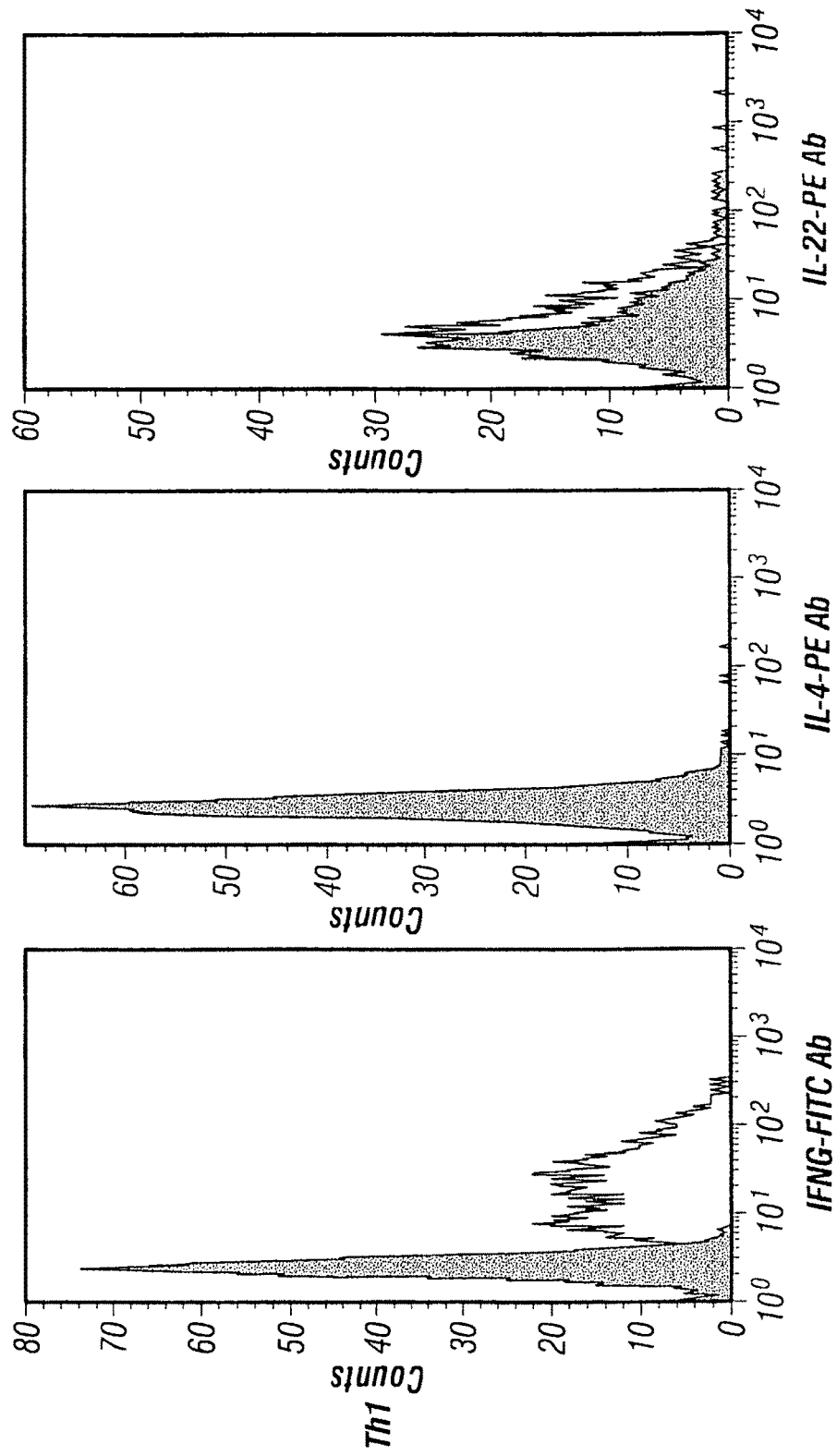
FIG. 15A-B shows the expression level of IL-22 in T cells by FACS, as described in Example 10 (detecting IL-22 production from primary Th1 cells by intracellular staining).
Figure 15B:
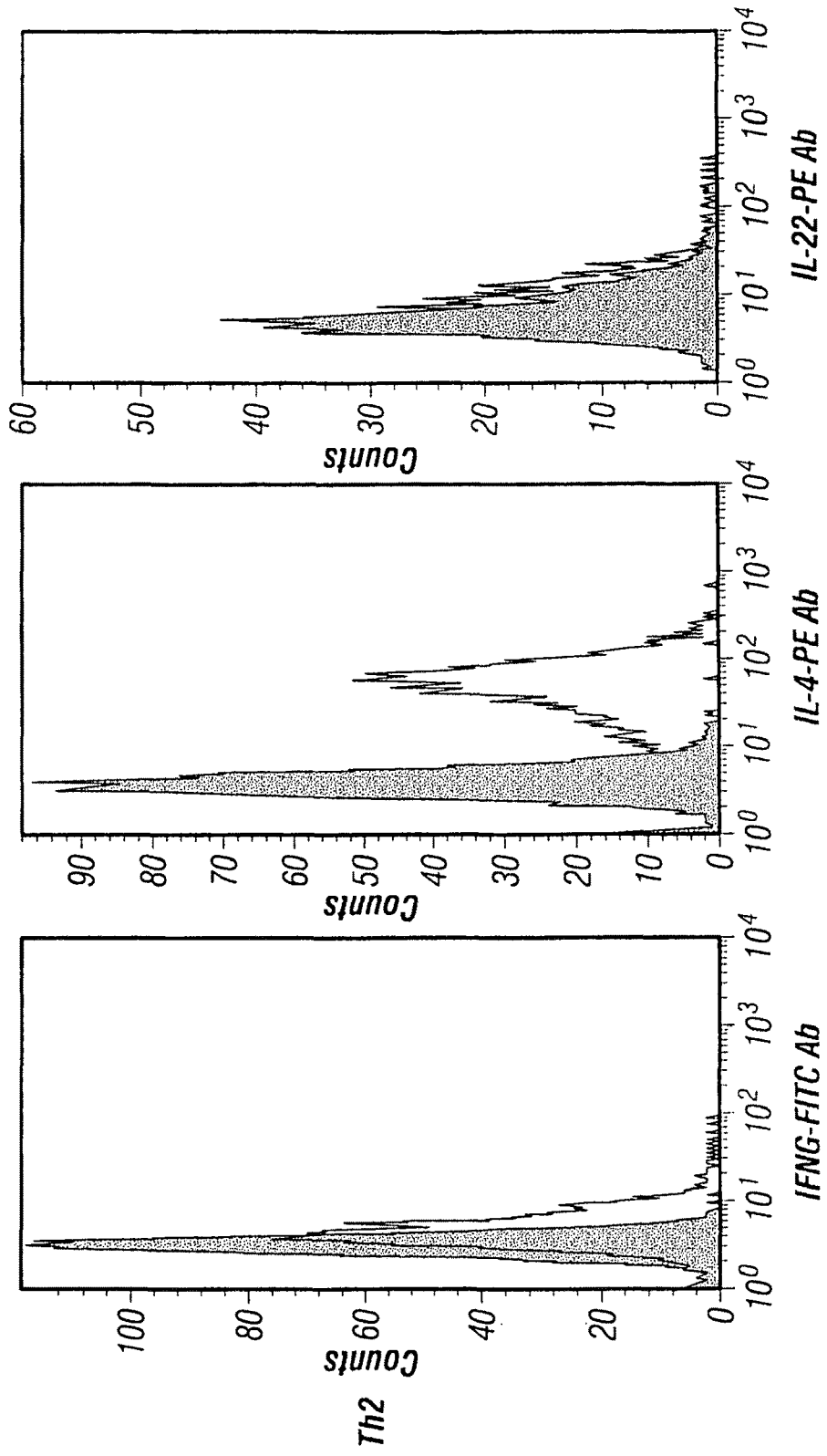

To determine the expression level of IL-22 in T cells by FACS, intracellular staining was carried out on murine Th1/Th2 cells. Primary splenocytes were polarized to Th1 or Th2. For FACS staining, 1 million cells were plated per well in a 96 well plate, and were treated with PMA/Ionomycin for 2 hours, then Brefeldin A for another 2 hours. Antibodies used were anti-human IL-22 (antibody 3F11.1) and anti-gp120 as a control. Anti-mouse IFN-γ-FITC and anti-mouse IL-4-PE were obtained from BD Bioscience (San Diego Calif.). PE-conjugated goat anti-mouse IgG (also from BD Bioscience) was used as a secondary antibody. Cells were fixed with 2% paraformaldehyde for 30 minutes, then washed twice with PBS/2% FCS. Cells were resuspended in 0.5% saponin for 15 minutes, then antibodies were added at 0.5 ug/million cells for 30 minutes. Cells were then washed twice and secondary antibody was added in 0.5% saponin for 15 minutes. Finally, cells were washed and resuspended in FACS buffer and analyzed on a FACScan. FIG. 15 in the top panels show that Th1 cells can be differentiated from Th2 cells. Th1 cells are positive for IFN-γ, negative for IL4, and positive for IL-22. Th2 cells are mostly negative for IFN-γ, positive for IL4, and negative for IL-22.

Example 11

Generation of Anti-IL-22 Receptor (IL-22R)

To test binding of anti-IL-22R antibodies, 293 cells expressing hIL-22R and cells expressing GFP were used. One million cells were stained with different anti-hIL-22R antibodies at a concentration of 0.3 μg/million cells. The antibodies tested were 7E9, 8A12, 8H11, and 12H5. The secondary antibody was Goat anti-Mouse PE conjugated (Jackson Labs) used at a dilution factor of 1:200. Cells were washed and stained in FACS buffer (0.5% BSA/PBS). Staining with the test antibodies was carried out for 15 minutes at 4° C., then cells were washed, and secondary antibody was added for another 15 minutes at 4° C. Cells were washed twice before analysis on the FACScan. The results are shown in FIG. 16. For each graph in which the peaks do not overlap, the peak on the left corresponds to the control, and the peak on the right corresponds to the test antibody. FIG. 16 shows that all of the four anti-IL-22R antibodies tested were positive for binding IL-22R on transfected 293 cells. The antibodies 7E9, 8A12, 8H11, and 12H5 give good binding with very little background.

Example 12

IL-22R Blocking Antibodies

Figure 17:
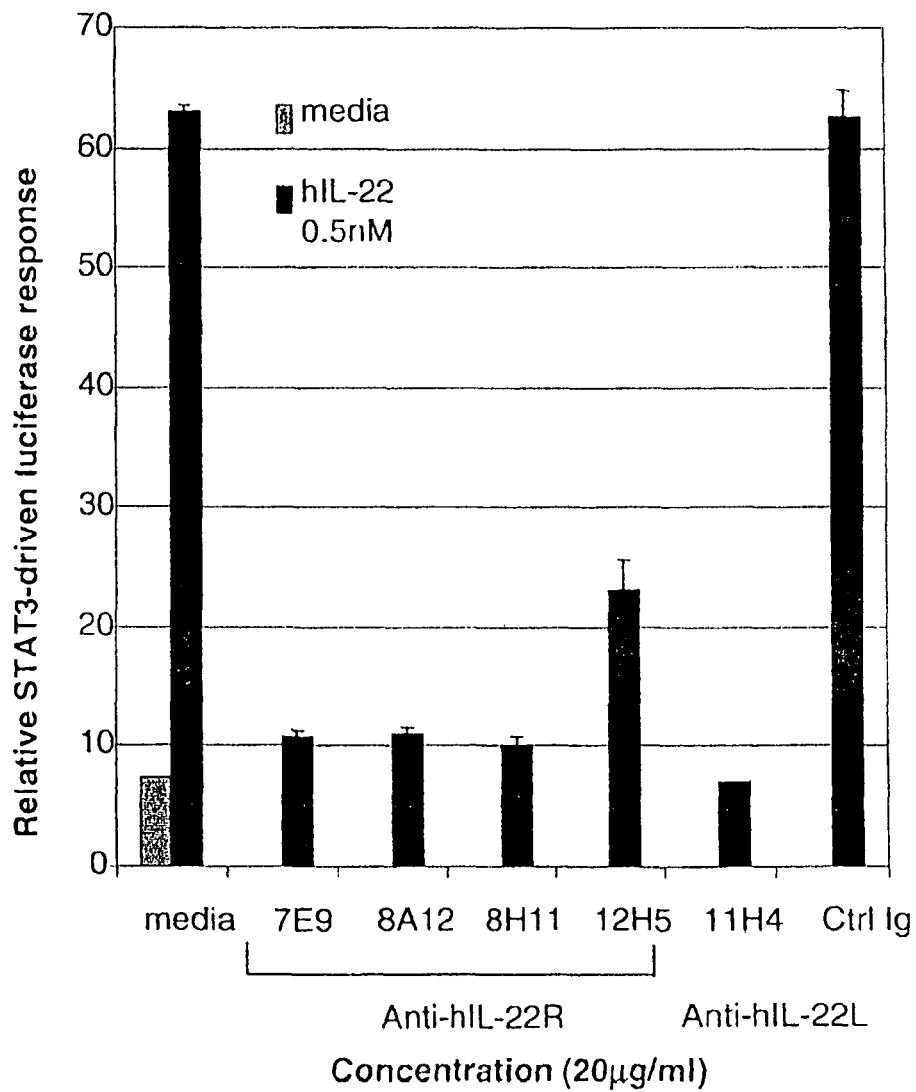
FIG. 17 shows that anti-IL-22R antibodies can block IL-22-induced expression of a STAT3 reporter construct, as described in Example 12.

To test for blocking activity of anti-IL-22R antibodies, a luciferase reporter construct (as described in Example 2) was used. If an antibody has blocking activity, STAT3 will not be activated and the luciferase response will be low. Cells expressing hIL-22R/hIL10Rb were plated at $0.2 \times 10^6$/well in a 24-well plate and the luciferase reporters TK-SIE-SRE-S (0.8 μg/well) and RL-TK-Luc (0.16 μg/well) were transfected into cells. The following day, hIL-22 was added to the wells at 0.5 nM, and each antibody was added at a 20 μg/ml. The anti-IL-22R antibodies tested were; 7E9, 8A12, 8H11 and 12H5. The control antibodies used were GP120 and 11H4, an anti-hIL-22 antibody shown to have blocking activity in Example 2. Sixteen hours later the cells were lysed and samples read on a luminometer to detect the luciferase activity. FIG. 17 shows that all four anti-IL-22R antibodies tested blocked the IL-22R-IL-22 interaction.

Example 13

IL-22R is Expressed on Primary Keratinocytes

Figure 18:
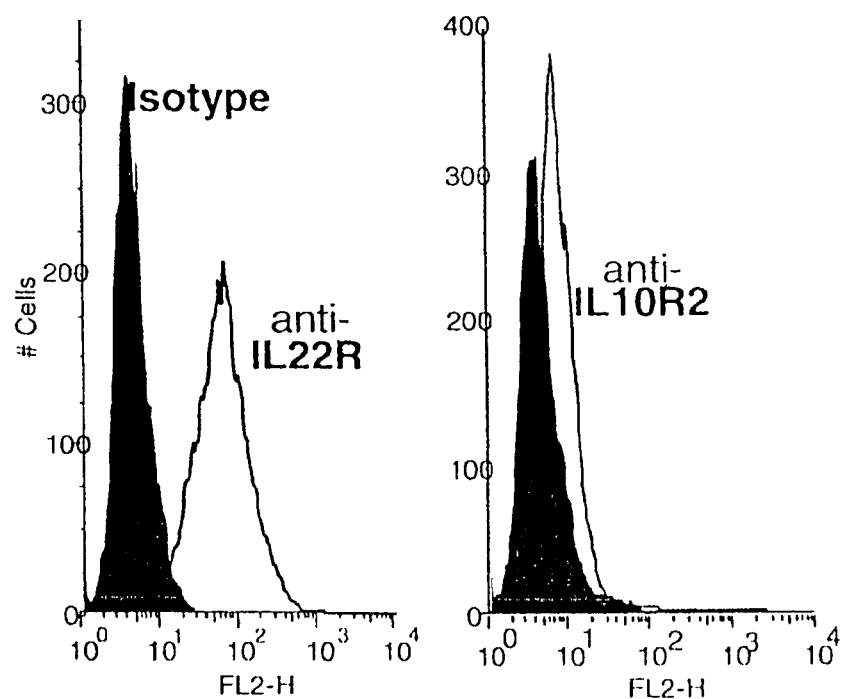
FIG. 18 shows expression of IL-22R and IL-10R2 on the surface of primary keratinocytes, as described in Example 13.

Keratinocytes are the cell population that overproliferates during psoriasis. Therapeutics that target keratinocytes are useful in the alleviation of psoriasis. Expression of IL-22R on primary human keratinocytes was determined by FACS analysis. Normal human epidermal keratinocytes (NHEK) donor lot 0526 were obtained from Cascade Biologics, passage #2, grown to 80% confluence, and were stained at 300-600K cells per sample. Anti-IL-22R serum was used at a dilution of 1:50 and pre-bleed serum was used at a dilution of 1:50 as the control. For IL10R2 staining, antibody from R&D (clone #90220, murine IgG1) was used at 0.3 μg per sample with murine IgG1-PE isotype control (BD Pharmingen #33815X). The secondary antibody for anti-IL-22R serum was rat anti-mouse IgG1-PE (BD Pharmingen #550083), used at 0.1 ug per sample. FIG. 18 shows that IL-22R and IL10R2 are expressed on NHEK. Therefore, blocking of the IL-22R or IL-22 may prove useful in alleviating disorders associated with keratinocyte hyperproliferation, such as psoriasis.

Example 14

Effect of IL-22 on Epidermal Cultures

Figure 19:
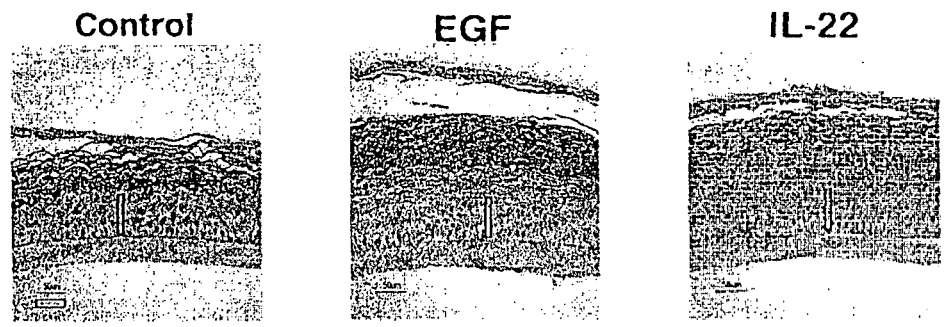
FIG. 19 shows that IL-22 induces thicking of human epidermis, as described in Example 14.

Reconstituted human epidermis (RHE) can be used as a model for the effects of cytokines on the skin. RHE and culture media were obtained from MatTek Corporation (Ashland, Mass.). RHE was equilibrated overnight (20-22 hrs) with 0.9 ml media at 37° C., 5% $CO_2$, to recover from shipping prior to start of the experiment and then cultured at air-liquid interface with 5 ml media at 37° C., 5% CO2. The effect of IL-22 on RHE was assayed using three different conditions. IL-22 (1.2 nM) or epidermal growth factor (EGF—R&D Systems) (1 nM) was added to the media. The control consisted of untreated media. RHE was cultured for 4 days, with a change of media every two days, adding fresh EGF or IL-22. RHE were harvested, fixed in 10% neutral buffered formalin (NBF) overnight, sectioned, and stained with hematoxylin and eosin (H&E). FIG. 19 shows that IL-22 treatment causes thickening of the epidermis. This indicates that IL-22 causes hyperplasia, or proliferation of cells that make up the epidermis.

Figure 20:
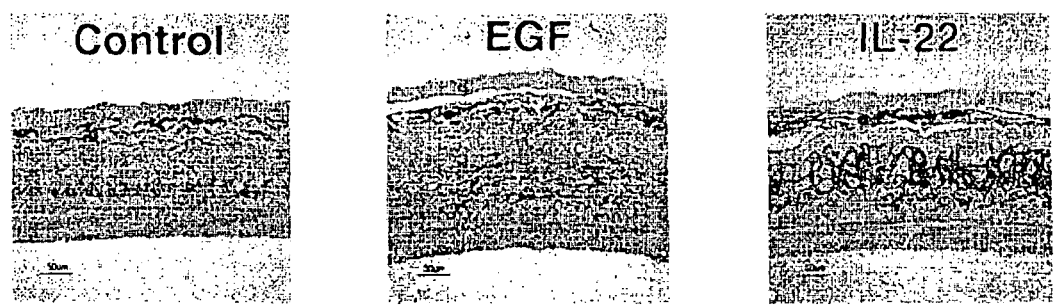
FIG. 20 shows that IL-22 induces cytokeratin 16 expression, a marker for keratinocyte turnover, as described in Example 14.

When these sections were stained for cytokeratin 16 (K16), a marker for keratinocyte proliferation, the RHE treated with IL-22 showed significantly more staining for K16. K16 is expressed only in proliferating skin cells such as in psorasis and wound healing (reviewed in Freedberg et al., Soc. Invest. Derm. 116:633-640 (2001)). FIG. 20 shows the K16 staining in IL-22 treated RHE relative to untreated and EGF treated RHE. The IL-22 treated RHE showed K16 throughout the tissue, whereas the staining is localized in the untreated and EGF treated sections.

Figure 21:
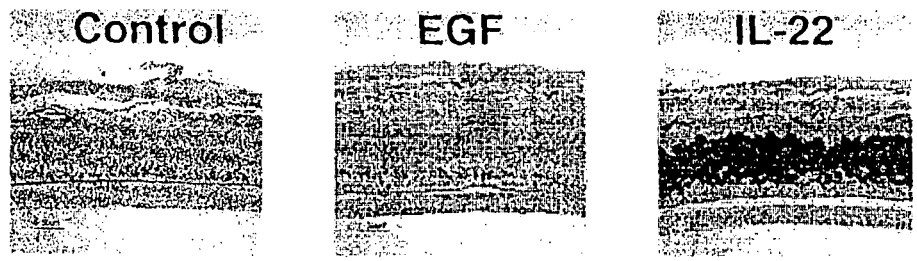
FIG. 21 shows that treatment of human epidermis with IL-22 causes induction of psoriasin expression, a gene highly expressed in psoriasis, as described in Example 14.

Treatment of RHE with IL-22 also induces psoriasin, a gene highly expressed in psoriasis. Psoriasin (S100A7) was originally discovered as a protein expressed in psorasis but not in normal skin (Madsen P., et al., J. Invest. Derm. 97: 701-712 (1991)). Psoriasin is expressed in activated cultured and malignant keratinocytes, and in malignant breast epithelial cells (Watson et al., Int. J. of Biochem. and Cell Bio. 30:567-571 (1998)). Current data support a role for psoriasin inflammatory skin disease, chemotaxis, and breast tumor progression. The correlation of psoriasin with psoriasiform hyperplasia of the skin suggests a role in keratinocyte differentiation. Psoriasin may also be chemotactic, stimulating the neutrophil and CD4+ T-lymphocyte infiltration of the epidermis that is a hallmark of psoriasis. FIG. 21 shows that treatment of RHE with IL-22 induces high levels of psoriasin expression. This result confirms the role that IL-22 and IL-22R play in psoriasis.

Figure 23:
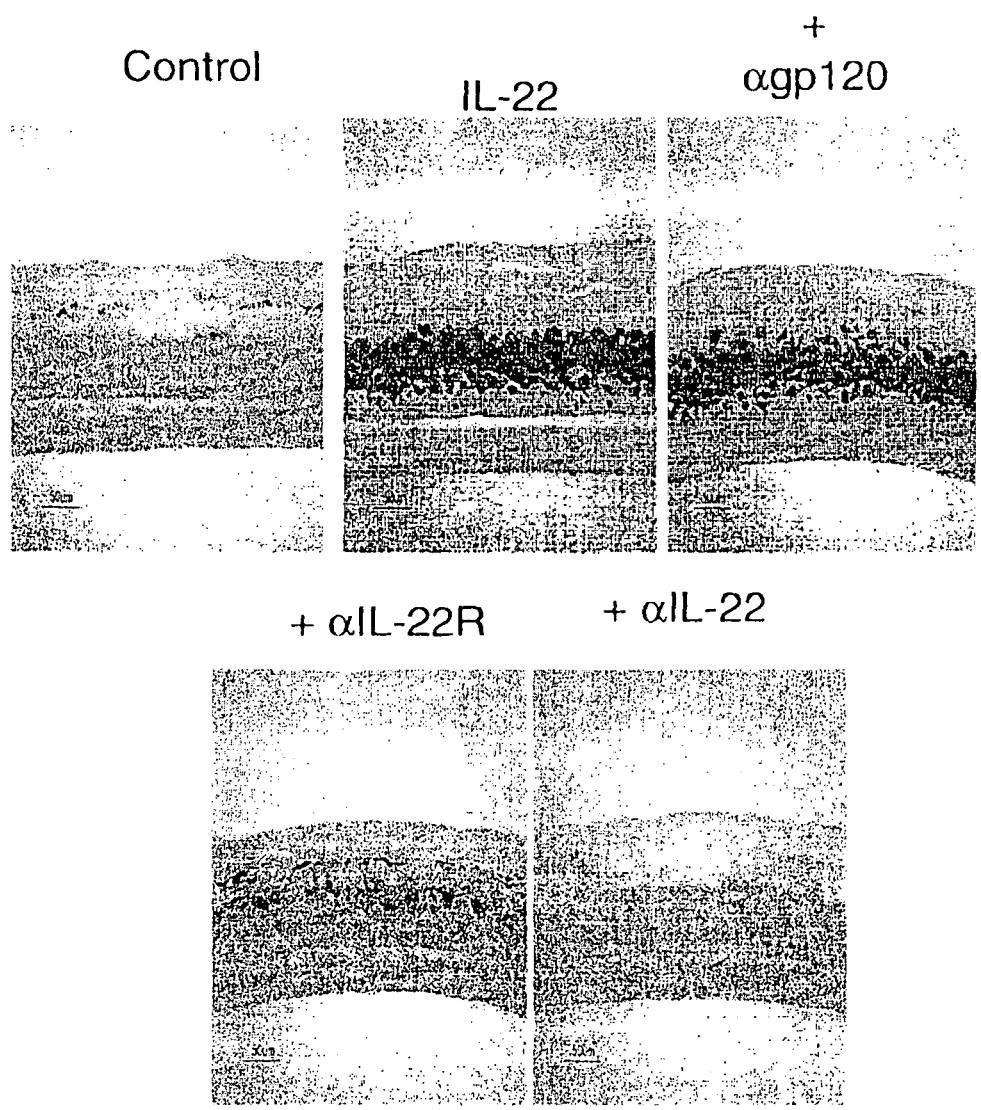
FIG. 23 shows that psoriasin expression is reduced by treatment with anti-IL-22 and anti-IL-22R antibodies, as described in Example 14.

The inducing effect of the IL-22 pathway on psoriasin can be blocked by antibodies directed to IL-22 or IL-22R. The anti-IL-22 antibody 8E11 administered at a concentration of 20 μg/ml reduced psoriasin expression to undetectable levels (see FIG. 23). When used at a concentration of 20 μg/ml, the anti-IL-22R antibody (7E9) also significantly reduced psoriasin expression as shown in FIG. 23.

Figure 24:
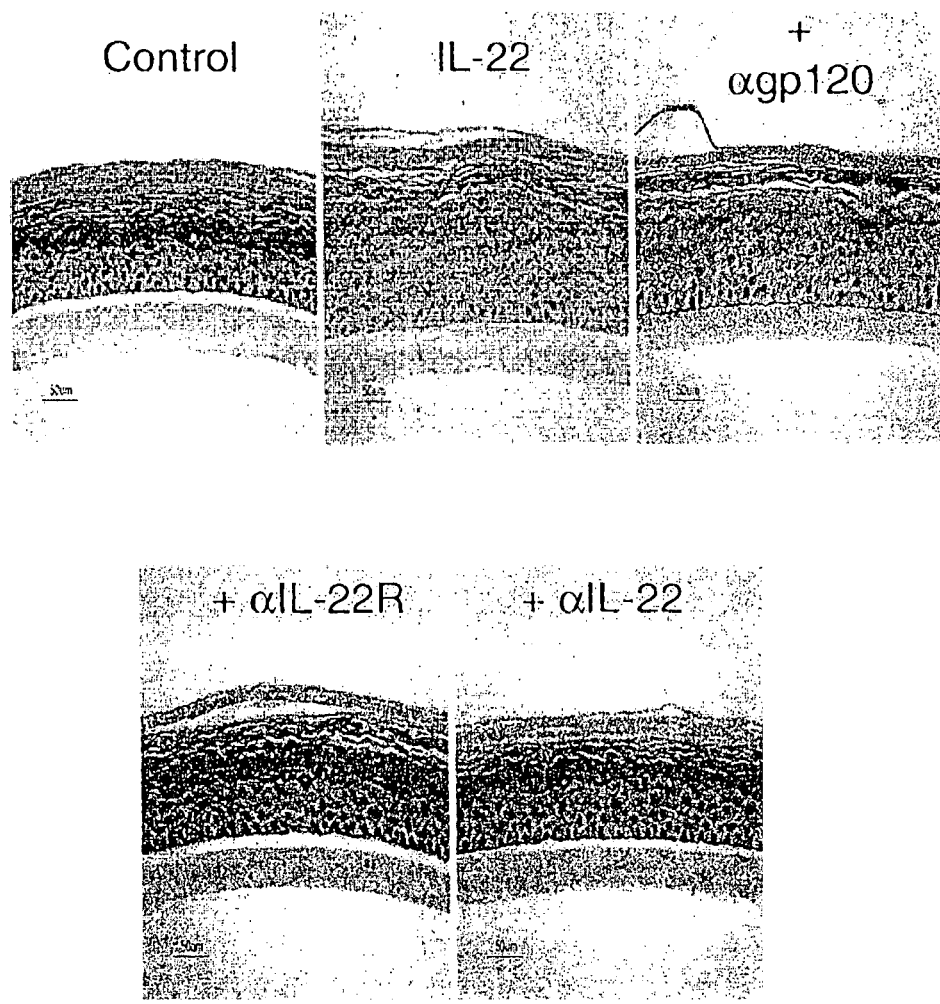
FIG. 24 shows that epidermal thickening is reduced by treatment with anti-IL-22 and anti-IL-22R antibodies, as described in Example 14.
Figure 25:
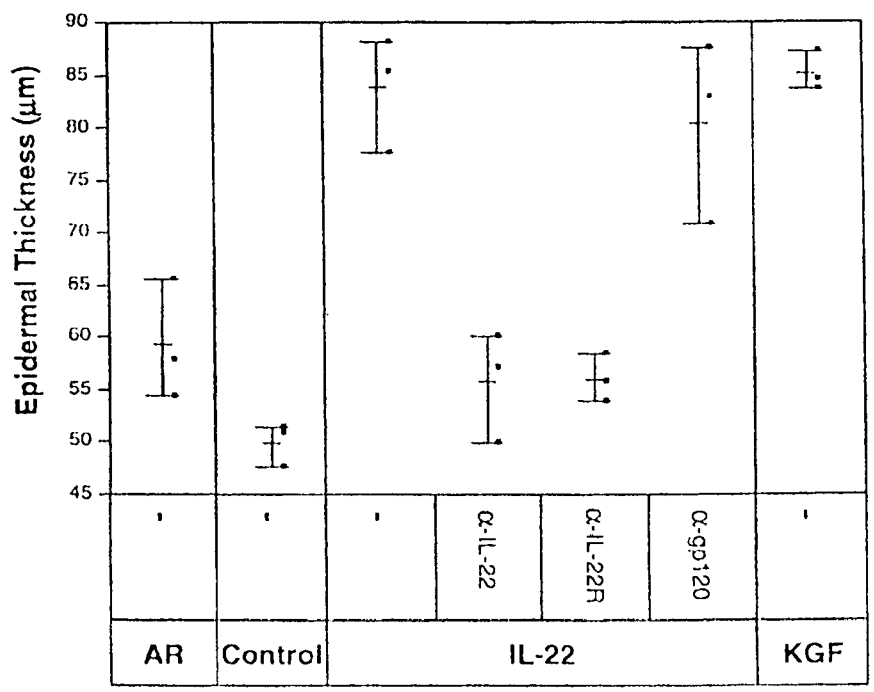
FIG. 25 shows that epidermal thickening is reduced by treatment with anti-IL-22 and anti-IL-22R antibodies, as described in Example 14.

The anti-IL-22 and anti-IL-22R antibodies were assayed to determine if they could reduce the epidermal thickening observed when RHE is treated with IL-22. The anti-IL-22 antibody (8E11) administered at a concentration of 20 μg/ml showed significant reduction of epidermal thickening (see FIG. 24). RHE treated with IL-22 reached a thickness of 80-90 μm, and treatment with anti-IL-22 (8E11) antibody reduces the RHE thickness to 50-60 μm (FIG. 25). The anti-IL-22R antibody (7E9) also reduced skin thickening. When used at a concentration of 20 μg/ml, anti-IL-22R antibody reduced RHE thickness from 80-90 μm to 55-60 μm (FIG. 25). This data shows that anti-IL-22 or anti-IL-22R antibodies can alleviate symptoms associated with psoriasis, such as epidermal proliferation and thickening.

Example 15

Microarray Analysis of Genes Induced by IL-22

To determine what genes were induced by IL-22, normal human epidermal keratinocytes (NHEK) derived from a single donor were plated and treated at 70% confluence for 24 hrs with 20 ng/ml IL-22. Media and supplements (EpiLife®+HKGS) were obtained from Cascade Biologics™ (Portland, Oreg.). The cells were washed and lysed. Total RNA was purified from the NHEK cells using Qiagen RNeasy Mini Kit. The RNA was subjected to microarray analysis, and the amount of gene expression was quantified (See Example 9 above for a description of microarray analysis).

Figure 22:
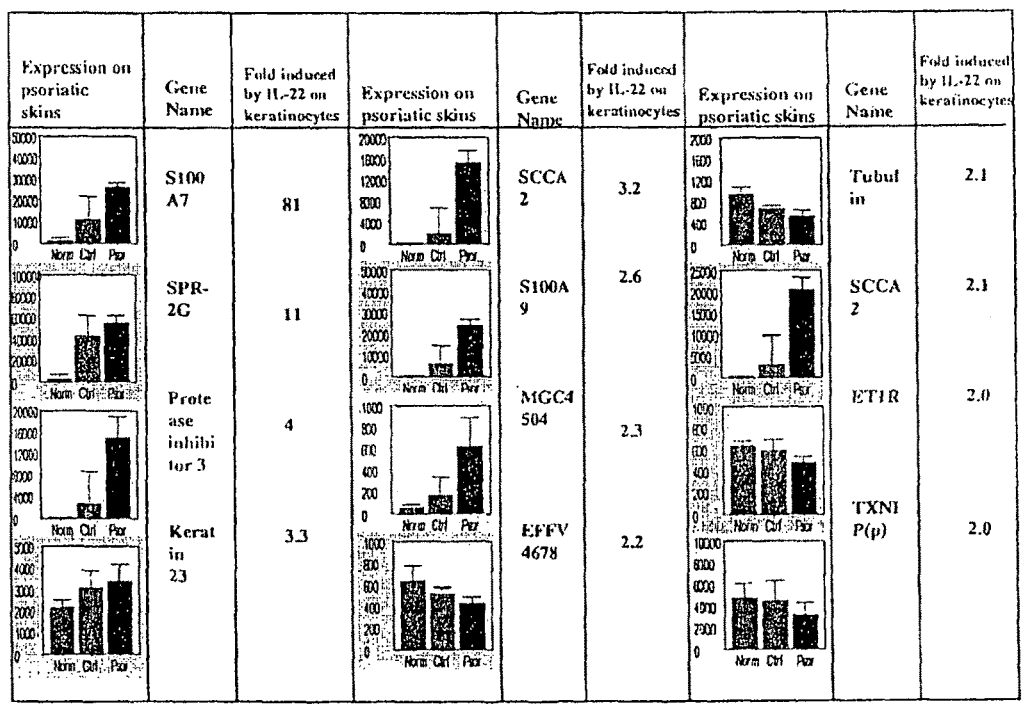
FIG. 22 shows that treatment of keratinocytes with IL-22 elevates the expression of several genes, including psoriasin, as described in Example 15.

Psoriasin is induced 81 fold upon stimulation by IL-22. SPR-2G is upregulated 11 fold. (See FIG. 22.) These results indicate that the IL-22 pathway is implicated in psoriasis. Therefore, antagonist and antagonist antibodies directed against IL-22 or IL-22R are useful in alleviating psoriasis.

Example 16

IL-23 Induces Hallmarks of Psoriasis In Vivo

A mouse model was used to compare the ability of IL-12 and IL-23 to induce psoriatic skin features. C57Bl/6 mice were injected subcutaneously in the ear with 500 ng of either recombinant IL-12 or recombinant IL-23 in a total volume of 20 μl PBS. Control mice were injected with 20 μl of PBS only. The mice were injected once every two days for 16 days. Each experimental group consisted of five mice. Ear thickness was measured before and at multiple time points after injection with a caliper (Mitutoyo America Corporation) and is reported as mean±standard deviation. For this experiment and subsequent experiments, statistical significance was calculated by one-way or two-way ANOVA using Prism software (GraphPad). All p values ≤0.05 were considered significant. Mouse ears were collected for routine histologic analysis using hematoxylin-and-eosin (H&E) staining.

Figure 26:
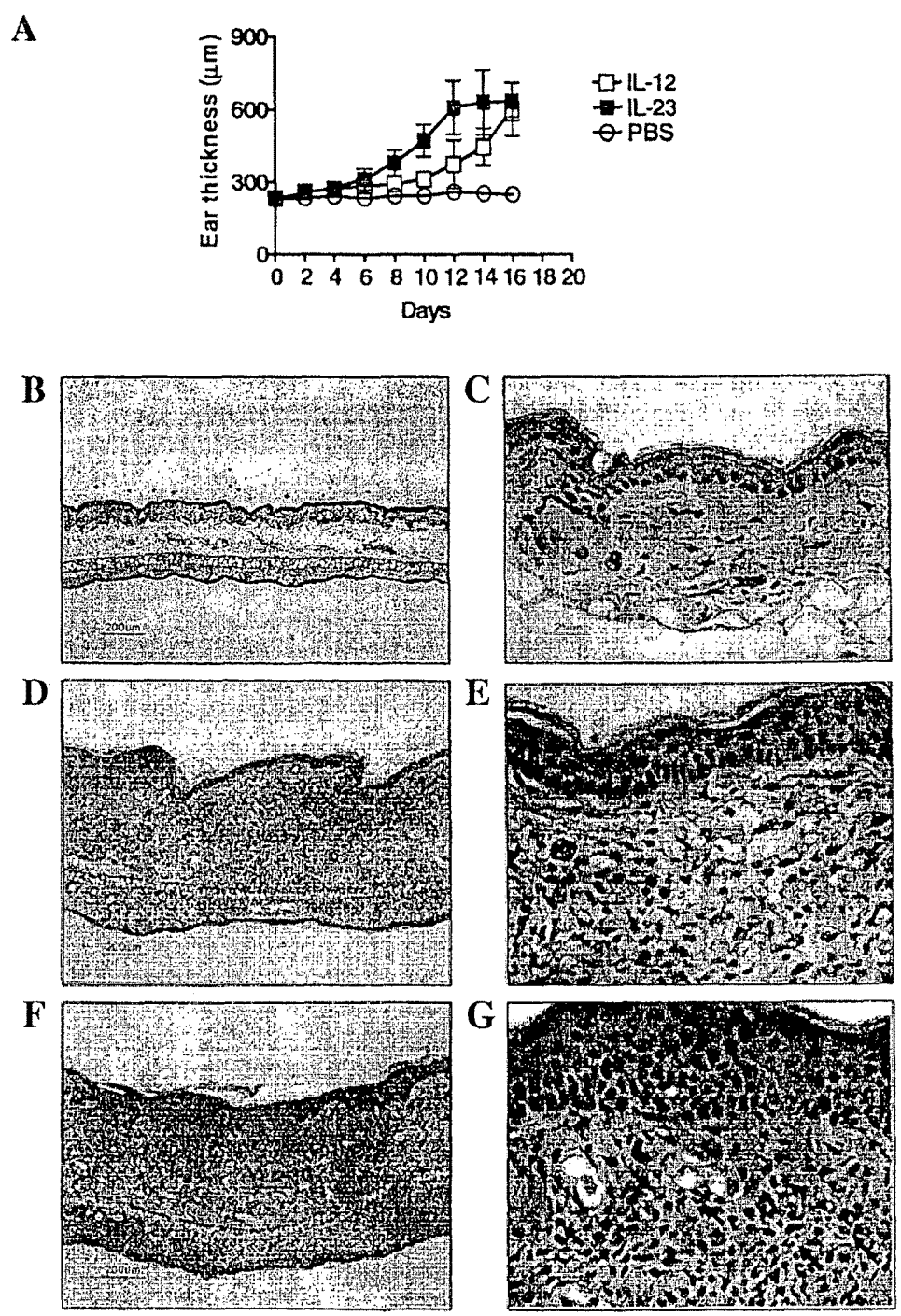
FIG. 26A-G shows that IL-23 and IL-12 induce epidermal thickening with distinct histological features, as described in Example 16.

As shown in FIG. 26A, both IL-12 and IL-23 injection induced a significant increase in ear thickness as early as one week following the first injection. For mice receiving IL-12, p was <0.001 (days 12, 14 and 16 vs PBS control respectively). For mice receiving IL-23, p was <0.001 (days 8, 12, 14 and 16 vs PBS control respectively). Histologic analysis revealed that both IL-12 and IL-23 injected ears developed marked inflammatory cellular infiltration and epidermal thickening (acanthosis) compared to the PBS treated control group; however, there were some clear histologic differences between these two groups. First, IL-12 induced mild to moderate acanthosis with a marked, predominantly mononuclear dermal inflammatory cellular infiltration (FIG. 26D, E) compared to the PBS control group (FIG. 26B, C), whereas IL-23 induced marked acanthosis with a mixed dermal inflammatory cellular infiltration of many polymorphonuclear leukocytes (FIG. 26F, G), including both neutrophils (arrows) and eosinophils. Epidermal hyperplasia and the presence of polymorphonuclear leukocytes are histologic hallmarks of psoriasis in humans, as well as very common histologic findings in mouse models of psoriasis. See P. C. van de Kerkhof et al., *Dermatologica* 174: 224 (1987) and P. R. Mangan et al., *Nature* (2006) 441:235.

Example 17

IL-22 Acts Downstream of IL-23 In Vivo

To identify cytokines that potentially act downstream of IL-12 or IL-23, real-time PCR was used to examine the expression of a panel of cytokines from ear skin samples injected with IL-12 or IL-23. Ear skin injections and histologic analysis were carried out as described in the preceding Example. On day 8 of the experiment, RNA was isolated from individual mouse ears and real-time PCR was performed to quantify the levels of mRNA encoding IFN-γ, IL-17, and IL-22. Specifically, RNA was isolated by RNeasy Mini Kit (Qiagen, Valencia, Calif.) according to the manufacturer's instructions. Real-time RT-PCR was conducted using an ABI 7500 Real-Time PCR System (Applied Biosystems, Foster City, Calif.) with primers and probes using TaqMan™ One-Step RT-PCR Master Mix reagents (Applied Biosystems). Reactions were run in duplicate and samples were normalized to the control housekeeping gene RPL-19 and reported according to the ΔΔCt method.

Figure 27:
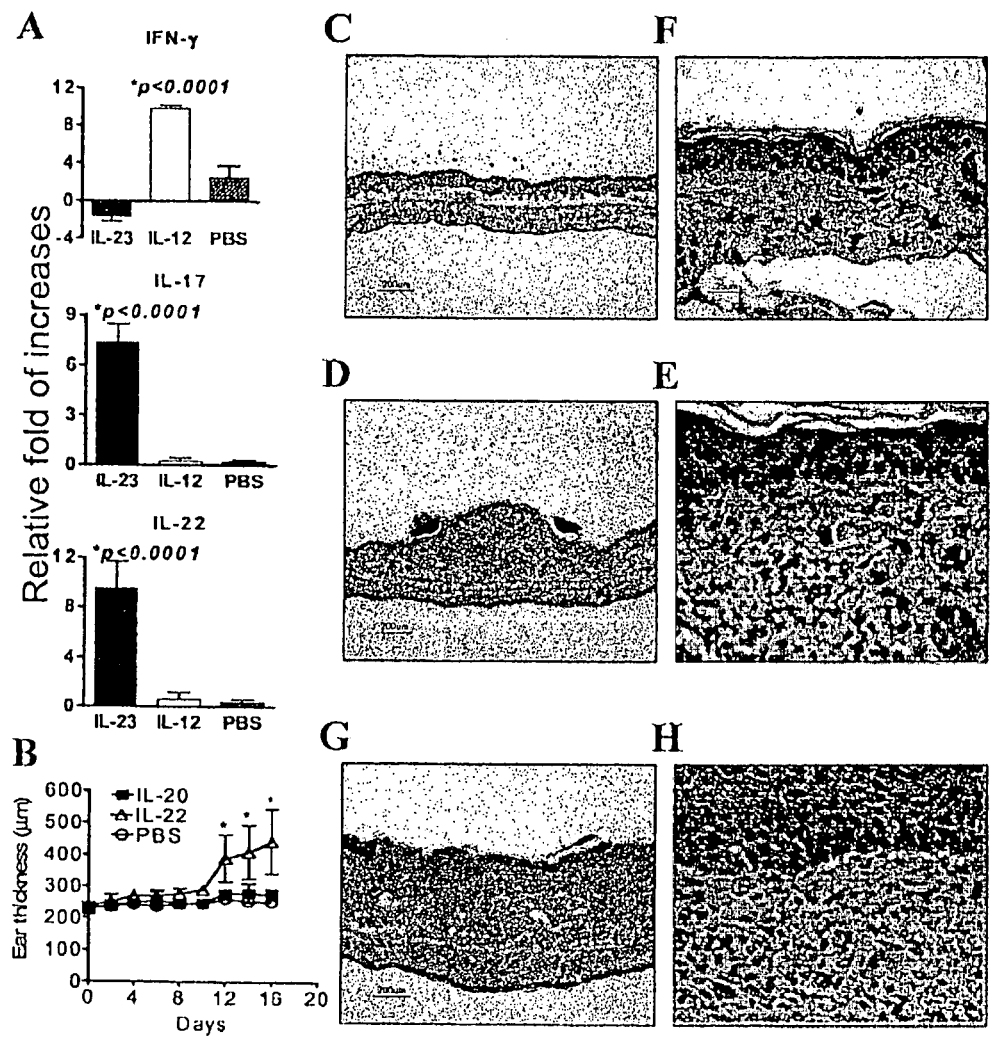
FIG. 27A-H shows that IL-23 induces expression of IL-22, and IL-22 induces dermal inflammation and epidermal thickening in vivo, as described in Examples 17 and 18.

As shown in FIG. 27A, IL-12 induced a significant increase in IFN-γ expression in the ear eight days after the first injection. IL-23 induced IL-17 production and inhibited IFN-γ production relative to the PBS-treated control group (FIG. 27A). Interestingly, IL-22 was also significantly up-regulated following IL-23 injection, but not after injection of IL-12 (FIG. 27A). These data suggested a link between IL-23 and IL-22.

Figure 28:
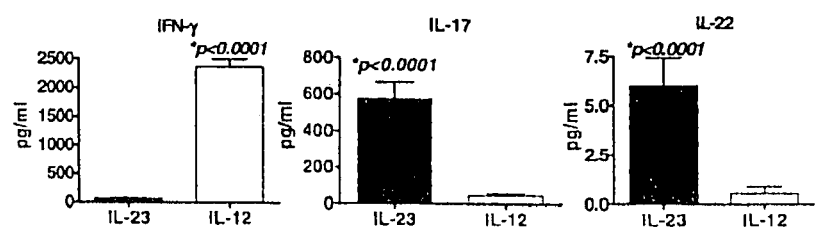
FIG. 28 shows that IL-12 and IL-23 induce expression of distinct sets of cytokines, as described in Example 17.

To confirm that the cytokines were produced by lymphocytes that had infiltrated the ear, lymphocytes were eluted out of the treated ears and cytokine production was measured by ELISA upon activation. Consistent with the real-time RT-PCR data, cells from IL-23 injected ears preferentially produced IL-22 and IL-17, whereas cells from IL-12 injected ears secreted large amount of IFN-□□□ FIG. 28).

Example 18

IL-22 Induces Dermal Inflammation and Epidermal Hyperplasia In Vivo

To determine whether IL-22, like IL-23, is capable of inducing psoriatic skin features in vivo, mice were injected subcutaneously in the ear with IL-22 or with PBS alone, as described above in Example 16. As shown in FIG. 27B, IL-22 induced a significant increase in ear thickness compared to the PBS treated group. IL-20, another cytokine from the IL-10 family, induced only a very mild and localized increase in ear thickness. This finding was in contrast to a previous report where epidermal transgenic overexpression of IL-20 induced marked epidermal hyperplasia, a result that suggested that IL-20 might potentially play a role in epidermal function as well as in psoriasis. See Blumberg et al., *Cell* 104:9 (2001). Histologic analysis showed that IL-22 treated mouse ears had a similar histologic appearance to ears in the IL-23 treated group shown in FIGS. 26F and G, exhibiting marked acanthosis and mixed dermal inflammatory cellular infiltration (FIG. 27G, H), including many neutrophils (arrows) and some eosinophils. In contrast, IL-20 treated ears had only mild-moderate focal acanthosis with only moderate and very focal mixed inflammation (FIG. 27D, E) relative to the PBS treated group (FIG. 27C, F). These data suggested that IL-22 is essential for IL-23-induced skin inflammation and acanthosis.

Example 19

An Anti-IL-22 Blocking Antibody Significantly Reduced IL-23-Induced Acanthosis

To confirm that IL-23 acts through IL-22 to induce psoriatic skin features, the effect of the anti-IL-22 monoclonal antibody 8E11 on IL-23 induced dermal inflammation and acanthosis was examined. Mice were injected subcutaneously in the ear with IL-23 or PBS as described above (Example 16), except that the injections were carried out over a span of 14 days. The mice were also injected intraperitoneally with 8E11 or with control monoclonal antibody of the IgG1 isotype at a concentration of 200 μg per mouse and at a frequency of once every two days for 14 days. On day 14, mouse ears were collected for histologic analysis using H&E staining.

As shown in FIG. 29A, 8E11 ("anti-IL-22 mAb") significantly reduced IL-23-induced epidermal acanthosis (*p<0.001) relative to treatment with control IgG1 antibody. (Compare also FIGS. 29D and E (anti-IL-22 mAb) with B and C (control IgG1).) Furthermore, mice treated with anti-IL-22 mAb also demonstrated a moderate decrease in dermal inflammation. However, mice treated with anti-IL-22 mAb still displayed a moderate inflammatory cellular infiltration when compared to ear skins treated with PBS. (Compare FIGS. 29D and E (anti-IL-22 mAb) with F and G (PBS).)

Example 20

IL-23-Induced Acanthosis was Significantly Reduced in IL-22 Deficient Mice

To further confirm that IL-23 acts through IL-22 to induce psoriatic skin features, the effect of IL-23 on both wild type and IL-22 deficient mice was examined. IL-22 deficient mice (i.e., homozygous IL-22 knockout mice, referred to as "IL-22$^{-/-}$ mice") were generated by targeted gene disruption according to the strategy depicted in FIG. 30A. Exons 1-4 (closed boxes) of the IL-22 coding sequence were replaced with a neomycin resistance cassette flanked by loxP sites. Heterozygous mice carrying the conditional allele were crossed with a transgenic line in which the protamine 1 (Prm) promoter drove the Cre recombinase. The conditional allele was excised during spermatogenesis in compound heterozygous males (i.e., heterozygous for the conditional allele and the PrmCre transgene). The compound heterozygous males were mated to wild-type females, and the resulting progeny were screened for the excised allele and the loss of the PrmCre transgene. Offspring were backcrossed into C57Bl/6 background for at least six generations. Mouse genotypes were confirmed by PCR using the primers indicated in FIG. 30B.

IL-22 expression was examined at the mRNA and protein levels in Th cells from wild type and IL-22$^{-/-}$ mice. IL-22 mRNA expression was examined in Th1, Th2, and Th$_{IL-17}$ cells from wild type ("+/+") and IL-22$^{-/-}$ ("-/-") mice (FIG. 30C) using RT-PCR, confirming that IL-22 mRNA was not detected in IL-22$^{-/-}$ mice. The expression of IL-22, IL-17, IFN-γ, and IL-4 was examined in Th1, Th2, and Th$_{IL-17}$ cells from wild type ("WT") and IL-22$^{-/-}$ ("KO") mice using ELISA. The results are shown in FIG. 30D for each of IL-22, IL-17, IFN-γ, and IL-4, as indicated at the top of each graph, with filled bars and open bars indicating expression levels in WT and KO mice, respectively. Additionally, CD4 T cells from IL-22$^{-/-}$ mice were capable of being activated and differentiating to all T helper subsets and were able to produce normal levels of IL-17, IFN-γ, and IL-4 relative to wild type CD4 T cells. As expected, however, IL-22 was absent from IL-22$^{-/-}$ CD4 T cells. IL-22$^{-/-}$ mice were observed to develop normally and had similar lymphocyte composition and development in all major lymphoid organs examined as compared to wild type mice. (Data not shown.)

Figure 31:
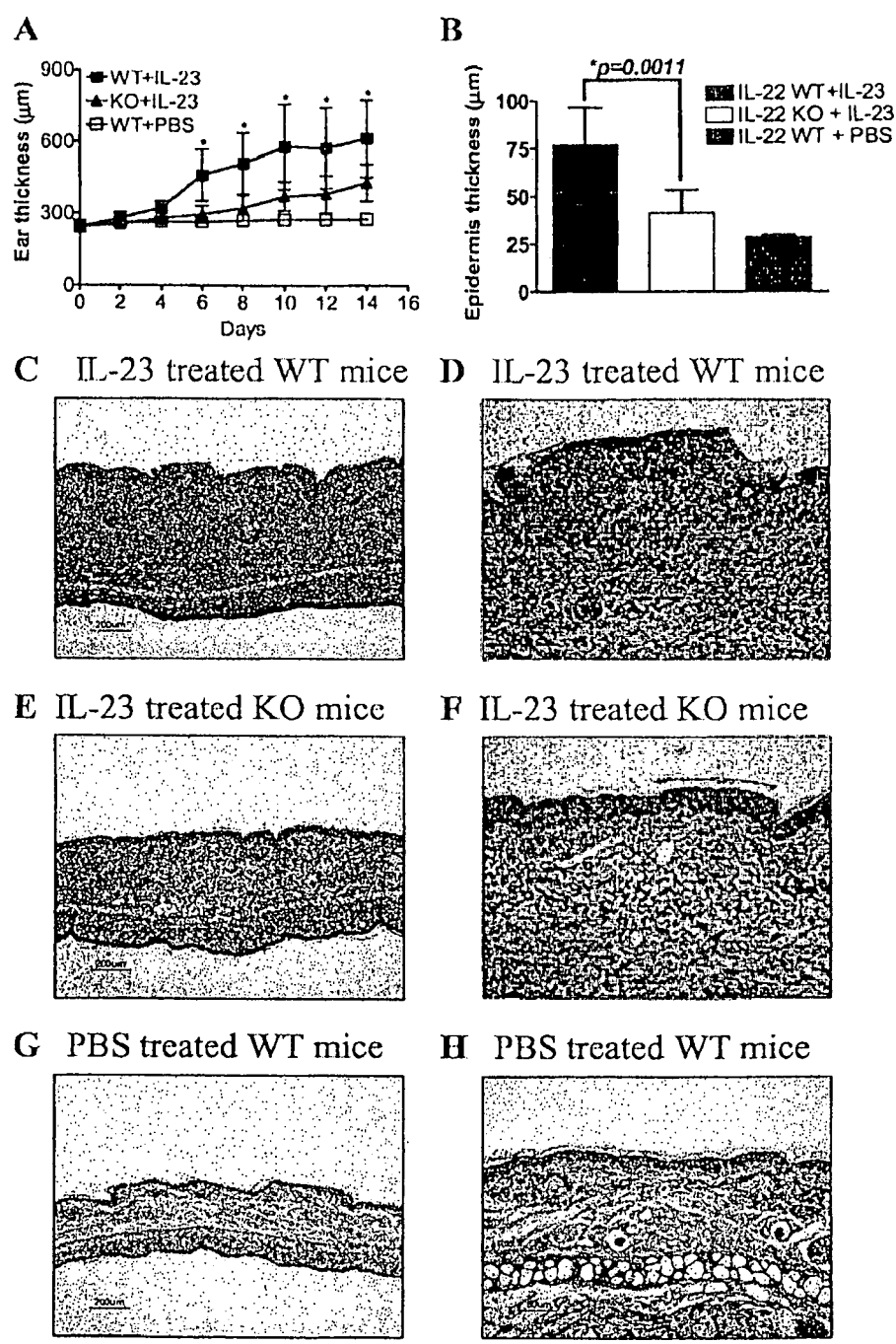
FIG. 31A-H shows that IL-23-induced acanthosis is significantly reduced in IL-22 deficient mice, as described in Example 20.
Figure 32:
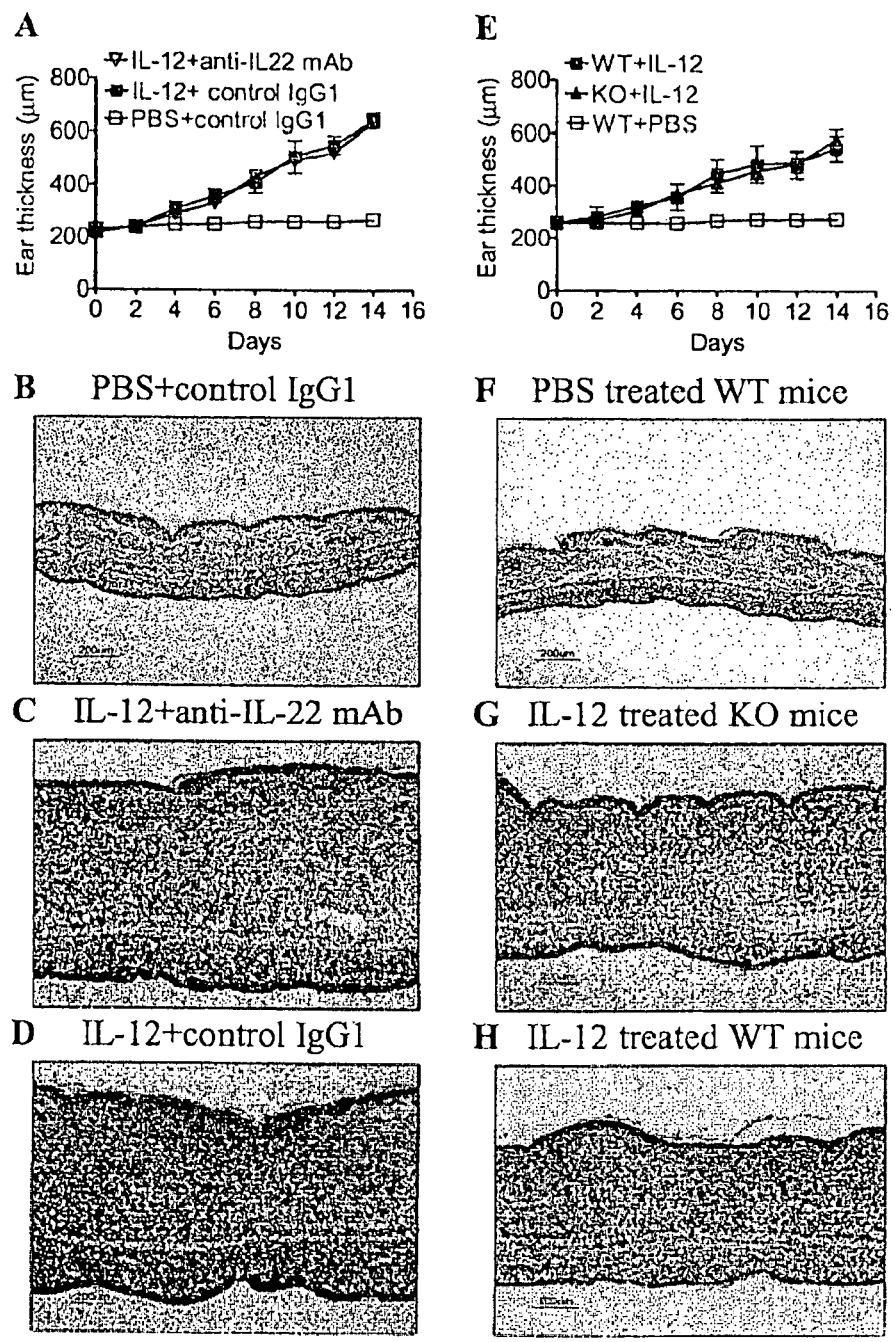
FIG. 32A-H shows that IL-22 deficiency had no effect on IL-12-induced acanthosis, as described in Example 20.

IL-22$^{-/-}$ mice and wild-type littermates were injected subcutaneously in the ear with IL-23 or PBS as described above (Example 16). On day 16, mouse ears were analyzed by routine histologic analysis. As shown in FIGS. 31A and B, IL-23 induced significantly less ear thickness and epidermal thickness in IL-22$^{-/-}$ mice compared with the control groups. (IL-22$^{-/-}$ mice are referred to in this figure and FIG. 32 as "KO" or "IL-22 KO"; wild type mice are referred to in this figure and FIG. 32 as "WT" or "IL-22 WT.") By histological staining, both epidermal acanthosis and dermal inflammation were significantly reduced in IL-22$^{-/-}$ mice (FIGS. 31E and F, respectively) compared to IL-23-treated wildtype littermates (FIGS. 31C and D, respectively). In contrast to these results, IL-22 deficiency had no effect on IL-12 induced ear skin inflammation at all. (FIG. 32.) Therefore, the data show that IL-22 plays a crucial role in the dermal inflammation and epidermal acanthosis induced by IL-23, but not by IL-12.

Example 21

IL-23 Induces IL-22 Production from Various IL-23-Activated Lymphocytes

To further investigate the ability of IL-23 to induce IL-22, various lymphocyte populations were isolated and stimulated in vitro under the conditions indicated in FIG. 33. ELISA was performed to detect IL-22 in the culture supernatants and is reported in FIG. 33A as mean±standard deviation. The ability of IL-23 to induce IL-10 family cytokines other than IL-22 was also examined. Splenocytes from DO11.10 TCR transgenic mice were stimulated with 0.3 μM OVA peptide under indicated T-helper cell polarization conditions for 4 days, then rested for two days and restimulated with plate-bound anti-CD3 (10 μg/ml) and soluble anti-CD28 (5 μg/ml) for another 2 days. Real-time RT-PCR was performed on RNA isolated from cells under the indicated conditions to quantify mouse IL-19, IL-20 and IL-24 mRNA expression. RNA from normal mouse splenocytes was also included as a control. As shown in FIG. 33B, IL-23 did not induce expression of any other IL-10 family cytokines tested.

Example 22

IL-22 is a New Effector Cytokine from the Th$_{IL-17}$ Lineage

Recently, IL-23 has been linked to the development of a new IL-17 producing effector CD4$^+$ T cell lineage (Th$_{IL-17}$). L. E. Harrington et al., *Nat. Immunol.* 6:1123 (2005); H. Park., *Nat. Immunol.* 6:1133 (2005). IL-23 is able to induce the Th$_{IL-17}$ lineage cells from naïve CD4+ T cells in the presence of APC and antigen, but it is unable to initiate IL-17 production when applied to purified naïve T cells activated with anti-CD3/anti-CD28. L. E. Harrington et al., *Nat. Immunol.* 6:1123 (2005); M. Veldhoen et al., *Immunity* 24:179 (2006). Moreover, TGF-β and IL-6 have been suggested to be the de novo factors for Th$_{IL-17}$ subset differentiation. M. Veldhoen et al., *Immunity* 24:179 (2006).

Experiments were carried out to test whether IL-22 could be an additional effector T cell cytokine induced by IL-23 under authentic TCR stimulation. CD4+ T cells from DO11.10 TCR transgenic mice were activated with 0.3 μM OVA peptide for four days under Th1-polarizing (IL-12 and anti-IL-4), Th2-polarizing (IL-4, anti-IL-12 and anti-IFN-γ), Th$_{IL-17}$-polarizing (IL-23, anti-IFN-γ and anti-IL-4) or Th0 (anti-IL12/23 p40, anti-IFN-γ and anti-IL-4) conditions as previously described. L. E. Harrington et al., *Nat Immunol* 6:1123 (2005). RNA was extracted from the cells and real-time PCR was performed to detect expression of mRNA encoding various murine cytokines (indicated above the graphs in FIG. 34A). Additionally, ELISA was performed on the culture supernatants to detect expression of various cytokines at the protein level. As shown in FIG. 34A, IL-17 was induced by IL-23, whereas IFN-γ and IL-4 were produced by Th1 and Th2 cells respectively. IL-22 was produced, both at the mRNA and protein levels, from IL-17 producing Th$_{IL-17}$ cells.

To determine whether IL-22 is a new effector cytokine from the fully committed Th$_{IL-17}$ lineage, polarized T cells as described above were rested for two days and then restimulated for two days with plate-bound anti-CD3 (10 μg/ml) and soluble anti-CD28 (5 μg/ml) in the absence or presence of IL-23. ELISA was performed to detect expression of the murine cytokines indicated above the graphs in FIG. 34B. The results demonstrate that IL-17 was produced specifically from the Th$_{IL-17}$ subset, even in the absence of IL-23, and IL-23 enhanced IL-17 production. IL-23 failed to promote IL-17 production from committed Th1 and Th2 cells. IL-22 demonstrated an identical expression pattern as IL-17, indicating IL-22 was a true effector cytokine expressed by this new Th$_{IL-17}$ subset.

Figure 35A:
FIG. 35A-C show that IL-22 and IL-17 are produced by the same Th lineage (Th$_{IL-17}$), as described in Example 22.
Figure 35B:
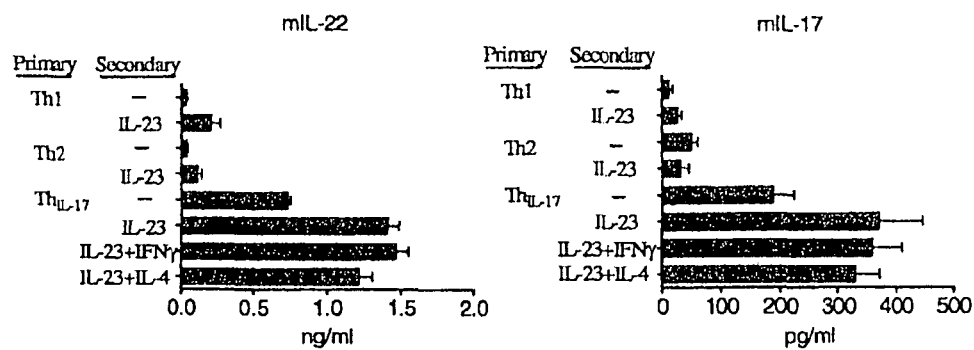

Previously, IL-23 receptor was reported to be expressed on activated/memory T cells. C. Parham et al., *J Immunol* 168:5699 (2002). The above experiments did not exclude the possibility that IL-23 acted on memory T cells to produce IL-22. To address this more critically, the above studies were repeated using naïve CD4+ T cells isolated from DO11.10 TCR transgenic mice. Specifically, CD4+ T cells from Rag2−/−.DO11.10 TCR-transgenic mice were stimulated with OVA peptide-pulsed BALB/c splenic feeder cells (irradiated, T cells depleted) for 72 hours in Th1-polarizing conditions (IL-12 and anti-IL-4), Th2-polarizing conditions (IL-4, anti-IL-12 and anti-IFN-γ), Th$_{IL-17}$-polarizing (IL-23, anti-IFN-γ and anti-IL-4), or other conditions as indicated in FIG. 35A. As shown in that figure, Th$_{IL-17}$ cells produced the highest levels of IL-22, while Th1 also secreted detectable levels of IL-22. Furthermore, addition of either IFN-γ or IL-4 completely abolished IL-17 production; however, these two cytokines only moderately inhibited IL-22 production (FIG. 35A). These data suggest potentially different pathways for the induction of IL-17 versus IL-22 expression. However, fully established Th$_{IL-17}$ cells produced both IL-17 and IL-22 upon restimulation for 48 hours in the indicated secondary conditions (FIG. 35B). IL-23 further boosted the levels of these cytokines in a manner that could not be blocked by either IFN-γ or IL-4 (FIG. 35B). These data confirm the stability of this Th$_{IL-17}$ lineage.

Figure 35C:
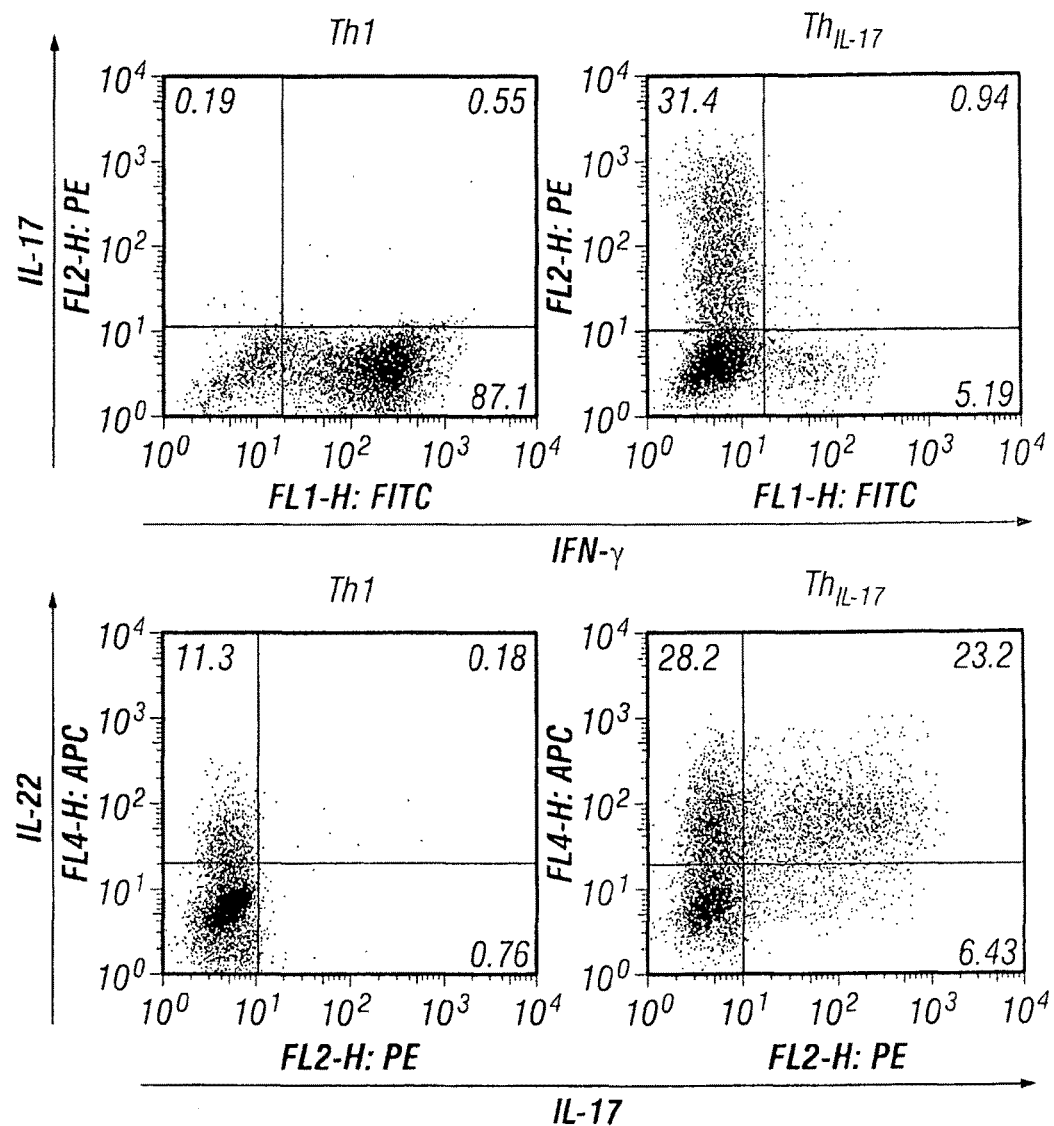

To further investigate whether IL-17 and IL-22 are produced by the same cells during activation, Th$_{IL-17}$ cells were stimulated with PMA and ionomycin, and antibodies to IL-22 or IL-17 were used for intracellular staining. As shown in FIG. 35C, IL-17-producing cells were mainly observed from the Th$_{IL-17}$ axis (top panel). IL-22-producing cells were also preferentially detected from the Th$_{IL-17}$ lineage (bottom panel). Costaining for both IL-22 and IL-17 revealed that a substantial portion of cells from the Th$_{IL-17}$ lineage were producing both IL-22 and IL-17 simultaneously, indicating that IL-22 and IL-17 are produced from the same cells.

Figure 36:
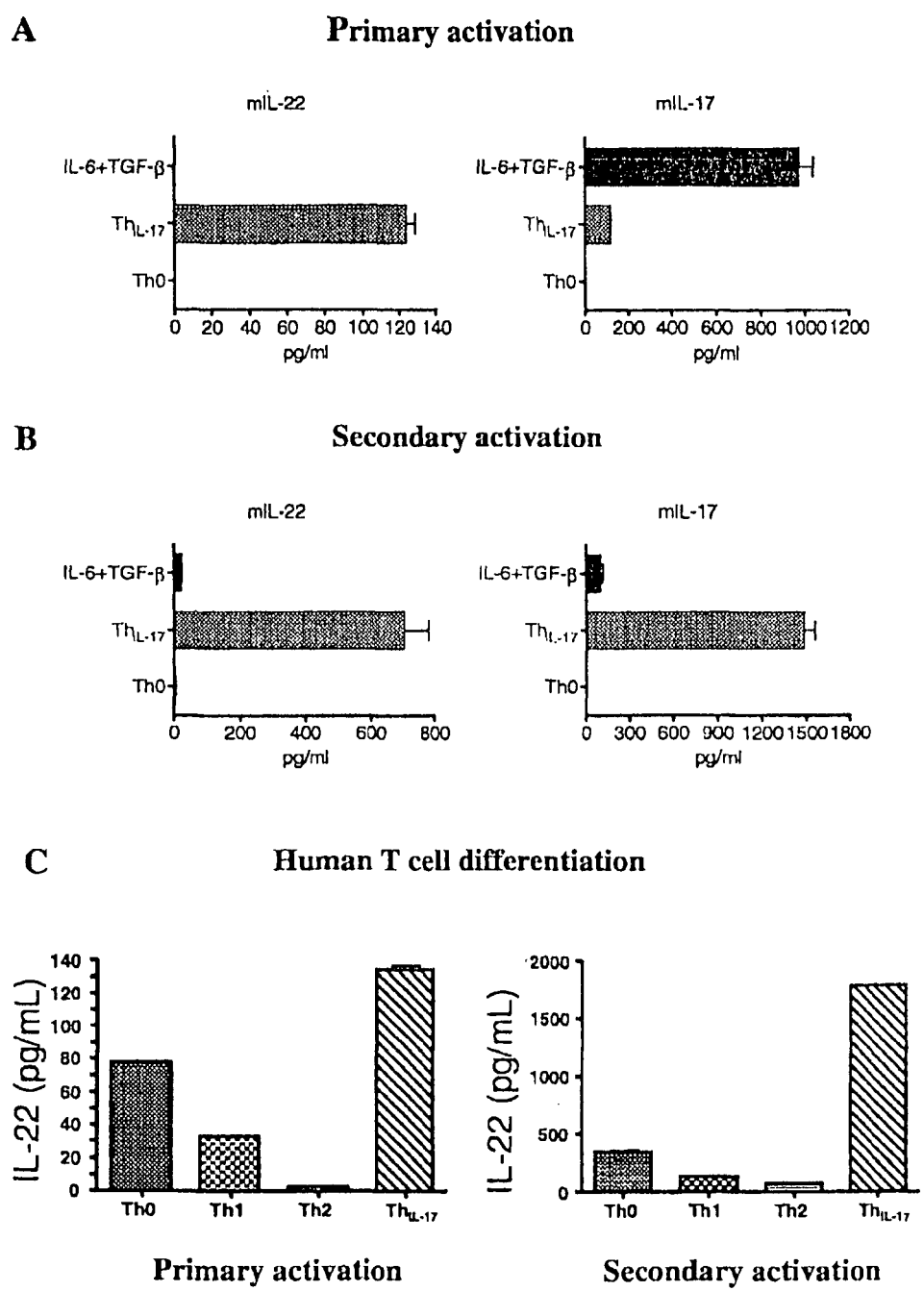
FIG. 36A-C shows that IL-23 stimulates IL-22 production from upon activation of naïve T cells, as described in Example 22.

As discussed above, recent studies also suggest that other factors from APC may be the primary driving force behind the differentiation of IL-17-producing T cells from naïve CD4+ T cells, since IL-23 failed to induce de novo IL-17 production from purified naïve CD4 T cells. M. Veldhoen et al., *Immunity* 24:179 (2006). Two of the factors critical for production of IL-17 from naïve CD4 T cells have been identified as TGF-β and IL-6. Id. To determine whether these factors were also critical for IL-22 production in mice, purified naïve CD4 T cells (>98%) were stimulated with plate-bound anti-CD3 (10 μg/ml) and soluble anti-CD28 (5 μg/ml). Consistent with published data, TGF-β and IL-6, rather than IL-23, induced IL-17 production (FIG. 36A, right panel). Surprisingly, in contrast to the induction of IL-17, IL-22 was still only induced in the presence of IL-23 and could not be induced by TGF-β and IL-6 (FIG. 36A, left panel). These data suggest that transcription of IL-17 and IL-22 could be regulated differently. However, as previously reported, TGF-β and IL-6 could not establish a long term IL-17 producing T cell lineage without IL-23 (FIG. 36B). The data thus demonstrate that IL-23 might be one of the primary factors driving a T cell subset producing IL-22.

Next we examined whether a similar IL-22 producing T cell lineage could be established from human CD4 T cells. We found that IL-23 could induce IL-22 secretion from purified naive human CD4+ T cells stimulated with anti-CD3/anti-CD28 under Th$_{IL-17}$-polarizing conditions (FIG. 36C, left panel). These cells could produce IL-22 upon restimulation without the addition of exogenous IL-23 again (FIG. 36C, right panel), indicating the formation a stable T cell lineage. Although these cells were cultured under similar conditions as in the above murine studies, we could not detect IL-17 production above the assay limit (data not shown).

In conclusion, the data establish for the first time that IL-23 can induce an IL-22-producing T cell subset from both murine and human naïve CD4 T cells. The production of IL-17 by this lineage depends upon other environmental factors. While under authentic antigen and APC stimulating conditions, IL-23 drove the T cell subset producing both IL-22 and IL-17. IL-23 also stimulated IL-22 production when naïve T cells were activated by anti-CD3 and anti-CD28. TGF-β and IL-6, which can induce transient IL-17 production from naïve T cells but not long term lineage commitment, failed to drive IL-22 production.

Example 23

IL-19, IL-20, and IL-24 Also Induce Epidermal Thickening

IL-22 belongs to a family of cytokines that include IL-19, IL-20, and IL-24, all of which show elevated expression in psoriatic skin. Those cytokines were also tested to determine whether they, like IL-22, are capable of inducing epidermal hyperplasia and acanthosis. RHE was cultured for four days and treated with IL-19, IL20, IL-22, or IL-24 at 20 ng/ml or EGF at 6 ng/ml. The treated RHE was stained with H&E. The results are shown in FIG. 37A. All cytokines induced aconthosis of the viable nucleated epidermis, as denoted by the increased length of the double-headed arrows. Consistent with previous observations (above), IL-22 induced hypogranulosis, or a decrease in the granular cell layer (arrowheads), as well as hyalinization of the lower stratum corneum (asterisks). IL-22 also induced parakeratosis in RHE cultured for 7 days (data not shown). Hypogranulosis and parakeratosis are frequently observed histological features of psoriasis. IL-19, IL-22, and IL-24 induced only epidermal acanthosis with little or no apparent effect on either the granular cell layer or the stratum corneum. EGF induced epidermal aconthosis with hypergranulosis and compacting of the keratinocytes within the stratum granulosum (arrows). Epidermal thickening induced by IL-19, IL20, IL-22, or IL-24 was quantified in an independent experiment and is represented graphically in FIG. 38. IL-22 had the greatest effect. The inflammatory cytokines TNF-α, IFN-γ, and IL-1β, which are thought to play a role in psoriasis, did not stimulate keratinocyte proliferation in this RHE system (data not shown). Thus, those cytokines may play a secondary role in psoriasis or may play a role through a pathway independent of IL-19, IL-20, IL-22, and/or IL-24.

Immunohistochemistry was used to detect cytokeratin 16 (CK16), a marker of epidermal hyperplasia. IL-24, IL-22, and EGF induced CK16 expression throughout the non-cornified epidermis, while IL-19 and IL-20 only induced CK16 expression in the basal zone. (FIG. 37B.)

Figure 37E:
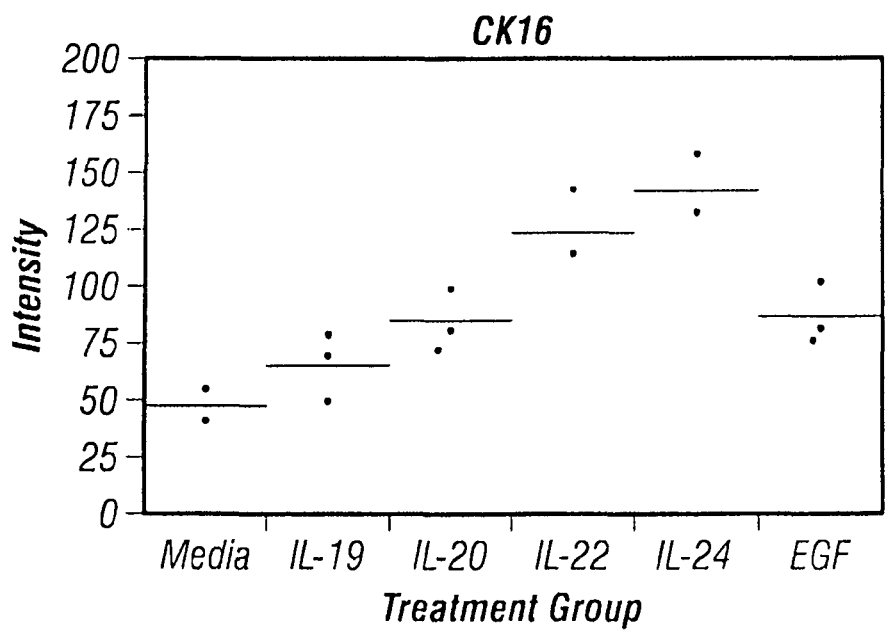
Figure 37F:
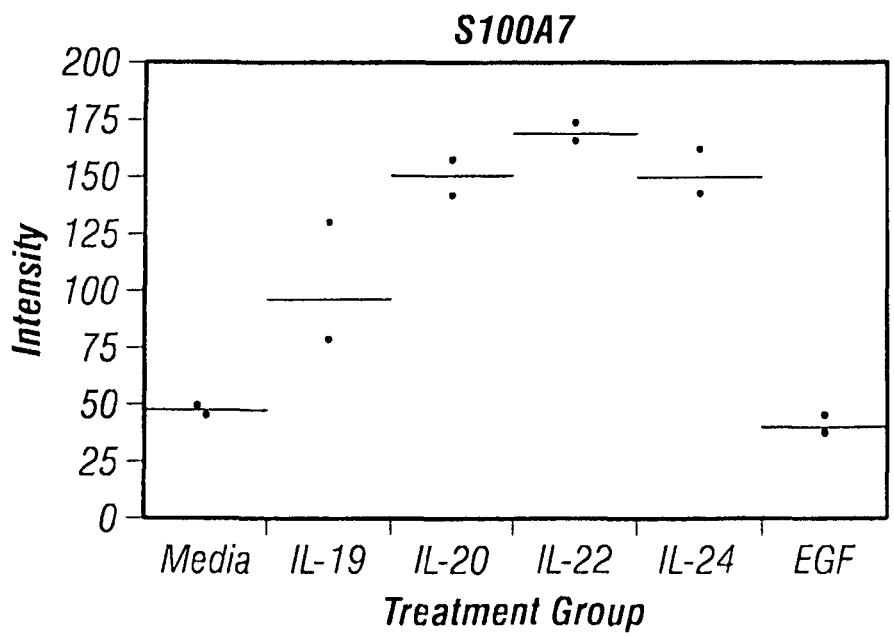
Figure 38:
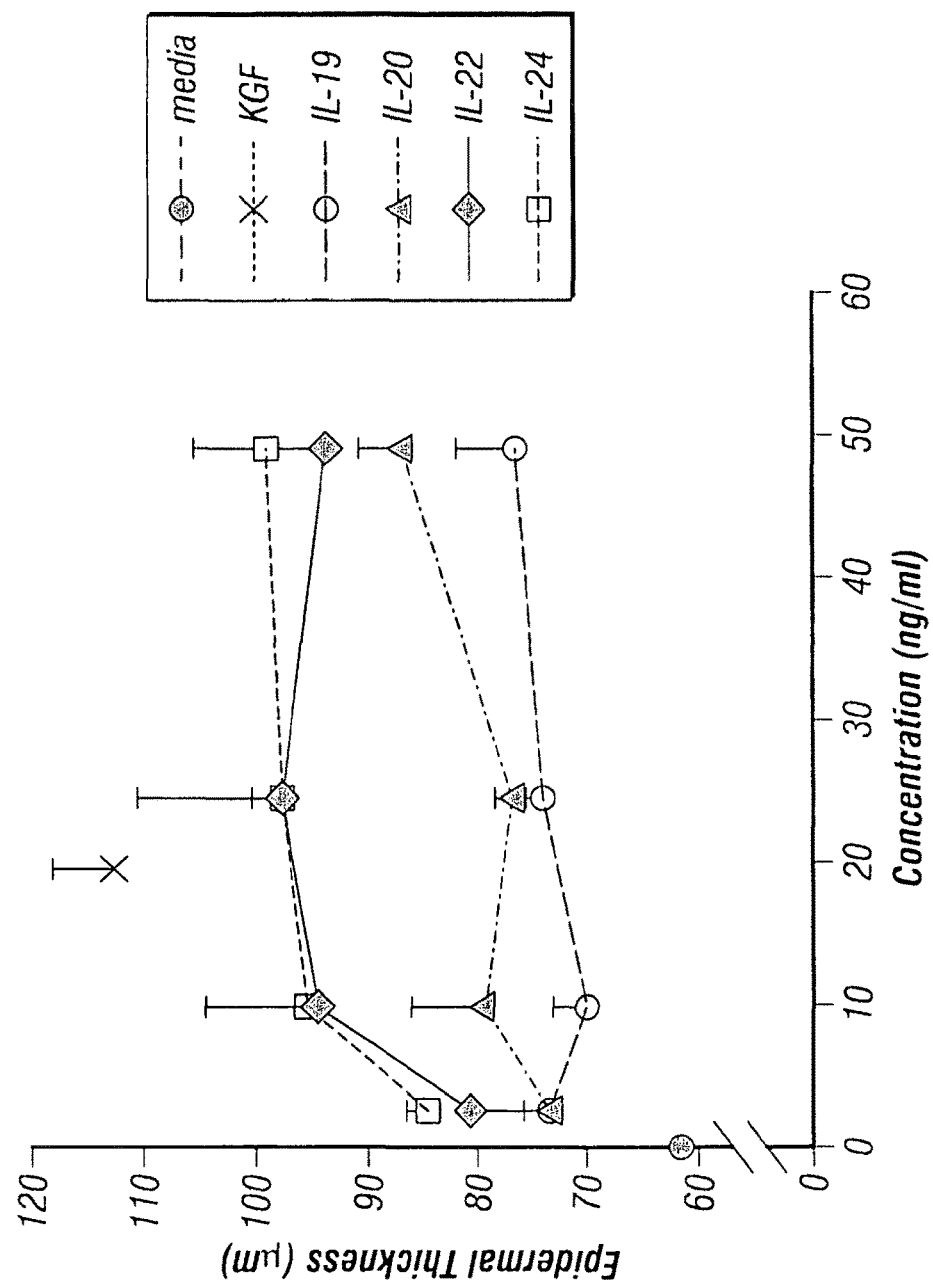
FIG. 38 shows quantification of epidermal acanthosis induced by IL-19, IL-20, IL-22, and IL24, as described in Example 23.

Immunohistochemistry was also used to detect psoriasin (S100A7), one of several S100 family proteins upregulated in certain hyperproliferative and inflammatory skin conditions, including psoriasis. IL-19, IL-20, IL-22, and IL-24 all induced S100A7 expression in the suprabasal epidermis, with IL-22 and IL-24 having the greatest effect. (FIG. 37C). S100A7 staining was observed in the nuclei and cytoplasm of the keratinocytes, with some protein also appearing to be extracellular. The results shown in FIGS. 37B and C were quantified and are displayed graphically in FIGS. 37E and F.

Immunohistochemistry was also used to detect pY(705)-STAT3, the transactivating form of STAT3. Activated STAT3 has been shown to be elevated in psoriatic lesional skin. IL-19, IL-20, IL-22, and IL-24 all induced persistent STAT3 activation in RHE keratinocytes found in all viable cell layers, demonstrated by its nuclear localization. (FIG. 37D).

Example 24

Figure 39A:
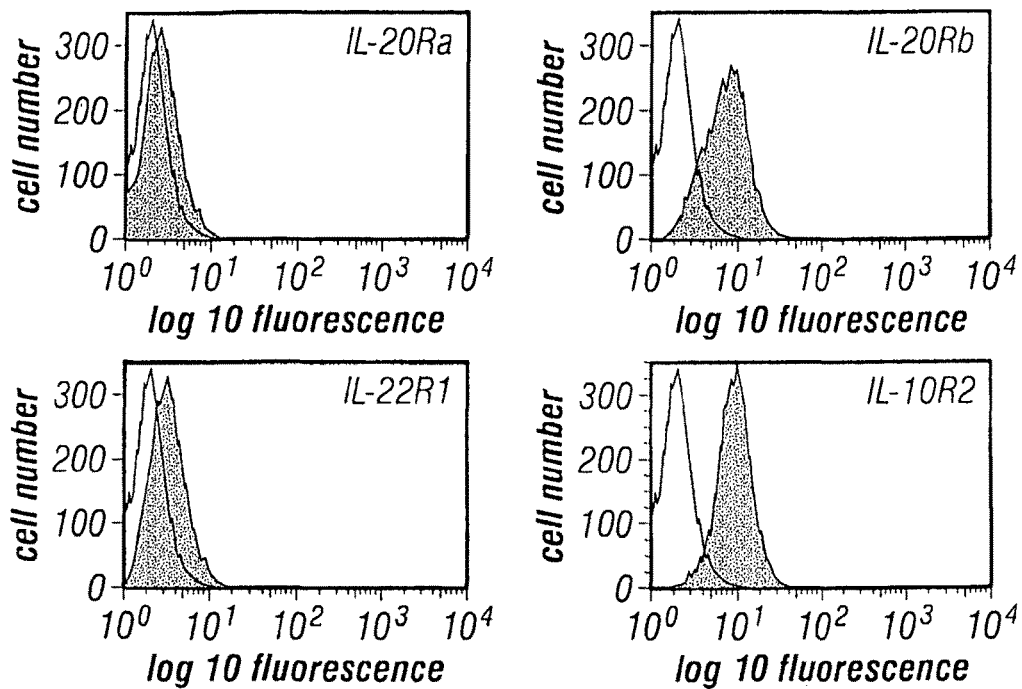
FIG. 39 shows that components of the receptors for IL-19, IL-20, and IL-22 are expressed on human keratinocytes, as described in Example 24.
Figure 39B:
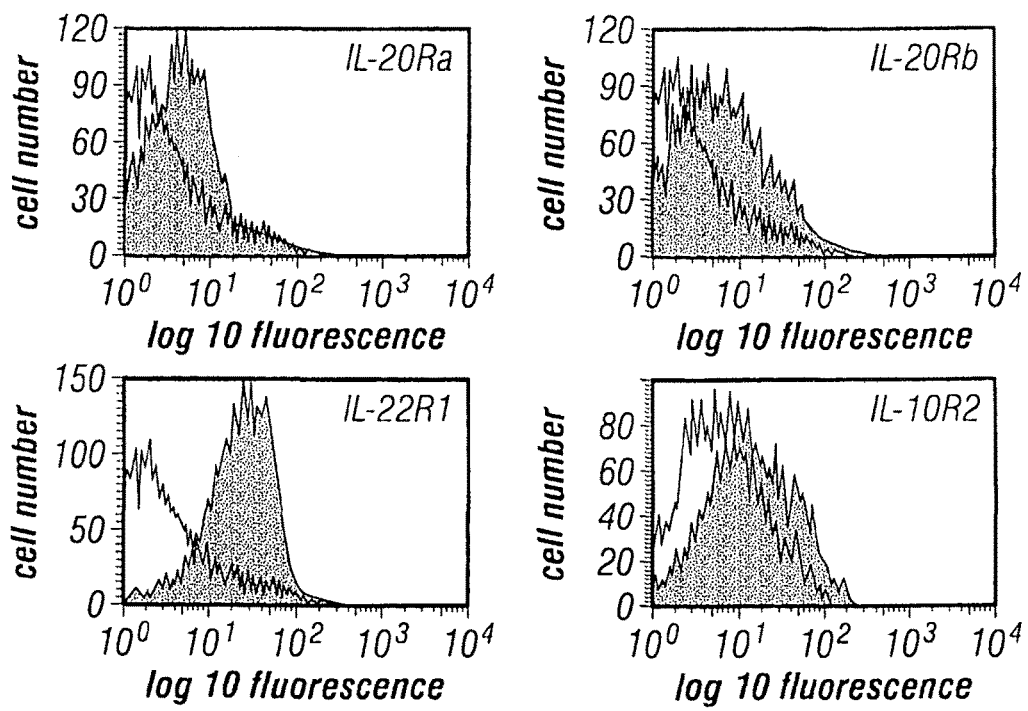

Blocking Antibodies to Receptors for IL-20 and IL-22 Reduce Psoriasin Expression Both IL-19 and IL-20 signal through a receptor heterodimer of IL20Ra and IL20Rb. IL20 also signals through a receptor heterodimer of IL-22R and IL-20Rb. IL-22 signals through a heterodimer of IL-22R and IL10R2. Cell surface expression of these receptor components on keratinocytes isolated from RHE or from primary cultures of normal human epidermal keratinocytes (NHEK, from donated neonatal foreskin) was examined by flow cytometry. The following monoclonal antibodies were used for flow cytometry: anti-IL20Ra (generated in mice for purposes of this study); anti-IL20Rb (generated in mice for purposes of this study); anti-IL-22R antibody 7E9 (described above); and anti-IL-10R2FAB874P (PE-conjugated) (R&D Systems, Minneapolis, Minn.). The results are shown in FIG. 39. The receptor component to which each antibody binds is shown in the upper right of each graph (IL-22R is designated as "IL-22R1"). IL-20Rb and IL10R2 were consistently expressed on the surface of NHEKs, regardless of confluence, passage number or calcium levels in the medium. (FIG. 39A.) In contrast, cell surface expression of both IL-20Ra and IL-22R1 on NHEK varied from donor to donor, and was consistently at a relatively low but detectable level. (FIG. 39A and data not shown.) Compared to expression levels in monolayer NHEK, IL-20Ra and IL-22R were expressed at much higher levels on keratinocytes isolated from RHE (FIG. 39B). The reasons for this difference are unknown. However, it is nonetheless clear that all of the receptor components analyzed are expressed on human keratinocytes. Expression of these receptor components on immune cells (T cells, B cells, natural killer cells, and monocytes) was not detected. (Data not shown.) Thus, the ligands for these receptor components likely provide a link between the immune system and keratinocyte abnormalities.

Figure 40:
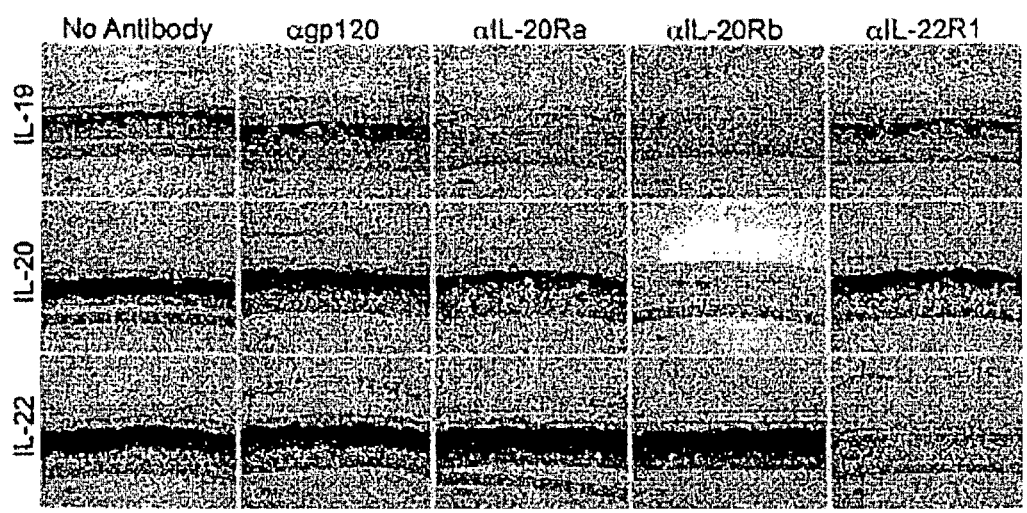
FIG. 40 shows that blocking antibodies to components of the receptors for IL-19, IL-20, and IL-22 reduce psoriasin expression, as described in Example 24.

To examine whether the above antibodies could block the effects of IL-19, IL-20, and IL-22 treatment, as described in the preceding Example, 20 micrograms/ml of anti-IL20Ra, anti-IL20Rb, or anti-IL-22R was added to RHE culture media one hour prior to addition of 20 ng/ml of IL-19, IL-20, or IL-22. RHE was then cultured for four days, with media changed at day two (4.5 ml fresh media including cytokine and antibody). The RHE was then stained by immunohistochemistry for psoriasin (S100A7). The results are shown in FIG. 40. IL-19, IL-20, and IL-22-treated RHE are shown in the first, second, and third rows, respectively. RHE pretreated with anti-IL20Ra (αIL-20Ra), anti-IL20Rb (αIL-20Rb), or anti-IL-22R (αIL-22R1) are shown in the third, fourth, and fifth columns, respectively. No antibody controls and isotype control antibodies are shown in the first and second columns.

The results show that either anti-IL20Ra or anti-IL20Rb effectively blocked IL-19-induced expression of psoriasin. Similarly, anti-IL-22R effectively blocked IL-22-induced expression of psoriasin. Anti-IL20Rb effectively blocked IL-20-induced expression of psoriasin, but anti-IL20Ra did not. Similarly, anti-IL-22R was unable to block IL-20-induced expression of psoriasin.

Figure 41:
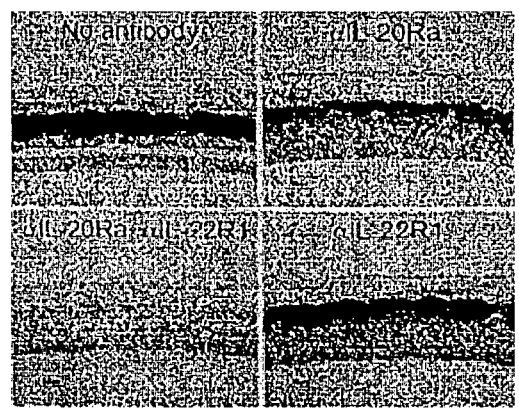
FIG. 41 shows that antibodies to IL20Ra and IL-22R, when used in combination, effectively block IL-20-induced expression of psoriasin.

To further investigate the effects of anti-IL-22R and anti-IL20Ra on IL-20-induced expression of psoriasin, RHE was pretreated with those antibodies either singly or in combination prior to treatment with IL-20. The results are shown in FIG. 41. As described above, either anti-IL-22R or anti-IL20Ra alone was unable to block IL-20-induced expression of psoriasin (second column, both panels). However, the combination of both anti-IL20Ra and anti-IL-22R effectively blocked IL-20 induced expression of psoriasin, suggesting that IL-20Ra and IL-22R have complementary roles in IL-20 signaling in human keratinocytes (lower left panel).

Example 25

IL-19, IL-20, IL-22, and IL-24 Induce Similar Gene Expression Profiles

To identify genes induced by IL-19, IL-20, IL-22, and IL-24, RHE was treated with 20 ng/ml of IL-19, IL-20, IL-22, or IL-24 for four days. RNA was prepared, and cDNA was hybridized to Affymetrix U133 Plus Gene Chips (Affymetrix, Santa Clara, Calif.), which contain 54,675 probesets. The data were analyzed for genes whose expression was increased by at least 2-fold. IL-20, IL-22, and IL-24 showed similar gene expression profiles. Of the top 20 genes commonly induced by IL-20, IL-22, and IL-24, seven were genes previously reported to be associated with psoriasis. Those genes are psoriasin (S100A7), S100A12, SCCA2, SERPINB4, CCL20, CD36, and Stat3.

To examine whether genes induced by IL-20, IL-22, and IL-24 show upregulation in psoriasis, the microarray analyses described above were compared with a previous microarray study of psoriatic skin (Zhou et al. (2003) *Physiol. Genomics* 13:69-78). Because that study was performed using a different microarray chip, only refseqs in common between that study and the present study were compared. Out of 468 refseqs that were upregulated in psoriatic skin, 356 were induced by IL-20, IL-22, and IL-24, and 188 of them were significant (p<0.05). Taken together, the above studies demonstrate substantial overlap between genes that are induced by IL-20, IL-22, and IL-24 and genes that are upregulated in psoriatic skin.

Example 26

Deposit of Materials

The following hybridoma cell line has been deposited with the American Type Culture Collection, 10801 University Blvd., Manassas, Va. 20110-2209 USA (ATCC):

| Hybridoma/Antibody Designation | ATCC No. | Deposit Date |
| --- | --- | --- |
| Anti-IL-22 (3F11.3) | PTA-7312 | Jan. 13, 2006 |
| Anti-IL-22 (11H4.4) | PTA-7315 | Jan. 13, 2006 |
| Anti-IL-22 (8E11.9) | PTA-7319 | Jan. 13, 2006 |
| Anti-IL-22R (7E9.10.8) | PTA-7313 | Jan. 13, 2006 |
| Anti-IL-22R (8A12.32) | PTA-7318 | Jan. 13, 2006 |
| Anti-IL-22R (8H11.32.28) | PTA-7317 | Jan. 13, 2006 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The cell line will be made available by ATCC under the terms of the Budapest Treaty, and subject to an agreement between Genentech, Inc. and ATCC, which assures (a) that access to the culture will be available during pendency of the patent application to one determined by the Commissioner to be entitled thereto under 37 CFR §1.14 and 35 USC §122, and (b) that all restrictions on the availability to the public of the culture so deposited will be irrevocably removed upon the granting of the patent.

The assignee of the present application has agreed that if the culture on deposit should die or be lost or destroyed when cultivated under suitable conditions, it will be promptly replaced on notification with a viable specimen of the same culture. Availability of the deposited cell line is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the material deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of treating psoriasis and/or disorders characterized by psoriatic symptoms mediated by IL-22 signaling activity, the method comprising administering to a mammal an effective amount of an anti-IL-22 antibody in a pharmaceutical formulation, wherein the IL-22 antibody is (a) an antibody produced by a hybridoma selected from the group consisting of 3F11.3 (ATCC Accession No. PTA-7312), hybridoma 11H4.4 (ATCC Accession No. PTA-7315), and hybridoma 8E11.9 (ATCC Accession No. PTA-7319); (b) an affinity matured form of the antibody of (a); (c) an antigen-binding fragment of the antibody of (a) or (b); or (d) a humanized form of the antibody of (a), (b), or (c); and wherein psoriatic symptoms mediated by IL-22 signaling activity are alleviated in the mammal.

2. The method of claim 1 further comprising administering at least one antibody selected from the group consisting of an antibody that specifically binds IL20Ra, an antibody that specifically binds IL20Rb, and an antibody that specifically binds IL-22R.

* * * * *

SEQUENCE LISTING

```
<160> NUMBER OF SEQ ID NOS: 4

<210> SEQ ID NO 1
<211> LENGTH: 1152
<212> TYPE: DNA
<213> ORGANISM: Homo sapiens

<400> SEQUENCE: 1
cttcagaaca ggttctcctt ccccagtcac cagttgctcg agttagaatt          50
gtctgcaatg gccgccctgc agaaatctgt gagctctttc cttatgggga         100
ccctggccac cagctgcctc cttctcttgg ccctcttggt acagggagga         150
gcagctgcgc ccatcagctc ccactgcagg cttgacaagt ccaacttcca         200
gcagccctat atcaccaacc gcaccttcat gctggctaag gaggctagct         250
tggctgataa caacacagac gttcgtctca ttggggagaa actgttccac         300
ggagtcagta tgagtgagcg ctgctatctg atgaagcagg tgctgaactt         350 caccccttgaa gaagtgctgt tccctcaatc tgataggttc cagccttata         400
tgcaggaggt ggtgcccttc ctggccaggc tcagcaacag gctaagcaca         450
tgtcatattg aaggtgatga cctgcatatc cagaggaatg tgcaaaagct         500
gaaggacaca gtgaaaaagc ttggagagag tggagagatc aaagcaattg         550
gagaactgga tttgctgttt atgtctctga gaaatgcctg catttgacca         600
gagcaaagct gaaaaatgaa taactaaccc cctttccctg ctagaaataa         650
caattagatg ccccaaagcg attttttta accaaaagga agatgggaag         700
ccaaactcca tcatgatggg tggattccaa atgaacccct gcgttagtta         750
caaaggaaac caatgccact tttgtttata agaccagaag gtagactttc         800
taagcataga tatttattga taacatttca ttgtaactgg tgttctatac         850
acagaaaaca atttattttt taaataattg tcttttttcca taaaaaagat         900 tactttccat tcctttaggg gaaaaaaccc ctaaatagct tcatgtttcc         950
ataatcagta ctttatattt ataaatgtat ttattattat tataagactg        1000
cattttattt atatcatttt attaatatgg atttatttat agaaacatca        1050
ttcgatattg ctacttgagt gtaaggctaa tattgatatt tatgacaata        1100
attatagagc tataacatgt ttatttgacc tcaataaaca cttggatatc        1150
cc                                                            1152
```

<210> SEQ ID NO 2
<211> LENGTH: 179
<212> TYPE: PRT
<213> ORGANISM: Homo sapiens

<400> SEQUENCE: 2

Met Ala Ala Leu Gln Lys Ser Val Ser Phe Leu Met Gly Thr
 1               5                  10                  15

Leu Ala Thr Ser Cys Leu Leu Leu Ala Leu Leu Val Gln Gly
                20                  25                  30

Gly Ala Ala Ala Pro Ile Ser Ser His Cys Arg Leu Asp Lys Ser
                35                  40                  45

Asn Phe Gln Gln Pro Tyr Ile Thr Asn Arg Thr Phe Met Leu Ala
                50                  55                  60

Lys Glu Ala Ser Leu Ala Asp Asn Asn Thr Asp Val Arg Leu Ile
                65                  70                  75

Gly Glu Lys Leu Phe His Gly Val Ser Met Ser Glu Arg Cys Tyr
                80                  85                  90

Leu Met Lys Gln Val Leu Asn Phe Thr Leu Glu Val Leu Phe
                95                  100                 105

Pro Gln Ser Asp Arg Phe Gln Pro Tyr Met Gln Glu Val Val Pro
                110                 115                 120

Phe Leu Ala Arg Leu Ser Asn Arg Leu Ser Thr Cys His Ile Glu
                125                 130                 135

Gly Asp Asp Leu His Ile Gln Arg Asn Val Gln Lys Leu Lys Asp
                140                 145                 150

Thr Val Lys Lys Leu Gly Glu Ser Gly Glu Ile Lys Ala Ile Gly
                155                 160                 165

Glu Leu Asp Leu Leu Phe Met Ser Leu Arg Asn Ala Cys Ile
                170                 175

<210> SEQ ID NO 3
<211> LENGTH: 574
<212> TYPE: PRT
<213> ORGANISM: Homo sapiens

<400> SEQUENCE: 3

Met Arg Thr Leu Leu Thr Ile Leu Thr Val Gly Ser Leu Ala Ala
 1               5                  10                  15

His Ala Pro Glu Asp Pro Ser Asp Leu Leu Gln His Val Lys Phe
                20                  25                  30

Gln Ser Ser Asn Phe Glu Asn Ile Leu Thr Trp Asp Ser Gly Pro
                35                  40                  45

Glu Gly Thr Pro Asp Thr Val Tyr Ser Ile Glu Tyr Lys Thr Tyr
                50                  55                  60

Gly Glu Arg Asp Trp Val Ala Lys Lys Gly Cys Gln Arg Ile Thr
                65                  70                  75

Arg Lys Ser Cys Asn Leu Thr Val Glu Thr Gly Asn Leu Thr Glu
                80                  85                  90

Leu Tyr Tyr Ala Arg Val Thr Ala Val Ser Ala Gly Gly Arg Ser
                95                  100                 105

Ala Thr Lys Met Thr Asp Arg Phe Ser Ser Leu Gln His Thr Thr
                110                 115                 120

Leu Lys Pro Pro Asp Val Thr Cys Ile Ser Lys Val Arg Ser Ile
                125                 130                 135

-continued

```
Gln Met Ile Val His Pro Thr Pro Thr Pro Ile Arg Ala Gly Asp
            140                 145                 150
Gly His Arg Leu Thr Leu Glu Asp Ile Phe His Asp Leu Phe Tyr
            155                 160                 165
His Leu Glu Leu Gln Val Asn Arg Thr Tyr Gln Met His Leu Gly
            170                 175                 180
Gly Lys Gln Arg Glu Tyr Glu Phe Phe Gly Leu Thr Pro Asp Thr
            185                 190                 195
Glu Phe Leu Gly Thr Ile Met Ile Cys Val Pro Thr Trp Ala Lys
            200                 205                 210
Glu Ser Ala Pro Tyr Met Cys Arg Val Lys Thr Leu Pro Asp Arg
            215                 220                 225
Thr Trp Thr Tyr Ser Phe Ser Gly Ala Phe Leu Phe Ser Met Gly
            230                 235                 240
Phe Leu Val Ala Val Leu Cys Tyr Leu Ser Tyr Arg Tyr Val Thr
            245                 250                 255
Lys Pro Pro Ala Pro Pro Asn Ser Leu Asn Val Gln Arg Val Leu
            260                 265                 270
Thr Phe Gln Pro Leu Arg Phe Ile Gln Glu His Val Leu Ile Pro
            275                 280                 285
Val Phe Asp Leu Ser Gly Pro Ser Ser Leu Ala Gln Pro Val Gln
            290                 295                 300
Tyr Ser Gln Ile Arg Val Ser Gly Pro Arg Glu Pro Ala Gly Ala
            305                 310                 315
Pro Gln Arg His Ser Leu Ser Glu Ile Thr Tyr Leu Gly Gln Pro
            320                 325                 330
Asp Ile Ser Ile Leu Gln Pro Ser Asn Val Pro Pro Pro Gln Ile
            335                 340                 345
Leu Ser Pro Leu Ser Tyr Ala Pro Asn Ala Ala Pro Glu Val Gly
            350                 355                 360
Pro Pro Ser Tyr Ala Pro Gln Val Thr Pro Glu Ala Gln Phe Pro
            365                 370                 375
Phe Tyr Ala Pro Gln Ala Ile Ser Lys Val Gln Pro Ser Ser Tyr
            380                 385                 390
Ala Pro Gln Ala Thr Pro Asp Ser Trp Pro Pro Ser Tyr Gly Val
            395                 400                 405
Cys Met Glu Gly Ser Gly Lys Asp Ser Pro Thr Gly Thr Leu Ser
            410                 415                 420
Ser Pro Lys His Leu Arg Pro Lys Gly Gln Leu Gln Lys Glu Pro
            425                 430                 435
Pro Ala Gly Ser Cys Met Leu Gly Gly Leu Ser Leu Gln Glu Val
            440                 445                 450
Thr Ser Leu Ala Met Glu Glu Ser Gln Glu Ala Lys Ser Leu His
            455                 460                 465
Gln Pro Leu Gly Ile Cys Thr Asp Arg Thr Ser Asp Pro Asn Val
            470                 475                 480
Leu His Ser Gly Glu Glu Gly Thr Pro Gln Tyr Leu Lys Gly Gln
            485                 490                 495
Leu Pro Leu Leu Ser Ser Val Gln Ile Glu Gly His Pro Met Ser
            500                 505                 510
Leu Pro Leu Gln Pro Pro Ser Gly Pro Cys Ser Pro Ser Asp Gln
            515                 520                 525
Gly Pro Ser Pro Trp Gly Leu Leu Glu Ser Leu Val Cys Pro Lys
```

```
                           530                 535                 540
Asp Glu Ala Lys Ser Pro Ala Pro Glu Thr Ser Asp Leu Glu Gln
                   545                 550                 555

Pro Thr Glu Leu Asp Ser Leu Phe Arg Gly Leu Ala Leu Thr Val
                   560                 565                 570

Gln Trp Glu Ser

<210> SEQ ID NO 4
<211> LENGTH: 263
<212> TYPE: PRT
<213> ORGANISM: Homo sapiens

<400> SEQUENCE: 4

Met Met Pro Lys His Cys Phe Leu Gly Phe Leu Ile Ser Phe Phe
  1               5                  10                  15

Leu Thr Gly Val Ala Gly Thr Gln Ser Thr His Glu Ser Leu Lys
                 20                  25                  30

Pro Gln Arg Val Gln Phe Gln Ser Arg Asn Phe His Asn Ile Leu
                 35                  40                  45

Gln Trp Gln Pro Gly Arg Ala Leu Thr Gly Asn Ser Ser Val Tyr
                 50                  55                  60

Phe Val Gln Tyr Lys Ile Met Phe Ser Cys Ser Met Lys Ser Ser
                 65                  70                  75

His Gln Lys Pro Ser Gly Cys Trp Gln His Ile Ser Cys Asn Phe
                 80                  85                  90

Pro Gly Cys Arg Thr Leu Ala Lys Tyr Gly Gln Arg Gln Trp Lys
                 95                 100                 105

Asn Lys Glu Asp Cys Trp Gly Thr Gln Glu Leu Ser Cys Asp Leu
                110                 115                 120

Thr Ser Glu Thr Ser Asp Ile Gln Glu Pro Tyr Tyr Gly Arg Val
                125                 130                 135

Arg Ala Ala Ser Ala Gly Ser Tyr Ser Glu Trp Ser Met Thr Pro
                140                 145                 150

Arg Phe Thr Pro Trp Trp Glu Thr Lys Ile Asp Pro Pro Val Met
                155                 160                 165

Asn Ile Thr Gln Val Asn Gly Ser Leu Leu Val Ile Leu His Ala
                170                 175                 180

Pro Asn Leu Pro Tyr Arg Tyr Gln Lys Glu Lys Asn Val Ser Ile
                185                 190                 195

Glu Asp Tyr Tyr Glu Leu Leu Tyr Arg Val Phe Ile Ile Asn Asn
                200                 205                 210

Ser Leu Glu Lys Glu Gln Lys Val Tyr Glu Gly Ala His Arg Ala
                215                 220                 225

Val Glu Ile Glu Ala Leu Thr Pro His Ser Ser Tyr Cys Val Val
                230                 235                 240

Ala Glu Ile Tyr Gln Pro Met Leu Asp Arg Arg Ser Gln Arg Ser
                245                 250                 255

Glu Glu Arg Cys Val Glu Ile Pro
                260
```